US008927503B2

(12) United States Patent
Fairlie et al.

(10) Patent No.: US 8,927,503 B2
(45) Date of Patent: Jan. 6, 2015

(54) MODULATIONS OF PROTEASE ACTIVATED RECEPTORS

(75) Inventors: David Paul Fairlie, Brisbane (AU); Ligong Liu, Brisbane (AU); Mei Kwan Yau, Brisbane (AU); Jacky Yung Suen, Brisbane (AU); Robert Reid, Brisbane (AU)

(73) Assignee: The University of Queensland (AU)

( * ) Notice: Subject to any disclaimer, the term of this patent is extended or adjusted under 35 U.S.C. 154(b) by 0 days.

(21) Appl. No.: 13/812,728

(22) PCT Filed: Jul. 28, 2011

(86) PCT No.: PCT/AU2011/000959
§ 371 (c)(1),
(2), (4) Date: Mar. 7, 2013

(87) PCT Pub. No.: WO2012/012843
PCT Pub. Date: Feb. 2, 2012

(65) Prior Publication Data
US 2013/0184226 A1 Jul. 18, 2013

(30) Foreign Application Priority Data
Jul. 28, 2010 (AU) ................................ 2010903378

(51) Int. Cl.
| A61K 38/06 | (2006.01) |
| A61K 38/07 | (2006.01) |
| A61K 38/05 | (2006.01) |
| C07K 5/00 | (2006.01) |
| C07K 7/00 | (2006.01) |
| C07K 16/00 | (2006.01) |
| C07K 17/00 | (2006.01) |
| C07D 401/00 | (2006.01) |
| C07D 451/00 | (2006.01) |
| C07D 453/00 | (2006.01) |
| C07D 455/00 | (2006.01) |
| C07D 471/00 | (2006.01) |
| C07K 5/083 | (2006.01) |
| C07K 5/065 | (2006.01) |
| C07K 5/062 | (2006.01) |
| A61K 38/00 | (2006.01) |

(52) U.S. Cl.
CPC .......... *C07K 5/00* (2013.01); *C07K 5/0806* (2013.01); *C07K 5/06078* (2013.01); *A61K 38/00* (2013.01); *C07K 5/06034* (2013.01); *C07K 5/081* (2013.01)
USPC .......... 514/21.9; 514/21.91; 530/331; 546/17

(58) Field of Classification Search
None
See application file for complete search history.

(56) References Cited

U.S. PATENT DOCUMENTS 4,522,811 A    6/1985 Eppstein et al.
5,578,593 A    11/1996 Chen et al.

FOREIGN PATENT DOCUMENTS

EP    0838471        4/1998
EP    0838471 A1 *  4/1998
EP    1845104        10/2007

OTHER PUBLICATIONS

Sharma et al "Discovery of Trp-His and His-Arg Analogs as New Structural Classes of Short Antimicrobial Peptides" J Med Chem 52:7421-7431, published online Aug. 5, 2009.*
Barry et al "Novel Agonists and Antagonists for Human Protease Activated Receptor 2" J Med Chem 53:7428-7440. Published online Sep. 28, 2010.*
Barry et al., "A refined agonist pharmacophore for protease activated receptor 2", Bioorganic & Medicinal Chemistry Letters, 2007, 27, 5552-5557.
Barry et al., "Novel Agonists and Antagonists for Human Protease Activated Receptor 2", Journal of Medicinal Chemistry, 2010, 53, 7428-7440.
Barry, "Agonists and Antagonists of Protease Activated Receptor-2 ($PAR_2$)", Thesis, Institute for Molecular Bioscience, The University of Queensland, Nov. 2008, 261 pages.
Berge et al., "Pharmaceutical Salts", Journal of Pharmaceutical Sciences, 1977, 66, 1-19.
Boitano et al., "Potent Agonists of the Protease Activated Receptor 2 ($PAR_2$)", Journal of Medicinal Chemistry, 2011, 54, 1308-13.
Earp et al., "Pharmacokinetics of Dexamethasone in a Rat Model of Rheumatoid Arthritis", Biopharm. Drug Dispos., 2008, 366-372.
Flick et al., "Fibrin(ogen) exacerbates inflammatory joint disease through a mechanism linked to the integrin $\alpha M\beta_2$ binding motif", The Journal of Clinical Investigation, 2007, 117, 3224-3235.

(Continued)

*Primary Examiner* — Maury Audet
*Assistant Examiner* — Zachary J Miknis
(74) *Attorney, Agent, or Firm* — Baker & Hostetler LLP

(57) ABSTRACT

The present invention provides novel compounds of the Formula (1), pharmaceutical compositions comprising such compounds and methods for using such compounds as tools for biological studies or as agents or drugs for modulating Protease Activated Receptor-2 (PAR2) and for treating a subject at risk of—or susceptible to—a disease or disorder, or having a disease or disorder associated with undesirable PAR2 activity.

(I)

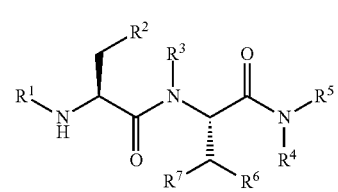

10 Claims, 11 Drawing Sheets

(56) References Cited

OTHER PUBLICATIONS

Flynn et al., "The Protease-activated Receptor-2-specific Agonists 2-Aminothiazol-4-yl-LIGRL-NH$_2$ and 6-Aminonicotinyl-LIGRL-NH$_2$ Stimulate Multiple Signaling Pathways to Induce Physiological Responses in Vitro and in Vivo", Journal of Biological Chemistry, 2011, 286, 19076-88.
Goh et al., "Dual effect of the novel peptide antagonist K-14585 on proteinase-activated receptor-2-mediated signaling", British Journal of Pharmacology, 2009, 158, 1695-1704.
Hollenberg et al., "Derivatized 2-Furoyl-LIGRLO-amide, a Versatile and Selective Probe for Proteinase-Activated Receptor 2: Binding and Visualization", The Journal of Pharmacology and Experimental Therapeutics, 2008, 326, 453-62.
International Patent Application No. PCT/AU2011/000959: International Search Report dated Sep. 26, 2011, 3 pages.
Kanke et al., "Novel antagonists for proteinase-activated receptor 2: inhibition of cellular and vascular responses in vitro and in vivo", British Journal of Pharmacology, 2009, 158, 361-371.
Kelso et al., "Role of Protease-Activated Receptor 2 in Joint Inflammation", Arthritis & Rheumatism, 2007, 56, 765-71.
Kelso et al., "Therapeutic Promise of Proteinase-Activated Receptor-2 Antagonism in Joint Inflammation", The Journal of Pharmacology and Experimental Therapeutics, 2006, 316, 1017-24.
Lin et al., "Anti-rheumatic activities of histone deacetylase (HDAC) inhibitors in vivo in collagen-induced arthritis in rodents", British Journal of Pharmacology, 2007, 150, 862-72.
McGuire et al., "2-Furoyl-LIGRLO-amide: A Potent and Selective Proteinase-Activated Receptor 2 Agonist", The Journal of Pharmacology and Experimental Therapeutics, 309, 2004, 1124-1131.
Nishikawa et al., "Prevention of the Onset and Progression of Collagen-Induced Arthritis in Rats by the Potent p38 Mitogen-Activated Protein Kinase Inhibitor FR167653", Arthritis & Rheumatism, 2003, 48, 2670-81.
Olofsson et al., "A Comparative Genetic Analysis Between Collagen-Induced Arthritis and Pristane-Induced Arthritis", Arthritis & Rheumatism, 2003, 48, 2332-42.
Seitzberg et al., "Discovery of Potent and Selective Small-Molecule PAR-2 Agonists", Journal of Medicinal Chemistry, 2008, 51, 5490-3.
Sharma et al., "Discovery of Trp-His and His-Arg Analogues as New Structural Classes of Short Antimicrobial Peptides", Journal of Medicinal Chemistry, 2009, 52, 7421-7431.
Stereosearch, "CAS Registry No. 210558-02-4", https://stneasy.cas.org/tmp/2011026/385028-1839221245-200/478801495.html, Aug. 30, 1998, 1 page.
Stereosearch, "CAS Registry No. 210558-06-8", https://stneasy.cas.org/tmp/2011026/385028-1839221245-200/653848274.html, Aug. 30, 1998, 1 page.
Stereosearch, "CAS Registry No. 210558-10-4", https://stneasy.cas.org/tmp/2011026/385028-1839221245-200/432988596.html, Aug. 30, 1998, 1 page.
Stereosearch, "CAS Registry No. 210558-12-6", https://stneasy.cas.org/tmp/2011026/385028-1839221245-200/208300584.html, Aug. 30, 1998, 1 page.
Stereosearch, "CAS Registry No. 210558-18-2", https://stneasy.cas.org/tmp/2011026/385028-1839221245-200/40757013.html, Aug. 30, 1998, 1 page.
Stereosearch, "CAS Registry No. 738563-36-5", https://stneasy.cas.org/tmp/2011026/385028-1839221245-200/26844823.html, Sep. 3, 2004, 1 page.
Stereosearch, "CAS Registry No. 742034-60-2", https://stneasy.cas.org/tmp/2011026/385028-1839221245-200/56636795.html, Sep. 10, 2004, 1 page.
Stereosearch, "CAS Registry No. 759429-93-1", https://stneasy.cas.org/tmp/2011026/385028-1839221245-200/387965189.html, Oct. 8, 2004, 1 page.
Stereosearch, "CAS Registry No. 773035-26-0", https://stneasy.cas.org/tmp/2011026/385028-1839221245-200/519179466.html, Oct. 31, 2004, 1 page.
Stereosearch, "CAS Registry No. 775559-52-9", https://stneasy.cas.org/tmp/2011026/385028-1839221245-200/519179466.html, Nov. 7, 2004, 1 page.
Stereosearch, "CAS Registry No. 785028-07-1", https://stneasy.cas.org/tmp/2011026/385028-1839221245-200/423842365.html, Nov. 21, 2004, 2 pages.
Vergnolle, "Proteinase-Activated Receptor-2-Activating Peptides Induce Leukocyte Rolling, Adhesion, and Extravasation In Vivo", The Journal of Immunology, 1999, 163, 5064-9.
Woodruff et al., "Antiarthritic Activity of an Orally Active C5a Receptor Antagonist Against Antigen-Induced Monarticular Arthritis in the Rat", Arthritis & Rheumatism, 2002, 46, 2476-85.

* cited by examiner

A.

B.

MODULATIONS OF PROTEASE ACTIVATED RECEPTORS

CROSS-REFERENCE TO RELATED APPLICATIONS

This application is the National Stage of International Application No. PCT/AU2011/000959, filed Jul. 28, 2011, which claims the benefit of Australian Application No. 2010903378, filed Jul. 28, 2010, the disclosures of which are incorporated herein by reference in their entireties.

FIELD OF THE INVENTION

The present invention relates generally to compounds capable of modulating Protease Activated Receptor-2 (PAR2), and uses thereof. More specifically, the present invention relates to modulators of PAR2, to their preparation, and to their use as tools for biological studies or as agents or drugs for therapies, whether they are used alone or in combination with other treatment modalities.

BACKGROUND

Protease activated receptor-2 (PAR2) is a unique G-protein coupled receptor (GPCR) in that it has no known endogenous extracellular ligand, but rather is activated by proteases including many serine proteases such as trypsin, tryptase, and cathepsin G. Serine proteases cleave a section of the membrane bound receptor's extracellular N-terminus, exposing a new sequence which acts as a tethered ligand by binding to the receptor and initiating activation.

Distributed widely throughout the body, PAR2 has been implicated as a pro-inflammatory mediator in acute and chronic inflammatory diseases including arthritis, inflammatory bowel disease, pancreatitis, and cardiovascular diseases. PAR2 has also been reported as anti-inflammatory and protective in conditions such as gastric ulcer, colitis, asthma, and liver fibrosis, although this remains controversial. PAR2 activation has been linked to proliferation, metastasis and angiogenesis in many cancers including cancers of the stomach, colon, breast and pancreas. In this context, small-molecule modulators of PAR2 are of potential interest as a new class of anti-inflammatory, pro-inflammatory, anti-proliferative or proliferative agents.

Trypsin is a potent activator of PAR2 in the GI tract where pancreatic trypsin is found, and in colon, airway epithelium, neuronal and vascular endothelial cells, skin, intestine, kidney and pancreas where trypsinogen expression has been demonstrated. Mast cell tryptase is also an important activator of PAR2, being highly expressed in mast cells and strongly associated with many inflammatory, endocrine and other diseases. Hexapeptides SLIGKV-$NH_2$ and SLIGRL-$NH_2$, corresponding to the tethered ligand human and murine sequences respectively, can activate human PAR2 in lieu of serine proteases, albeit at lower potency (μM instead of nM concentrations).

More potent peptide agonists have been created for PAR2. The hexapeptide analogue. 2-furoyl-LIGRL-$NH_2$, has ~20-fold higher agonist potency than SLIGRL-$NH_2$ and is selective for PAR2 over PAR1. Other heterocyclic replacements for serine result in equipotent PAR2 agonists, while large aromatic groups in place of the C-terminal leucine impart a similar enhancement in PAR2 agonist potency (McGuire, J. J. et al. J Pharmacol Exp Ther 2004, 309, 1124-31; Barry G D et al, Bioorg Med Chem 2007, 27, 5552-7; Hollenberg, M. D., et al, J Pharmacol Exp Ther 2008, 326, 453-62; Boitano. C. et al, J Med Chem 2011, 54, 1308-13; Flynn, A. N., et al, J Biological Chem 2011, 286, 19076-88). Screening of 250,000 drug-like compounds produced two small molecule agonists of PAR2 with similar agonist potency to 2-furoyl-LIGRL-$NH_2$, some selectivity for PAR2 and metabolic stability in vivo (Seitzberg, J. G., et al. J Med Chem 2008, 51, 5490-3).

The first known antagonist of PAR2 had affinity at only millimolar concentrations for the receptor and selectivity is most unlikely (Kelso. E. B., et al. J Pharmacol Exp Ther 2006. 316, 1017-24). A second antagonist reported for PAR2 is active at μM concentrations, but completely inactive against endogenous PAR2 activators like trypsin (Kanke, T. et al. Br J Pharmacol 2009, 158, 361-371) or has a dual function as an antagonist and agonist due to either partial agonist actions or possible agonist-directed signalling (Goh, F. G., et al. Br J Pharmacol 2009, 158, 1695-1704).

In one or more aspects, the present invention may advantageously provide a novel class of compounds that can selectively modulate PAR2 when used at low micromolar or sub-micromolar concentrations. Depending upon structural characteristics, and intracellular pathways being examined, these novel compounds may act as either agonists or antagonists and be useful as tools for biological studies or as agents for anti-inflammatory, pro-inflammatory, anti-proliferative or proliferative therapies.

SUMMARY OF THE INVENTION

In one aspect, the present invention provides compounds of the formula (I):

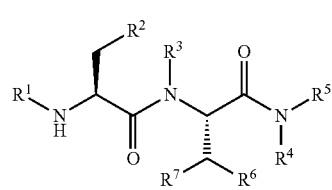

wherein $R^1$ is hydrogen or —$C(O)R^8$; wherein $R^8$ is a 5- or 6-membered saturated or unsaturated heterocyclic ring comprising 1 to 3 heteroatoms selected from N and O, optionally substituted with one or more substituents selected from alkyl, alkoxy, amine, aminoalkyl, amidoalkyl, halo, hydroxy, trihaloalkyl, trihaloalkoxy or phenyl, wherein the phenyl group may be further optionally substituted with 1 to 3 substituents selected from alkyl, alkoxy, hydroxy, halo, nitro, trihaloalkyl, or trihaloalkoxy;

$R^2$ is an aromatic or aliphatic $C_3$-$C_8$cyclic group or $C_3$-$C_8$heterocyclic group comprising 1 to 3 heteroatoms selected from N and O, wherein the $C_3$-$C_8$cyclic group or $C_3$-$C_8$heterocyclic group may be further substituted with one or more substituents selected from alkyl, amine, hydroxy, or the cyclic group or heterocyclic group is fused with an optionally substituted aromatic or aliphatic $C_3$-$C_8$cyclic group or $C_3$-$C_8$heterocyclic group;

$R^3$ is hydrogen or $C_1$-$C_6$alkyl;

$R^4$ is hydrogen, $C_1$-$C_6$alkyl, aminoalkyl or amidoalkyl;

$R^5$ is a benzyl group optionally substituted with a group selected from alkyl, aminoalkyl, alkoxy, $C_4$-$C_7$heterocycle, hydroxy, halo, nitro, dioxalane, trihaloalkyl, trihaloalkoxy or —$C(O)NHCHR^9R^{10}$; wherein $R^9$ is —$C(O)NH_2$ and $R^{10}$ is a $C_2$-$C_5$-aminoalkyl; or $R^4$ and $R^5$ combined, together with the nitrogen to which they are attached, form piperidine, optionally substituted with a group selected from phenyl, benzyl, aminoalkyl, aminoaryl, amidoalkyl or a heterocycle, or piperidine is fused with an aromatic or aliphatic $C_3$-$C_8$cyclic group or $C_3$-$C_8$heterocyclic group; wherein the phenyl, benzyl, aminoaryl, heterocycle or fused aromatic or aliphatic $C_3$-$C_8$cyclic group or $C_3$-$C_8$heterocyclic group may be further substituted with 1 to 3 substituents selected from alkyl, alkylamine, alkylsulfonyl, alkoxy, aminoalkyl, aminoaryl, amidoalkyl, arylamine, hydroxy, halo, nitro, oxo, optionally substituted phenyl, optionally substituted piperidine, dioxalane, trihaloalkyl, or trihaloalkoxy; or the fused aromatic or aliphatic $C_3$-$C_8$cyclic group or $C_3$-$C_8$heterocyclic group is fused with an additional $C_6$-$C_{10}$cyclic or $C_6$-$C_{10}$heterocyclic group;

$R^6$ is hydrogen or $C_1$-$C_6$alkyl;

$R^7$ is $C_1$-$C_6$alkyl, amino, hydroxy, alkoxy, aminoalkyl, amidoalkyl, saturated or unsaturated cycloalkyl, or heterocycle; or a salt thereof;

provided that the compound is not 5-isoxazoyl-Cha-Ile-spiro[indene-1,4'-piperidine], 5-isoxazoyl-Cha-Ile-spiro[indane-1,4'-piperidine] or 5-isoxazoyl-Cha-Ile-spiro[octahydro-1H-indene-1,4'-piperidine].

In a further aspect, the present invention provides compounds of formula (I) represented by the formula (Ia):

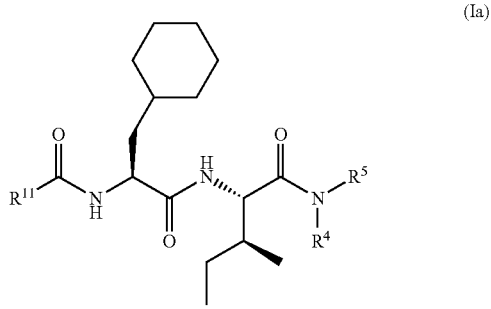

(Ia)

wherein $R^{11}$ is a 5- or 6-membered unsaturated heterocyclic ring comprising 1 to 3 heteroatoms selected from N and O, optionally substituted with one or more groups selected from alkyl or phenyl, wherein the phenyl group may be further optionally substituted with 1 to 3 substituents selected from alkyl, alkoxy, hydroxy, halo, nitro, trihaloalkyl or trihaloalkoxy;

$R^4$ is hydrogen, $C_1$-$C_6$alkyl, aminoalkyl or amidoalkyl:

$R^5$ is a benzyl group, optionally substituted with a group selected from alkyl, aminoalkyl, alkoxy, $C_4$-$C_7$heterocycle, hydroxy, halo, nitro, dioxalane, trihaloalkyl, trihaloalkoxy or —C(O)NHCHR$^9$R$^{10}$; wherein $R^9$ is —C(O)NH$_2$ and $R^{10}$ is a $C_2$-$C_5$aminoalkyl;

or $R^4$ and $R^5$ combined, together with the nitrogen to which they are attached, form piperidine, optionally substituted with a group selected from phenyl, benzyl, aminoalkyl, amidoalkyl or a heterocycle; wherein the phenyl, benzyl or heterocycle may be further substituted with 1 to 3 substituents selected from alkyl, alkyloxy, aminoalkyl, amidoalkyl, hydroxy, halo, nitro, dioxalane, trihaloalkyl, or trihaloalkoxy;

or a salt thereof.

In a further aspect, the present invention provides a method of modulating the activity of PAR2 comprising exposing the receptor to a compound of the present invention, or a salt thereof.

In a further aspect, the present invention provides pharmaceutical compositions comprising a compound of the present invention, or a salt thereof, preferably together with a pharmaceutically acceptable carrier, excipient, diluent and/or adjuvant.

In still a further aspect, the present invention provides a prophylactic or therapeutic method of treating a subject at risk of or susceptible to a disease or disorder, or having a disease or disorder associated with undesirable PAR2 activity, comprising administering a compound according to the present invention, or a salt thereof, to a subject in need thereof. Preferably, the disease or disorder is an inflammatory disease or disorder, or a proliferative disease or disorder.

In still a further aspect, the present invention provides the use of the compounds of the present invention, or salts thereof, for the prophylactic or therapeutic treatment of a subject at risk of or susceptible to a disease or disorder, or having a disease or disorder associated with undesirable PAR2 activity. Preferably, the disease or disorder is an inflammatory disease or disorder, or a proliferative disease or disorder.

In still a further aspect, the present invention provides the use of the compounds of the present invention, or salts thereof, in the manufacture of a medicament for the prophylactic or therapeutic treatment of a subject at risk of or susceptible to a disease or disorder, or having a disease or disorder associated with undesirable PAR2 activity. Preferably, the disease or disorder is an inflammatory disease or disorder, or a proliferative disease or disorder.

In a preferred aspect the compounds of the present invention are PAR2 antagonists.

In a further preferred aspect the compounds of the invention are PAR2 agonists.

DETAILED DESCRIPTION OF THE INVENTION

Figure 1:
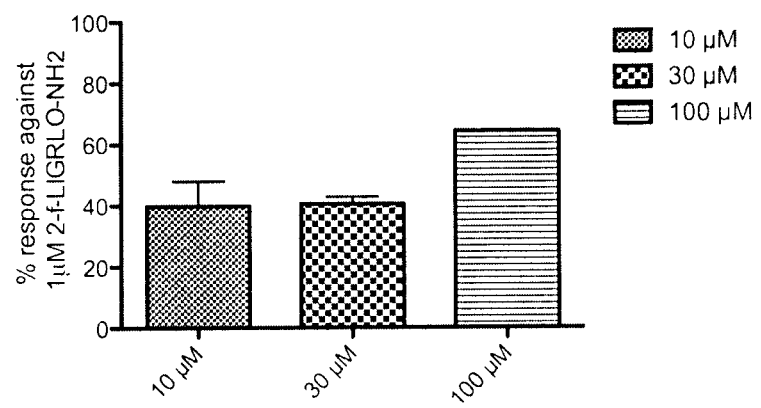
FIG. 1: Graphical representation of a three point concentration bar graph for PAR2 agonist 6 on HT29 cells.

Despite evidence of its apparent role in the aforementioned pathophysiologies, the biological function of PAR2 remains poorly understood, particularly at the in vivo level.

This lack of substantial progress has been mostly attributed to a lack of potent and selective, biologically active agonists and antagonists of PAR2 for the purposes of further investigation.

Structure activity relationship studies, starting from the hexapeptide agonists SLIGKV-NH$_2$ and SLIGRL-NH$_2$, have enabled the present inventors to determine the specific side-chain functionalities required for these peptidic ligands to bind to and activate PAR2. By utilising this information, the present inventors have, for the first time, been able to rationally design and develop potent, selective and orally active non-peptidic modulators of the receptor. In the process, the inventors have been able to determine those fragments of the novel compounds that are required for receptor recognition and those regions that impart agonist or antagonist functionality. In some embodiments, these novel compounds provide a means of treating or preventing diseases or disorders associated with aberrant PAR2 expression and/or activity.

In this specification a number of terms are used which are well known to a skilled addressee. Nevertheless for the purposes of clarity a number of terms will be defined.

As used herein, the term "unsubstituted" means that there is no substituent or that the only substituents are hydrogen.

In this specification, unless otherwise defined, the term "optionally substituted" is taken to mean that a group may or may not be further substituted or fused (so as to form a condensed polycyclic group) with one or more groups selected from hydroxyl, alkyl, alkoxy, alkenyl, alkenyloxy, alkynyl, alkynyloxy, amino, aminoacyl, thio, arylalkyl, arylalkoxy, aryl, aryloxy, acylamino, cyano, halogen, nitro, sulfo, phosphono, phosphorylamino, phosphinyl, heteroaryl, heteroaryloxy, heterocyclyl, hetcrocycloxy, oxyacyl, oxime, oxime ether, hydrazone, —NHC(NH)NH$_2$, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl, amino, and unsymmetric di-substituted amines having different substituents selected from alkyl, aryl, heteroaryl and heterocyclyl.

In certain embodiments the preferred substituent groups are one or more groups independently selected from alkyl, phenyl, alkoxy, halo, nitro, trihaloalkyl, trihaloalkyloxy or a group of the formula —C(O)NHCHR$^5$R$^6$ wherein R$^5$ is —C(O)NH$_2$ and R$^6$ is a C$_1$-C$_5$alkylamine.

"Alkyl" as a group or part of a group refers to a straight or branched aliphatic hydrocarbon group, preferably a C$_1$-C$_{10}$alkyl, more preferably a C$_1$-C$_8$alkyl, most preferably C$_1$-C$_6$ unless otherwise noted. Examples of suitable straight and branched C$_1$-C$_6$alkyl substituents include methyl, ethyl, n-propyl, 2-propyl, n-butyl, sec-butyl, t-butyl, hexyl, and the like.

The term "amino" herein refers to a nitrogen radical substituted with hydrogen, alkyl, aryl or combinations thereof.

In this specification, reference to amino acids including naturally occurring amino acids such as serine, leucine, isoleucine, glycine, arginine, lysine or valine, or amino acids that are not naturally occurring such as cyclohexylalanine, either by their complete name, their common three letter code (e.g. Ser, Leu, Ile, Gly, Arg, Lys, Val or Cha) or their single letter code (e.g. S, L, I, G, R, K or V) is taken to mean the L-isomer, unless otherwise specified.

The term "alkylamine" refers to an amine further hound to an alkyl group as defined herein and includes both mono- and di-alkylamines, unless specified. The alkyl group is preferably a C$_1$-C$_{10}$ alkyl group. The group is bonded to the remainder of the molecule through the nitrogen atom.

The term "alkylamide" refers to a group of the formula —C(O)NR$_2$ wherein at least one of the R substituents represents an alkyl group as defined herein. Alkylamides include both mono- and di-alkylamides, unless specified. One skilled in the art would recognise that in the case of mono-alkylamides the remaining R substituent represents hydrogen. The alkyl group is preferably a C$_1$-C$_{10}$alkyl group. The group is bonded to the remainder of the molecule through the nitrogen atom.

The term "aminoalkyl" refers to an alkyl group as defined herein, further substituted with at least one amine. Preferred aminoalkyl groups are C$_2$-C$_{10}$aminoalkyl groups. The group is bonded to the remainder of the molecule through an alkyl carbon atom.

The term "amidoalkyl" refers to an alkyl group as defined herein, further substituted with at least one amide group, i.e. a group of the formula alkyl-C(O)NH$_2$. Preferred amidoalkyl groups are C$_2$-C$_{10}$amidoalkyl groups. The group is bonded to the remainder of the molecule through an alkyl carbon atom.

"Aryl" as a group or part of a group denotes an optionally substituted monocyclic, or fused polycyclic, aromatic carbocyclic (ring structure having ring atoms that are all carbon) preferably having from 5 to 12 atoms per ring. Examples of aryl groups include monocyclic groups such as phenyl, fused polycyclic groups such as naphthyl, and the like. Typically an aryl group is a C$_6$-C$_{10}$aryl group.

The term "fused" when used with reference to bicyclic or polycyclic groups refers to bicyclic or polycyclic ring systems in which at least two of the rings share a common C—C bond such as ortho-or peri-fused bicyclic or polycyclic ring systems. The term "fused" also includes bicyclic or polycyclic ring systems that share only one common C atom such as bicyclic and polycyclic spiro ring systems.

The term "arylamine" refers to an amine further bound to an aryl group as defined herein and includes both mono- and di-arylamines, unless specified. The aryl group is preferably a C$_6$-C$_{10}$aryl group. The group is bonded to the remainder of the molecule through the nitrogen atom.

The term "aminoaryl" refers to an aryl group as defined herein, further substituted with at least one amine. Preferred aminoaryl groups are C$_6$-C$_{10}$aminoaryl groups. The group is bonded to the remainder of the molecule via an aryl carbon atom.

The term "alkoxy" as a group or part of a group refers to an alkyl-O— group in which alkyl is as defined herein. Preferably the alkoxy is a C$_1$-C$_{10}$alkoxy. Examples include, but are not limited to, methoxy and ethoxy.

The term "cycle" or "cyclic group" refers to a saturated, partially unsaturated or fully unsaturated monocyclic or fused or spiro polycyclic, ring systems preferably containing from 3 to 10 carbons per ring.

The term "halo" used herein refers to fluoro, chloro, bromo or iodo.

The term "heterocycle" or "heterocyclic group" refers to saturated, partially unsaturated or fully unsaturated monocyclic, bicyclic or fused polycyclic or spiro polycyclic ring systems containing at least one heteroatom selected from the group consisting of nitrogen, sulfur and oxygen as a ring atom. Each ring is preferably from 3 to 10 membered, more preferably 4 to 7 membered. Examples of suitable heterocyclic substituents include, but are not limited to, pyrrole, furan, benzofuran, benzothiazole, imidazole, benzimidazole, imidazoline, pyrazole, pyrazoline, triazole, oxazole, oxazoline, isoxazole, isoxazoline, furazan, oxadiazole, piperidine, pyridine, pyrimidine, pyridazine and pyrazine, each of which may be further substituted with 1 to 3 substituents.

In some preferred embodiments of the invention, and with reference to the general formula (I), one or more of the following preferred embodiments apply:

a) $R^1$ is selected from acyl derivatives of pyrrole, pyridine, pyrazine, furan, benzofuran, benzothiazole, imidazole, imidazoline, pyrazole, pyrazoline, triazole, oxazole, oxazoline, isoxazole, isoxazoline, furazan, or oxadiazole, each of which may be further optionally substituted with one or more substituents selected from alkyl, alkoxy, amine, aminoalkyl, amidoalkyl, halo, hydroxy, trihaloalkyl, trihaloalkoxy or phenyl, wherein the phenyl group may be further optionally substituted with 1 to 3 substituents selected from alkyl, alkoxy, hydroxy, halo, nitro, trihaloalkyl, or trihaloalkoxy.

b) $R^1$ is selected from acyl derivatives of furan, imidazole, pyrazole, pyrazine, pyrazole, triazole, oxazole or isoxazole, each of which may be further substituted with 1 to 3 substituents selected from alkyl, alkoxy, amine, aminoalkyl, amidoalkyl, halo, hydroxy, trihaloalkyl, trihaloalkoxy or phenyl wherein the phenyl group may be further optionally substituted with 1 to 3 substituents selected from alkyl, alkoxy, hydroxy, halo, nitro, trihaloalkyl or trihaloalkoxy.

c) $R^1$ is isoxazolecarbonyl optionally substituted with a group selected from alkyl, alkoxy, amine, aminoalkyl, amidoalkyl, halo, hydroxy, trihaloalkyl, trihaloalkoxy or phenyl, wherein the phenyl group may be further optionally substituted with 1 to 3 substituents selected from alkyl, alkoxy, hydroxy, halo, nitro, trihaloalkyl or trihaloalkoxy.

d) $R^2$ is an aromatic or aliphatic $C_3$-$C_8$cyclic group or $C_3$-$C_8$heterocyclic group comprising 1 to 3 heteroatoms selected from N and O, wherein the $C_3$-$C_8$cyclic group or $C_3$-$C_8$heterocyclic group may be further substituted with one or more substituents selected from alkyl, amine, hydroxy, or the cyclic group or heterocyclic group is fused with an optionally substituted aromatic or aliphatic $C_3$-$C_8$cyclic group or $C_3$-$C_8$heterocyclic group.

e) $R^2$ is selected from cyclohexane or phenyl optionally substituted with one or more substituents selected from alkyl, amine, hydroxy, or the cyclic group or heterocyclic group is fused with an optionally substituted aromatic or aliphatic $C_3$-$C_8$cyclic group or $C_3$-$C_8$heterocyclic group.

f) $R^2$ is selected from cyclohexane, phenyl, (p-methyl)phenyl. (p-amino)phenyl, p-hydroxy)phenyl or indole.

g) $R^3$ is selected from hydrogen or methyl.

h) $R^4$ is hydrogen, $C_1$-$C_6$alkyl, aminoalkyl or amidoalkyl: $R^5$ is a benzyl group, optionally substituted with a group selected from alkyl, aminoalkyl, alkoxy. $C_4$-$C_7$heterocycle, hydroxy, halo, nitro, dioxalane, trihaloalkyl, trihaloalkoxy or —C(O)NHCHR$^9$R$^{10}$, wherein R$^9$ is —C(O)NH$_2$ and R$^{10}$ is a $C_2$-$C_5$-aminoalkyl.

i) $R^4$ is hydrogen, $C_1$-$C_6$alkyl, aminoalkyl or amidoalkyl; $R^5$ is a benzyl group, optionally substituted with a group selected from alkyl, aminoalkyl, alkoxy, arylamine, $C_4$-$C_7$heterocycle, hydroxy, halo, nitro, dioxalane, trihaloalkyl or trihaloalkoxy.

j) $R^4$ is hydrogen; $R^5$ is a benzyl group, substituted with alkyl or alkoxy.

k) $R^4$ is hydrogen; $R^5$ is a benzyl group, substituted with —C(O)NHCHR$^9$R$^{10}$: wherein R$^9$ is —C(O)NH$_2$ and R$^{10}$ is a $C_2$-$C_5$-aminoalkyl.

l) $R^4$ is hydrogen; $R^5$ is a benzyl group, substituted with a group selected from alkyl or alkoxy and the group —C(O)NHCHR$^9$R$^{10}$ wherein R$^9$ is —C(O)NH$_2$ and R$^{10}$ is a $C_2$-$C_5$ aminoalkyl.

m) $R^4$ and $R^5$ combined, together with the nitrogen to which they are attached, form piperidine optionally substituted with a group selected from phenyl, benzyl, aminoalkyl, aminoaryl, amidoalkyl or heterocycle, or piperidine is fused with an aromatic or aliphatic $C_3$-$C_8$cyclic group or $C_3$-$C_8$heterocyclic group; wherein the phenyl, benzyl, aminoaryl, heterocycle or fused aromatic or aliphatic $C_3$-$C_8$cyclic group or $C_3$-$C_8$heterocyclic group may be further substituted with 1 to 3 substituents selected from alkyl, alkylamine, alkylsulfonyl, alkoxy, aminoalkyl, aminoaryl, amidoalkyl, arylamine, hydroxy, halo, nitro, oxo, optionally substituted phenyl, optionally substituted piperidine, dioxalane, trihaloalkyl, or trihaloalkoxy or the fused aromatic or aliphatic $C_3$-$C_8$cyclic group or $C_3$-$C_8$heterocyclic group is fused with an additional $C_6$-$C_{10}$cyclic or $C_6$-$C_{10}$heterocyclic group.

n) $R^6$ is hydrogen or $C_1$-$C_6$alkyl.

o) $R^7$ is $C_1$-$C_6$alkyl, amino, hydroxy, alkoxy, aminoalkyl, amidoalkyl, saturated or unsaturated cycloalkyl, or heterocycle.

In a further embodiment with reference to the general formula (I), one or more of the following preferred embodiments apply:

p) $R^1$ is selected from acyl derivatives of pyrrole, pyridine, pyrazine, furan, benzofuran, benzothiazole, imidazole, imidazoline, pyrazole, pyrazoline, triazole, oxazole, oxazoline, isoxazole, isoxazoline, furazan, or oxadiazole, each of which may be further optionally substituted with 1 to 3 substituents selected from alkyl or phenyl, wherein the phenyl group may be further optionally substituted with 1 to 3 substituents selected from alkyl, alkoxy, hydroxy, halo, nitro, trihaloalkyl, or trihaloalkoxy.

q) $R^1$ is selected from acyl derivatives of furan, imidazole, pyrazole, pyrazine, pyrazole, triazole, oxazole or isoxazole, each of which may be further substituted with 1 to 3 substituents selected from alkyl or phenyl wherein the phenyl group may be further optionally substituted with 1 to 3 substituents selected from alkyl, alkoxy, hydroxy, halo, nitro, trihaloalkyl or trihaloalkoxy.

r) $R^1$ is isoxazolecarbonyl optionally substituted with a group selected from alkyl or phenyl, wherein the phenyl group may be further optionally substituted with 1 to 3 substituents selected from alkyl, alkoxy, hydroxy, halo, nitro, trihaloalkyl or trihaloalkoxy.

s) $R^2$ is cyclohexane.

t) $R^3$ is hydrogen.

u) $R^4$ is hydrogen, $C_1$-$C_6$alkyl, aminoalkyl or amidoalkyl; $R^5$ is a benzyl group, optionally substituted with a group selected from alkyl, alkoxy, arylamine, $C_4$-$C_7$heterocycle, hydroxy, halo, nitro, dioxalane, trihaloalkyl, trihaloalkoxy or —C(O)NHCHR$^9$R$^{10}$, wherein R$^9$ is —C(O)NH$_2$ and R$^{10}$ is a $C_2$-$C_5$aminoalkyl.

v) $R^4$ is hydrogen, $C_1$-$C_6$alkyl, aminoalkyl or amidoalkyl; $R^5$ is a benzyl group, optionally substituted with a group selected from alkyl, aminoalkyl, alkoxy, C $C_7$heterocycle, hydroxy, halo, nitro, dioxalane, trihaloalkyl or trihaloalkoxy.

w) $R^4$ is hydrogen; $R^5$ is a benzyl group, substituted with alkyl or alkoxy.

x) $R^4$ is hydrogen; $R^5$ is a benzyl group, substituted with —C(O)NHCHR$^9$R$^{10}$: wherein $R^9$ is —C(O)NH$_2$ and $R^{10}$ is a C$_2$-C$_5$-aminoalkyl.

y) $R^4$ is hydrogen; $R^5$ is a benzyl group, substituted with a group selected from alkyl or alkoxy and the group —C(O)NHCHR'R$^6$ wherein le is —C(O)NH$_2$ and $R^6$ is a C$_1$-C$_5$aminoalkyl.

z) $R^4$ and $R^5$ combined, together with the nitrogen to which they are attached, form piperidine, optionally substituted with a group selected from phenyl, benzyl, aminoalkyl, amidoalkyl or a heterocycle; wherein the phenyl, benzyl or heterocycle may be further optionally substituted with 1 to 3 substituents selected from alkyl, alkoxy, aminoalkyl, amidoalkyl, hydroxy, halo, nitro, dioxalane, trihaloalkyl or trihaloalkoxy.

aa) $R^6$ is methyl.

ab) $R^7$ is ethyl.

In a further aspect, the present invention provides compounds of the formula (I) represented by the formula (Ia):

(Ia)

wherein $R^{11}$ is a 5- or 6-membered unsaturated heterocyclic ring comprising 1 to 3 heteroatoms selected from N and O, optionally substituted with one or more groups selected from alkyl or phenyl, wherein the phenyl group may be further optionally substituted with 1 to 3 substituents selected from alkyl, alkoxy, hydroxy, halo, nitro, trihaloalkyl or trihaloalkoxy:

$R^4$ is hydrogen, C$_1$-C$_6$alkyl, aminoalkyl or amidoalkyl;

$R^5$ is a benzyl group, optionally substituted with a group selected from alkyl, aminoalkyl, alkoxy, C$_4$-C$_7$heterocycle, hydroxy, halo, nitro, dioxalane, trihaloalkyl, trihaloalkoxy or —C(O)NHCHR$^9$R$^{10}$; wherein $R^9$ is —C(O)NH$_2$ and $R^{10}$ is a C$_2$-C$_5$aminoalkyl;

or $R^4$ and $R^5$ combined, together with the nitrogen to which they are attached, form piperidine, optionally substituted with a group selected from phenyl, benzyl, aminoalkyl, amidoalkyl or a heterocycle; wherein the phenyl, benzyl or heterocycle may be further substituted with 1 to 3 substituents selected from alkyl, alkyloxy, aminoalkyl, amidoalkyl, hydroxy, halo, nitro, dioxalane, trihaloalkyl, or trihaloalkoxy; or a salt thereof.

In a preferred embodiment $R^{11}$ is isoxazole.

Accordingly, in a preferred aspect, the present invention provides compounds of the formula (I) represented by the formula (Ib):

(Ib)

wherein $R^4$ is hydrogen, C$_1$-C$_6$alkyl, aminoalkyl or amidoalkyl:

$R^5$ is a benzyl group, optionally substituted with a group selected from alkyl, aminoalkyl, alkoxy. C$_4$-C$_7$heterocycle, hydroxy, halo, nitro, dioxalane, trihaloalkyl, trihaloalkoxy or —C(O)NHCHR$^9$R$^{10}$; wherein $R^9$ is —C(O)NH$_2$ and $R^{10}$ is a C$_2$-C$_5$aminoalkyl;

or $R^4$ and $R^3$, $R^5$ combined, together with the nitrogen to which they are attached, form piperidine, optionally substituted with a group selected from phenyl, benzyl, aminoalkyl, aminoaryl, amidoalkyl or a heterocycle, or piperidine is fused with an aromatic or aliphatic C$_3$-C$_8$cyclic group or C$_3$-C$_8$heterocyclic group; wherein the phenyl, benzyl, heterocycle or fused aromatic or aliphatic C$_3$-C$_8$cyclic group or C$_3$-C$_8$heterocyclic group may be further substituted with 1 to 3 substituents selected from alkyl, alkylamine, alkylamide, alkyloxy, aminoalkyl, amidoalkyl, hydroxy, halo, nitro, dioxalane, trihaloalkyl, or trihaloalkyloxy: or a salt thereof.

In a further preferred embodiment and with reference to compounds of the formula (1). $R^{11}$ is isoxazole. $R^4$ is hydrogen and $R^5$ is an optionally substituted benzyl group.

Accordingly, in a further aspect, the present invention provides compounds according to the formula (I) represented by the formula (Ic):

(Ic)

wherein $R^a$, $R^b$ and $R^c$ individually represent a group selected from hydrogen, alkyl, aminoalkyl, alkoxy, C$_4$-C$_7$heterocycle, hydroxy, halo, nitro, trihaloalkyl, trihaloalkoxy or —C(O)NHCHR$^9$R$^{10}$; wherein $R^9$ is —C(O)NH$_2$ and $R^{10}$ is a C$_2$-C$_5$aminoalkyl;

or $R^a$ and $R^b$ or $R^b$ and $R^c$ combined form dioxalane; or a salt thereof.

In a preferred embodiment with respect to formula (Ic), $R^a$ and $R^c$ are hydrogen and $R^b$ is —C(O)NHCHR$^9$R$^{10}$ wherein R$^9$ is —C(O)NH$_2$ and R$^{10}$ is a C$_2$-C$_5$aminoalkyl.

In another preferred embodiment with respect to formula (Ic), one of $R^a$ or $R^b$ is methyl, methoxy or ethoxy, and the other is hydrogen and $R^e$ is hydrogen.

In a further preferred embodiment with respect to formula (Ic), $R^a$ and $R^b$ or $R^B$ and $R^c$ combined form dioxalane, and the remaining $R^c$ or $R^a$ is hydrogen.

In another further preferred embodiment and with reference to compounds of the formula (I), R$^{11}$ is isoxazole and R$^4$ and R$^5$ combined, together with the nitrogen to which they are attached form piperidine, optionally substituted with a group selected from phenyl, benzyl, aminoalkyl, amidoalkyl, aminoaryl or a heterocycle: wherein the phenyl, benzyl or heterocycle may be further substituted with 1 to 3 substituents selected from alkyl, alkoxy, aminoalkyl, amidoalkyl, hydroxy, halo, nitro, dioxalane, trihaloalkyl, or trihaloalkoxy.

Accordingly, in another aspect, the present invention provides compounds according to the formula (I), represented by the formula (Id):

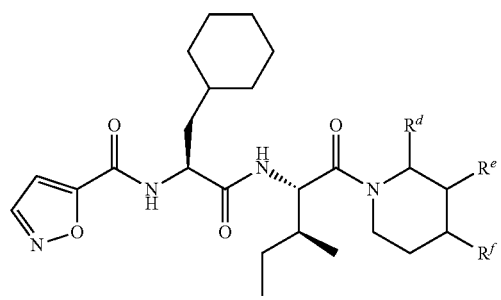

(Id)

wherein $R^d$, $R^e$ and $R^f$ independently represent a group selected from phenyl, benzyl, aminoalkyl, amidoalkyl, aminoaryl or a heterocycle, or $R^d$ and $R^e$ or $R^e$ and $R^f$ combined, form a fused aromatic or aliphatic C$_3$-C$_8$cyclic group or C$_3$-C$_8$heterocyclic group; wherein the phenyl, benzyl, heterocycle or fused aromatic or aliphatic C$_3$-C$_8$cyclic group or C$_3$-C$_8$heterocyclic group may be further substituted with 1 to 3 substituents selected from alkyl, alkoxy, aminoalkyl, amidoalkyl, hydroxy, halo, nitro, dioxalane, trihaloalkyl, or trihaloalkoxy; or salts thereof.

In yet further preferred embodiments, compounds of the formula (I) are selected from the group consisting of:
5-isoxazoyl-Cha-Ile-aminomethylphenyl:
5-isoxazoyl-Cha-Ile-aminomethyl-(2-methoxy)phenyl;
5-isoxazoyl-Cha-Ile-aminomethyl-(3-methoxy)phenyl;
5-isoxazoyl-Cha-Ile-aminomethyl-(4-methoxy)phenyl;
5-isoxazoyl-Cha-Ile-aminomethyl-(2-methyl)phenyl;
5-isoxazoyl-Cha-Ile-aminomethyl-(2-ethoxy)phenyl;
5-isoxazoyl-Cha-Ile-aminomethyl-(2-propoxy)phenyl;
5-isoxazoyl-Cha-Ile-aminomethyl-(2-isopropoxy)phenyl;
5-isoxazoyl-Cha-Ile-aminomethyl-(2-butoxy)phenyl;
5-isoxazoyl-Cha-Ile-aminomethyl-(2-isobutoxy)phenyl;
5-isoxazoyl-Cha-Ile-aminomethyl-(2-chloro)phenyl;
5-isoxazoyl-Cha-Ile-aminomethyl-(2-nitro)phenyl;
5-isoxazoyl-Cha-Ile-aminomethyl-(2-trifluoromethyl)phenyl;
5-isoxazoyl-Cha-Ile-aminomethyl-(3-trifluoromethoxy)phenyl;
5-isoxazoyl-Cha-Ile-aminomethyl-(2-trifluoromethyl)phenyl;
5-isoxazoyl-Cha-Ile-aminomethyl-(2-fluoro)phenyl
5-isoxazoyl-Cha-Ile-aminomethyl-(3-fluoro)phenyl;
5-isoxazoyl-Cha-Ile-aminomethyl-(4-fluoro)phenyl;
5-isoxazoy 1-Cha-Ile-aminomethyl-(1,3-dioxalane)phenyl;
5-isoxazoyl-Cha-Ile-aminomethyl-(3,4-dichloro)phenyl;
5-isoxazoyl-Cha-Ile-aminomethyl-(2,4-dimethoxy)phenyl;
5-isoxazoyl-Cha-Ile-aminomethyl-(2,5-dimethoxy)phenyl;
5-isoxazoyl-Cha-Ile-aminomethyl-(3,4-dimethoxy)phenyl;
5-isoxazoyl-Cha-Ile-aminomethyl-(2,3-dimethoxy)phenyl;
5-isoxazoyl-Cha-Ile-aminomethyl-(2,3,4-dimethoxy)phenyl;
5-isoxazoyl-Cha-Ile-aminomethyl-(2,6-dimethoxy)phenyl;
5-isoxazoyl-Cha-Ile-aminomethyl-(2-methoxy-5-trifluoromethoxy)phenyl;
5-isoxazoyl-Cha-Ile-aminomethyl-(2,4-dimethoxy)phenyl;
5-isoxazoyl-Cha-Ile-aminomethyl-(3,5-bis(trifluoromethyl))phenyl;
5-isoxazoyl-Cha-Ile-aminomethyl-(2-fluoro)phenyl;
5-isoxazoyl-Cha-Ile-aminomethyl-(3-fluoro)phenyl;
5-isoxazoyl-Cha-Ile-aminomethyl-(4-fluoro)phenyl;
5-isoxazoyl-Cha-Ile-aminomethyl-(1,3-dioxalanc)phenyl;
5-isoxazoyl-Cha-Ile-aminomethyl-(3,4-dichloro)phenyl;
5-isoxazoyl-Cha-Ile-(4-phenyl)piperidine:
5-isoxazoyl-Cha-Ile-4-(p-methoxy)phenyl piperidine;
5-isoxazoyl-Cha-Ile-4-(p-chloro)phenyl piperidine;
5-isoxazoyl-Cha-Ile-4-(o-tri fluoromethyl)phenyl piperidine;
5-isoxazoyl-Cha-Ile-4-(o-phenyl)phenyl piperidine;
5-isoxazoyl-Cha-Ile-4-(m-phenyl)phenyl piperidine;
5-isoxazoyl-Cha-Ile-4-(p-phenyl)phenyl piperidine:
5-isoxazoyl-Cha-Ile-4-(p-phenoxy)phenyl piperidine;
5-isoxazoyl-Cha-Ile-4-(2,5-dimethoxy)phenyl piperidine;
5-isoxazoyl-Cha-Ile-(4-benzyl)piperidine;
5-isoxazoyl-Cha-Ile-2S-(tert-butylamide)piperidine;
5-isoxazoyl-Cha-Ile-4-(4-acetamide)phenyl piperidine;
5-isoxazoyl-Cha-Ile-3-(o-fluoro)aminophenyl piperidine;
5-isoxazoyl-Cha-Ile-3-(m-fluoro)aminophenyl piperidine;
5-isoxazoyl-Cha-Ile-3-(p-fluoro)aminophenyl piperidine;
5-isoxazoyl-Cha-Ile-3-(o-trifluoromethyl)aminophenyl piperidine;
5-isoxazoyl-Cha-Ile-3-(m-trifluoromethyl)aminophenyl piperidine;
5-isoxazoyl-Cha-Ile-3-(p-trifluoromethyl)aminophenyl piperidine;
5-isoxazoyl-Cha-Ile-spirochroman-2,4'-piperidine;
5-isoxazoyl-Cha-Ile-[(S)—N-(tert-butyl)]pipiperidine;
5-isoxazoyl-Cha-Ile-aminodimethyl-(2-methoxy)phenyl;
5-isoxazoyl-Cha-Ile-(3-[aminomethyl]phenyl)-amino-4-aminobutane-1-carboxamide;
5-isoxazoyl-Cha-Ile-(3-[aminomethyl]phenyl)-amino-3-aminopropane-1-carboxamide: or
5-isoxazoyl-Cha-Ile-4-(p-fluorophenyl)piperazine.

In still further preferred embodiments, compounds of the formula (I) are selected from the group consisting of:
5-isoxazoyl-Cha-Ile-aminomethyl-benzimidazole;
5-isoxazoyl-Cha-Ile-aminomethyl-2-biphenyl;
5-isoxazoyl-Cha-Ile-aminomethyl-3-biphenyl;
5-isoxazoyl-Cha-Ile-aminomethyl-4-biphenyl;
5-isoxazoyl-Cha-Ile-aminomethyl-2-napthalene;
5-isoxazoyl-Cha-Ile-(6,7-dimethoxy-1,2,3,4-tetrahydroisoquinoline);
5-isoxazoyl-Cha-Thr(Me)-aminomethyl-(2-methoxy)phenyl;

Cha-Ile-spiro[indene-1,4'-piperidine];
5-isoxazoyl-Cha-Thr(Me)-spiro[indene-1,4'-piperidine];
5-(3-amino-isoxazoyl)-Cha-Ile-spiro[indene-1,4'-piperidine];
5-isoxazoyl-Cha-Thr(Me)-spiro[indene-1,4'-piperidine];
5-isoxazoyl-Cha-Ile-{1-(methylsulfonyl)spiro[indoline-3,4'-piperidine]};
5-isoxazoyl-Cha-Ile-{3H-3-oxo-spiro[isobenzofuran-1,4'-piperidine]};
5-isoxazoyl-Cha-Ile-(4-oxo-spiro[chroman-2,4'-piperidine]); or
5-isoxazoyl-Cha-Ile-spiro[chroman-2,4'-piperidine].

It will be appreciated that compounds of the formula (I) possess at least two asymmetric centres and are therefore capable of existing in more than one stereoisomeric form. It is highly desirable that compounds of the present invention exist as single diastereomers wherein the asymmetric carbon atoms of the cyclohexylalanine and isoleucine residues are of the L-configuration. The invention thus also relates to compounds in substantially pure stereoisomeric form with respect to at least the two asymmetric centres of the cyclohexylalanine and isoleucine residues, e.g., greater than about 90% de, such as about 95% to 97% de or greater than 99% de, as well as mixtures, including racemic mixtures, thereof. Such diastereomers may be prepared by asymmetric synthesis, for example usinp, chiral intermediates, or mixtures may be resolved by conventional methods. e.g. chromatography, or use of a resolving agent.

Additionally, formula (I) is intended to cover, where applicable, solvated as well as unsolvated forms of the compounds. Thus, each formula includes compounds having the indicated structure, including the hydrated as well as the non-hydrated Corms.

It will be appreciated that the compounds of the invention may exist as salts. The novel bioactive compounds of the invention can be administered to a subject as a pharmaceutically acceptable salt. It will be appreciated however that non-pharmaceutically acceptable salts also fall within the scope of the present invention since these may be useful as intermediates in the preparation of pharmaceutically acceptable salts or as tools for biological studies.

The term "pharmaceutically acceptable" as applied to salts of the present invention and/or used in methods of the present invention refers to salts which are, within the scope of sound medical judgment, suitable for use in contact with the tissues of humans and lower animals without undue toxicity, irritation, allergic, or a like negative response that exceeds a reasonable risk/therapeutic benefit ratio. Preferably, a pharmaceutically acceptable salt is a salt that is suitable for administration to a patient. Accordingly, the present invention also extends to a pharmaceutically acceptable salt of any one of the compounds of the present invention.

Pharmaceutically acceptable salts are generally known in the art, and in the case of the present invention, include relatively non-toxic, organic or inorganic salts of the compounds of the present invention. Examples of such salts include, but are not limited to, acid addition salts such as hydrochloride salts, sulfate salts, bisulfate salts, borate salts, nitrate salts, acetate salts, phosphate salts, hydrobromide salts, laurylsullonate salts, glucoheptonate salts, oxalate salts, oleate salts, laurate salts, stearate salts, palmitate salts, valerate salts, benzoate salts, naphthylate salts, mesylate salts, tosylate salts, citrate salts, lactate salts, maleate salts, succinate salts, tartrate salts, fumarate salts, and the like (see, for example, Berge et al. J. Pharm. Sci. 1977, 66, 1-19). In addition, pharmaceutically acceptable salts also include basic salts such as alkali metal salts, alkaline earth salts, and ammonium salts. For example, pharmaceutically acceptable basic salts include salts of aluminium, calcium, lithium, magnesium, potassium, sodium, zinc, and the like. In addition, organic salts may also be used including. e.g. salts of lysine. N,N'-dibenzylethylenediamine, chloroprocaine, choline, diethanolamine, ethylenediamine, meglumine (N-methylglucamine), procaine and tris. The basic nitrogen-containing groups in the compounds of the present invention can be quaternized with various organic agents including, e.g., alkyl halides (such as lower alkyl halide including methyl, ethyl, propyl, and butyl chlorides, bromides and iodides), long chain halides (e.g. decyl, lauryl, myristyl and stearyl chlorides, bromides and iodides), aralkyl halides (e.g., benzyl and phenethyl bromides), dialkyl sulfates (e.g., dimethyl, diethyl, dibutyl and diamyl sulfates).

The salts of the compounds of the present invention also can exist in the form of solvates, e.g. with water, methanol, ethanol, dimethylformamide, ethyl acetate, and the like, and mixtures thereof.

Prodrug derivatives are also included in the scope of the present invention, and in the broadest sense, encompass compounds that are converted in vivo to a compound of the present invention. Such derivatives would readily occur to one skilled in the art and include compounds that are further modified with, for example, alkyl or acyl groups, oxides, sugars or oligopeptides, which are rapidly cleaved in the body to give the active compounds according to the invention. That is, the term "prodrug" refers to a precursor or modified compound of the present invention that is not fully active or available until converted in vivo to its therapeutically active or available form.

Processes for preparing the compounds of the present invention are provided as further embodiments of the invention and are illustrated by the following general procedures.

Compounds may be synthesized using protected amino acids. Amino protecting groups are generally known to those skilled in the art and relate to groups which are suitable for protecting (or blocking) an amino group from chemical reactions, but which are easily removable after the desired chemical reaction has been carried out at other positions in the molecule. Since the protective groups are removed after the desired reaction (or reaction sequence), their nature and size is otherwise uncritical. Examples of amino protecting groups include, but are not limited to acyl protecting groups such as acetyl, propionyl, butyryl, phenylacetyl, benzoyl or toluoyl groups; aryloxy-alkanoyl protecting groups: alkoxycarbonyl protecting groups such as methoxycarbonyl, ethoxycarbonyl. 2,2,2-trichloroethoxycarbonyl, tert-butyldicarbonyl (Boc), 2-iodoethoxycarhonyl: aralkoxycarbonyl protecting groups such as carbobenzyloxy (Cbz), 4-methoxy-benzyloxycarbonyl, fluorenylmethyloxycarbonyl chloride (Fmoc): or arylsulfonyl protecting groups such as 4-methoxy-2,3,6-trimethylphenylsulfonyl (Mtr), pentamethyl-2,3-dihydrobenzofuran-5-sulfonyl (Pbf) or 2,2,5,7,8-pentamethylchroman-6-sulfonlyl (Pmc). Preferred amino protecting groups are Boc, Cbz, Fmoc, and benzyl. The more preferred amino acid protecting group is Boc.

Generally, compounds are synthesised in solution phase wherein the Boc-protected isoleucine residue, one or more coupling or activating reagents and a base such as N,N-diisopropylethylamine (DIPEA) are dissolved in a suitable volume of solvent.

Coupling reagents used to activate a carboxyl group in order to progress the coupling of the carboxyl group to an amino group are generally well known to those skilled in the art and may include carbodiimide coupling reagents such as dicyclohexylcarbodiimide (DCC) and diisopropylcarbodiimide (DIC) as well as triazole coupling reagents such as 1-hydroxy-benzotriazole (HOBt), 1-hydroxy-7-aza-benzotriazole (HOAt), benzotriazole-1-yl-oxy-tris-(dimethylamino)-phosphonium hexafluorophosphate (BOP), benzotriazol-1-yl-oxytripyrrolidinophosphonium hexafluorophosphate (PyBOP), 2-(1H-7-azahenzotriazol-1-yl)1,1,3,3-tetramethyluronium hexafluorophosphate methanaminium (HATU), 2-(1H-6-benzotriazol-1-yl)1,1,3,3-tetramethyluronium hexafluorophosphate (HBTU) and O-(1H-6-chlorobenzotriazole-1-yl)1,1,3,3-tetramethyluronium hexafluorophosphate (HCTU).

Generally, the above reaction may be performed in any solvent or mixture of solvents suitable for solution phase peptide synthesis including, but not limited to dimethylformamide (DMF), N-methylpyrrolidine (NMP), trifluoroethanol (TFE), hexafluoroisopropanol (HFIP), dichloromethanol (DCM), or chloroform. In a preferred embodiment, the reaction is performed in DMF.

The solution is then added to an amino bearing C-terminal moiety, represented by the substituents $R^2$ and $R^3$ for compounds of the formula (I), and left to stir until the reaction reaches completion. Generally, the reaction is performed at room temperature. Completion of the coupling reaction is determined by electrospray ionisation mass spectroscopy (ESI MS) or other forms of spectrometry.

The intermediate compound is then isolated from the reaction mixture and the crude product is treated with a solution of trifluoroacetic acid (TFA) in DCM to remove the isoleucine N-terminal Boc-protecting group. The solution is then evaporated under $N_2$, washed, filtered and evaporated under reduced pressure. Subsequent amino acids and N-terminal carboxylic acids are then sequentially coupled under the same conditions. The final crude products are purified by reverse phase high performance liquid chromatography (rpHPLC). The compounds of the present invention are characterized by high-resolution mass spectroscopy (HRMS) and proton nuclear magnetic resonance spectroscopy ($^1$H NMR) and purity of the compounds is assessed via analytical reversed phase HPLC.

The compounds of the present invention have been identified by their ability to modulate PAR2 activity, either by activating the receptor or by inhibiting the activity of the native tethered ligand and as such, may be referred to herein as "agonists", "antagonists", "inhibitors", 'PAR2 inhibitors", "inhibitors of PAR2", and the like. It is important to note that PAR2 antagonists in a particular cell type or assayed in a particular way may be PAR2 agonists or partial agonists in a different cell type or assayed in a different way, and vice versa. For example, compounds that activate the release of intracellular calcium from one type of cell are agonists or partial agonists, while those that inhibit such release may be antagonists. However these "agonist" and "antagonist" effects may be reversed for a given compound or PAR2 ligand in a different cell, or opposite responses may be observed using a different reported assay (e.g. IRK phosphorylation or cAMP stimulation).

The term "ligand" refers to a specific binding partner of a receptor and includes, without limitation, the native tethered PAR2 ligand as well as unbound endogenous, extracellular ligands such as receptor agonists, partial agonists, mixed agonists, antagonists and drugs. The term "receptor" refers to a specific binding partner of a ligand and includes, without limitation, membrane bound receptors.

The ability of the compounds of the present invention to modulate PAR2 can be assessed by any number of means available to the skilled addressee, for example, in vitro assays measuring the effect of PAR2 modulation on a number of downstream markers including intracellular calcium mobilisation, intracellular cyclic adenosine monophosphate (cAMP) stimulation or ERK1/2 phosphorylation, such as those methods described in the Examples.

Preferably, and without being limited by theory, the compounds of the present invention inhibit or amplify the activation of PAR2 by binding to the receptor and either preventing the native tethered ligand from contacting the receptor binding region or competing with the tethered ligand or binding elsewhere in the receptor to induce an agonist of antagonist activity. Antagonists of PAR2 may also act by inhibiting the activity of other ligands toward PAR2, including, but not limited to, unbound endogenous ligands and synthetic agonists as described herein.

Also preferable are compounds of the present invention that hind to and activate PAR2 in the absence of serine proteases.

In one aspect of the present invention, there is provided a method of modulating the activity of PAR2, comprising exposing the cell to a compound, or a salt thereof. The exposing of the cell to the compound, or a salt thereof, may occur in vitro, ex vivo or in vivo.

Where the exposing of a cell to the compound occurs in vitro or ex vivo, for example, the method of the present invention may be used as a tool for biological studies or as a diagnostic tool to determine the efficacy of certain compounds (alone or in combination) for modulating PAR2 activity in a subject. For example, a cell that expresses PAR2 may be removed from a subject and exposed to one or more compounds of the present invention, or salts thereof. The ability of the compound (or compounds) to modulate the activity of PAR2 can be assessed by measuring any one of a number of down stream markers via a method known to one skilled in the art. Thus, one may be able to ascertain whether a certain compound is more efficacious than another and tailor a specific treatment regime to that subject.

In a preferred embodiment, the exposing of the cell to the compound, or a salt thereof, is in vivo.

In one embodiment of the present invention there is provided a prophylactic or therapeutic method of treating a subject at risk of or susceptible to a disease or disorder, or having a disease or disorder, associated with aberrant PAR2 expression and/or activity. Specific diseases and disorders include, but are not limited to, acute and chronic inflammatory disorders such as arthritis disorders, inflammatory bowel diseases, pancreatitis, cardiovascular disease, gastric ulcer, colitis, asthma, fibrosis and fibrotic disorders, and other conditions associated with inflammatory conditions such as epilepsy, Alzheimer's disease, Parkinson's disease, obesity and type II diabetes, as well as proliferative disorders such as cancers of the stomach, colon, bowel, breast or pancreas.

In a preferred embodiment, the prophylactic or therapeutic method comprises the steps of administering a compound according to the present invention, or a pharmaceutically acceptable salt thereof, to a subject who has a disease or disorder, a symptom of disease or disorder, or predisposition toward a disease or disorder associated with undesired or insufficient PAR2 activity as herein described, for the purpose to cure, heal, alleviate, relieve, alter, remedy, ameliorate, improve, or affect the disease or disorder, the symptoms of the disease or disorder, or the predisposition towards the disease or disorder. The prophylactic treatment may reduce the incidence of diseases or disorders associated with undesirable or insufficient PAR2 activity.

The prophylactic or therapeutic methods of the present invention may also comprise the administering of a combination of the compounds according to the present invention, or pharmaceutically acceptable salts thereof, to a subject who has a disease or disorder, a symptom of disease or disorder, or predisposition toward a disease or disorder associated with undesired PAR2 activity as herein described, for the purpose to cure, heal alleviate, relieve, alter, remedy, ameliorate, improve, or affect the disease or disorder, the symptoms of the disease or disorder, or the predisposition towards the disease or disorder. The prophylactic treatment may reduce the incidence of diseases or disorders associated with undesirable PAR2 activity. In some embodiments, combinations of compounds of the present invention or pharmaceutically acceptable salts thereof may provide enhanced inhibition of PAR2 activity in comparison to prophylactic or therapeutic methods that utilise only one of the compounds of the present invention or pharmaceutically acceptable salts thereof.

It would also be appreciated by one skilled in the art that the prophylactic or therapeutic methods as herein described could be used in any number of combinations with other treatment modalities currently employed in the art.

Conditions in which PAR2 expression and/or activity is increased or decreased, and where it is desirable to reduce or increase said activity, may be identified by those skilled in the art by any or a combination of diagnostic or prognostic assays known in the art. For example, a biological sample obtained from a subject (e.g. blood, serum, plasma, urine, saliva, cerebrospinal fluid, adipose tissue, brain tissue and/or cells derived there from) may be analysed for PAR2 expression and/or activity. Such conditions include, but are not limited to, autoimmune or inflammatory disorders such as arthritis, colitis and inflammatory bowel diseases, pancreatitis, diseases of the liver, kidney and genitourinary system, cardiovascular diseases, stroke, gastric ulcer, asthma, fibrosis and fibrotic disorders, other conditions associated with inflammatory conditions such as epilepsy, Alzheimer's disease, Parkinson's disease, obesity and type II diabetes, metabolic disorders, digestive disorders, neurodegenerative and respiratory diseases, diseases of the skin and subcutaneous tissue, diseases of muscles, bones and tendons, as well as proliferative disorders such as cancers including those of the stomach, colon, bowel, breast or pancreas.

It is considered that the above methods are suitable for the prophylactic and therapeutic treatment of any species, including, but not limited to, all mammals including humans, canines, felines, cattle, horses, pigs, sheep, rats and mice, as well as chickens, birds, reptiles and lower organisms such as bacteria.

In another aspect of the present invention, there is provided a pharmaceutical composition including a compound of the present invention, or a salt thereof (also referred to herein as an "active compound"). In a preferred embodiment, the pharmaceutical composition may comprise a pharmaceutically acceptable carrier, excipient, diluent and/or adjuvant.

Pharmaceutical compositions of the present invention may be employed alone or in conjunction with other compounds, such as therapeutic compounds.

As used herein, the term "pharmaceutically acceptable carrier" preferably includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is generally formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate: chelating agents such as ethylenediaminetetraacetic acid: buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor m (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, or liquid polyetheylene glycol, and the like), and suitable mixtures thereof. The proper fluidity can be maintained, for example, by the use of a coating such as lecithin, by the maintenance of the required particle size in the case of a dispersion or by the use of surfactants. Prevention of the action of microorganisms can be achieved by incorporation of various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, or sorbitol, or sodium chloride in the composition. Prolonged absorption of the injectable compositions can be brought about by including in the composition an agent which delays absorption, for example, aluminium monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yield a powder of the active ingredient plus any additional desired ingredient from a previously sterile-filtered solution thereof.

Oral compositions generally comprise an inert diluent or an edible carrier. For the purpose of oral therapeutic administration, the active compound can be incorporated with excipients and used in the form of syrups, tablets, troches, or capsules, e.g. gelatin capsules. Oral compositions can also be prepared using a fluid carrier such as olive or other oils, or fluids for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin: or a flavouring agent such as peppermint, methyl salicylate, or orange flavouring.

For administration by inhalation, the compounds are delivered in the form of an aerosol spray from a pressurised container or dispenser that contains a suitable propellant, e.g. a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished with nasal sprays or suppositories. The compounds can be prepared in the form of suppositories (e.g., with conventional suppository bases such as cocoa butter and other glycerides) or retention enemas for rectal delivery.

For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals. Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for case of administration and uniformity of dosage. "Dosage unit form" as used herein preferably refers to physically discrete units suited as unitary dosages for the subject to be treated: each unit containing a predetermined quantity of active compound calculated to produce the desired therapeutic effect in association with the required pharmaceutical carrier.

The pharmaceutical compositions according to the present invention can be included in a container, pack, or dispenser together with instructions for administration.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosages for use in humans. The dosage lies preferably within a range of circulating concentrations that include the $LD_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The skilled artisan will appreciate that certain factors may influence the dosage and timing required to effectively treat a subject, including the activity of the specific compound employed, the age, body weight, general health, gender, and diet of the subject, the time of administration, the route of administration, the rate of excretion, any drug combination, the degree of expression or activity to be modulated, the severity of the disease or disorder, previous treatments and other diseases present.

For the above mentioned indications, the appropriate dosage will vary depending on, e.g. the compound employed, the age, sex, weight and general physical condition of the subject, the mode of administration, the nature and/or severity of the condition or the desired effect. By balancing these features it is well within the general skill of a medical practitioner to determine appropriate dosages. By way of example, however, suitable daily dosages are in the range of from about 0.1 to about 2000 mg/kg, preferably from about 0.2 to about 100 mg/kg, more preferably from about 0.5 to about 200 mg/kg, even more preferably from about 1 to about 50 mg/kg of body weight.

Examples of the procedures used in the present invention will now be more fully described. It should be understood, however, that the following description is illustrative only and should not be taken in any way as a restriction on the generality of the invention described above.

EXAMPLES

Methods for Preparing Compounds of the General Formula (I)

The following examples are representative of the present invention, and provide detailed methods for preparing exemplary compounds of the present invention.

General Amino Acid Coupling Procedure (A):

Compounds can be synthesized in solution phase using, for example, Fmoc or floc-protected amino acids. In one example, Boc-protected isoleucine (1.2-1.5 eq) was activated with HBTU or BOP (1.5 eq) and DIPEA (1.5 eq) in DMF (0.2-0.5 M) for 10 minutes. The solution was then added to free amine and the mixture was stirred until the reaction reached completion. The reaction mixture was diluted with EtOAc and washed with saturated $NaHCO_3$ (×2). The organic layers were dried over $MgSO_4$, and evaporated in vacuo. The crude was then treated with 20% TFA in DCM and stirred for 1-2 h to remove Boc-protecting group. The TFA was removed by evaporating the reaction mixture under $N_2$. The residue was dissolved in DCM and washed with saturated $NaHCO_3$ (×2), dried with $MgSO_4$, filtered and evaporated in vacuo. The Boc-protected cyclohexylalanine amino acid (Boc-Cha-OH) and optionally substituted heterocycle carboxylic acids were then sequentially coupled under the same conditions. Each coupling reaction was monitored by ESI MS, with most reactions reaching completion overnight.

General HPLC Purification and Analysis Methods:

All crude products were purified via semipreparative rpI-PLC fitted with a tunable absorbance detector (λ 214 nM), using a Phenomenex C18 column (300 Å, 21.2×250 mm). The purified compounds were characterized by HRMS and $^1$H NMR (400 MHz or 600 MHz), and the purities were assessed via analytical rpHPLC (Phenomenex C18 column, 300, 4.6×250 mm, λ 214, 230 and 254 nm). All compounds were >95% pure.

Analytical rpHPLC methods: 50-100% B in 10 min, 100% B for further 10 min

Solvent A: 0.1% TEA in $H_2O$, solvent B: 0.1% TEA in 10% $H_2O$, 90% acetonitrile (for semipreparative and analytical rpHPLC)

High-resolution electrospray ionisation mass spectroscopy (HRMS) measurements were obtained on a Bruker micrOTOF mass spectrometer equipped with a Dionex LC system (Chromeleon) in positive ion mode by direct infusion in MeCN at 100 μL/h using sodium formate clusters as an internal calibrant. Data was processed using Bruker Daltonics Data Analysis 3.4 software. Mass accuracy was better than 1 ppm error.

Example 1

Preparation of 5-isoxazoyl-Cha-Ile-aminomethyl-(2-fluoro)phenyl (6)

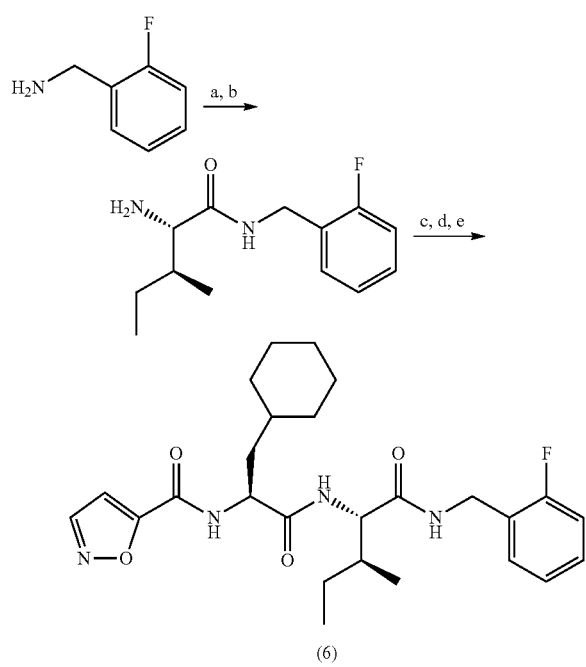

a Boc-Ile-OH, HBTU/DIPEA in DMF;
b 20% TFA in DCM;
c Boc-Cha-OH, HBTU/DIPEA in DMF;
d 20% TFA in DCM;
e Isoxazole 5-carboxylic acid, HBTU/DIPEA in DMF Compound 6 was synthesised by following the general amino acid coupling procedure A.

$^1$H NMR (400 MHz, CDCl$_3$): δ 0.79-0.86 (m, 8 H), 0.88-0.98 (m, 1 H), 1.01-1.23 (m, 5 H), 1.27-1.37 (m, 1 H), 1.39-1.49 (m, 1 H), 1.63-1.77 (H's overlap with $H_2O$ peak), 1.81-1.88 (m, 1H), 4.40-4.45 (dd, 1 H, J=5.6, 14.8 Hz), 4.51-4.57 (dd, 1 H, J=6.0, 14.81 Hz), 4.70-4.76 (m, 1 H), 6.63 (br s, 1 H), 6.87-6.89 (br s, 1 H), 6.91-6.92 (d, 1 H, J=2 Hz), 7.00-7.10 (m, 2 H), 7.22-7.36 (m, 3 H), 8.30-8.31 (d, 1 H, J=1.6 Hz).

HRMS: [MH]$^+$ 487.2715 (calc. for $C_{26}H_{36}FN_4O_4{}^+$) 487.2718 (found).

Example 2

Preparation of 5-isoxazoyl-Cha-Ile-aminomethyl-(2-methoxy)phenyl (18)

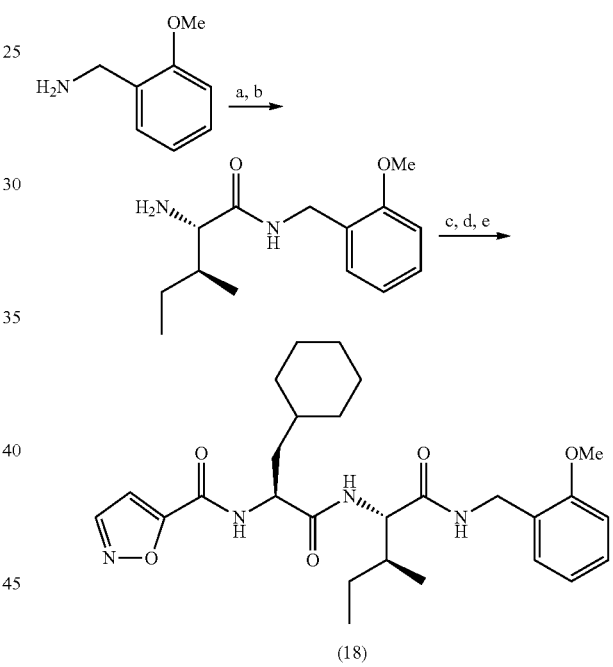

a Boc-Ile-OH, HBTU/DIPEA in DMF;
b 20% TFA in DCM;
c Boc-Cha-OH, HBTU/DIPEA in DMF;
d 20% TFA in DCM;
e Isoxazole 5-carboxylic acid, HBTU/DIPEA in DMF.

Compound 18 was synthesised by following the general amino acid coupling procedure A.

$^1$H NMR (400 MHz, CDCl$_3$): δ 0.82-0.86 (m, 7 H), 0.88-1.00 (m, 2 H), 1.04-1.22 (m, 1 H), 1.25-1.37 (m, 2 H), 1.40-1.46 (m, 1 H), 1.59-1.73 (m, 7 H), 1.77-1.84 (m, 2 H), 3.86 (s, 3 H), 4.19-4.23 (dd, 1 H, =6.8, 8.8 Hz), 4.37-4.42 (dd, 1 H, J=6, 14.4 Hz), 4.46-4.51 (dd, 1 H, J=6, 14.4 Hz), 4.60-4.65 (m, 1 H), 6.19-6.21 (t, 1 H, J=5.6 Hz), 6.50-6.53 (d, 1 H, J=8.8 Hz), 6.87-6.93 (m, 3 H), 6.99-7.01 (d, 1 H, J=7.2 Hz), 7.23-7.29 (m, 2 H), 8.331-8.335 (d, 1 H, J=1.6 Hz).

HRMS: [MH]$^+$ 499.2915 (calc. for $C_{27}H_{39}N_4O_5{}^+$) 499.2915 (found)

Example 3

Preparation of 5-isoxazoyl-Cha-Ile-aminomethyl-(2-isopropoxy)phenyl (24)

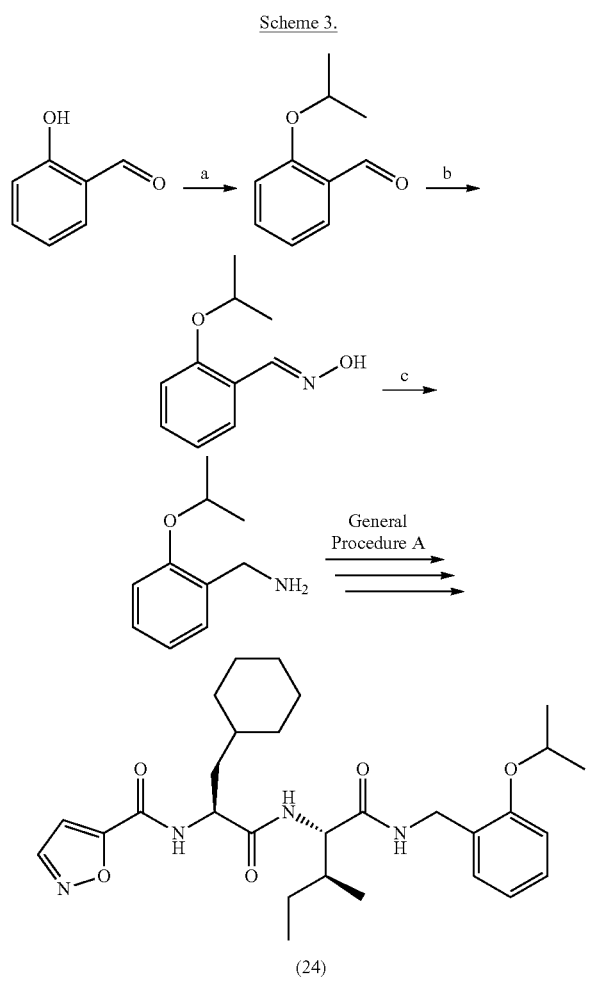

a 2-iodopropane, DBU, 140° C.;
b NH₂OH;
c Zn, HCOONH₄

Step a: In a microwave reaction vial was loaded salicylaldehyde (1 eq), DMF, DBU (1 eq) and the corresponding 2-iodopropane. The vessel was sealed and the mixture was irradiated in Biotage Initiator microwave reactor (140° C., 10 min). The progress of the reaction was monitored by TLC (PE/EtOAc 4:1, product Rf ~0.5). Upon completion, the reaction mixture was allowed to cool down, diluted with EtOAc and washed with sat. Na₂CO₃ (3×) to remove starting material salicylaldehyde. The organic phase was dried over MgSO₄, filtered and evaporated to dryness to the give product as a yellow liquid (70% yield), which was used without further purification.

Step b: The resulting aldehyde was treated with hydroxylamine hydrochloride (2 eq.) and NaOH (4 eq.) in MeOH/H₂O (1:1) and stirred at room temperature for an hour. After completion, the reaction solution was evaporated to dryness and then re-dissolved in EtOAc, washed with 1 M HCl (2×), sat. NaHCO₃ (2×) and brine (1×). The organic phase was dried over MgSO₄, filtered and evaporated to dryness to give a waxy solid (90% yield).

Step c: To starting material oxime in MeOH, ammonium formate (2 eq.) and zinc dust (2 eq.) were added and the reaction mixture was refluxed for an hour. The reaction mixture was filtered through a pad of celite, washed with MeOH and the filtrate was evaporated. The impure crude was purified on preparative HPLC. The purified amine was coupled to Boc-protected isoleucine as described in the general amino acid coupling procedure A to give 24.

$^1$H NMR (600 MHz, CDCl₃), δ 0.81-0.87 (m, 6H), 0.87-1.01 (m, 2H), 1.06-1.34 (m, 6H), 1.36-1.38 (t, 6H, J=6 Hz), 1.40-1.49 (m, 1H), 1.63-1.73 (m, 6H), 1.76-1.84 (m, 1H), 4.19-4.22 (dd, 1H, J=6.6, 9.0 Hz), 4.38-4.42 (dd, 1H J=6.0, 14.4 Hz), 4.44-4.48 (dd, 1H, J 6.0, 14.4 Hz), 4.59-4.65 (m, 2H), 6.21-6.23 (t, 1H, J 6 Hz), 6.58-6.60 (d, 1H, J=9.6 Hz), 6.86-6.89 (m, 2H), 6.91-6.92 (d, 1H, J=1.8 Hz), 7.01-7.03 (d, 1H, J=9 Hz), 7.22-7.24 (m, 1H), 8.33-8.34 (d, 1H, J=1.8 Hz).

HRMS: [MH]⁺ 527.3228 (calc. for $C_{29}H_{43}N_4O_5^+$) 527.3231 (found);

Example 4

Preparation of 5-isoxazoyl-Cha-Ile-aminomethyl-(1,3-dioxalane)phenyl (26)

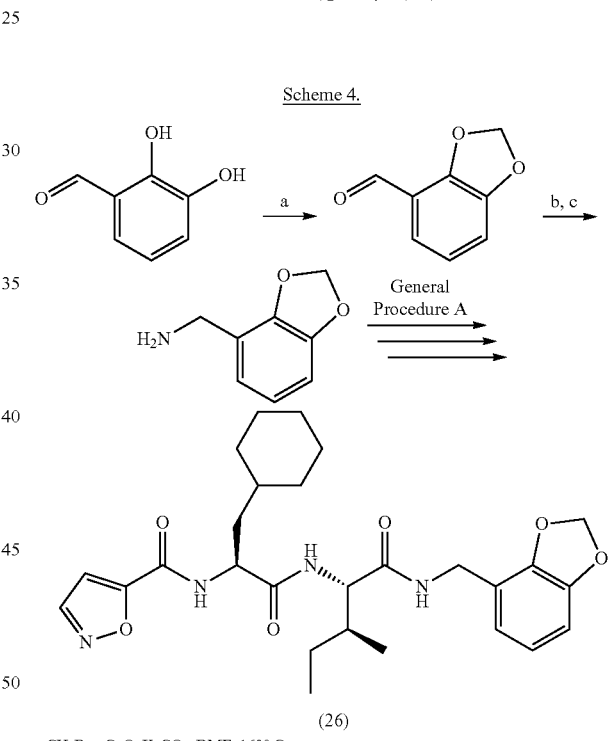

a CH₂Br₂, CuO, K₂CO₃, DMF, 160° C.;
b H₂NOH, MeOH—H₂O;
c NH₄CHO, Pd/C.

Step a: In a round-bottomed flask containing DMF (16 mL), 2,3-dihydroxybenzaldehyde (2.0 g, 14.5 mmol), dibromomethane (1.4 mL, 17.4 mmol), cupric oxide (0.11 g, 1.45 mmol), K₂CO₃ (2.4 g, 17.4 mmol) were added and the reaction mixture was refluxed at 160° C. overnight. The reaction mixture was filtered through a pad of celite and the filter cake was washed with CH₂Cl₂. The filtrate was washed with H₂O (3×). The organic layer was dried over MgSO₄, filtered and evaporated to dryness to give dark brown oil. The oil was distilled using a Kugelrohr distillation apparatus (b.p. 120° C./0.1 mm) to give product as yellow oil (1.5 g, 69% yield).

Step b: The resulting aldehyde was treated with hydroxylamine hydrochloride (2 eq.) and NaOH (4 eq.) in MeOH/H₂O (1:1) and stirred at room temperature for an hour. After completion, the reaction solution was evaporated to dryness and then re-dissolved in EtOAc, washed with 1M FlCl (2×), sat. NaHCO₃ (2×) and brine (1×). The organic phase was dried over MgSO₄, filtered and evaporated to dryness to give a white solid (70% yield).

Step c: To starting material oxime (2.5 mmol) in MeOH, ammonium formate (2 eq.) and Pd/C (100 mg) were added and the reaction mixture was stirred at room temperature for 48 hours. The reaction mixture was filtered through a pad of celite, washed with MeOH and the filtrate was evaporated. The impure crude was purified on preparative HPLC. The purified amine was coupled to Boc-protected isoleucine as described in the general amino acid coupling procedure A to give 26.

¹H NMR (600 MHz, DMSO-d₆), δ 0.84-0.90 (m, 6H), 0.90-1.01 (m, 2H), 1.05-1.23 (m, 4H), 1.29-1.37 (m, 1H), 1.43-1.50 (m, 1H), 1.60-1.75 (m, 6H), 1.76-1.81 (m, 1H), 1.84-1.92 (m, 1H), 4.25-4.27 (dd, 1H, J=7.2, 9.0 Hz), 4.39-4.42 (dd, 1H, J=6, 15 Hz), 4.47-4.51 (dd, 1H, J=6, 15 Hz), 4.62-4.66 (m, 1H), 5.96-5.97 (m, 2H), 6.19-6.24 (m, 1H), 6.52-6.58 (m, 1H), 6.74-6.80 (m, 3H), 6.91 (d, 1H, J=1.8 Hz), 7.03-7.08 (m, 1H), 8.33-8.34 (d, 1H, J=1.8 Hz).

HRMS: [MNa]⁺ 535.2527 (calc. for $C_{27}H_{36}N_4Na_1O_6^+$) 535.2528 (found).

Example 5

Preparation of 5-isoxazoyl-Cha-Ile-aminomethyl-(3,4-dichloro)phenyl represented by formula (27)

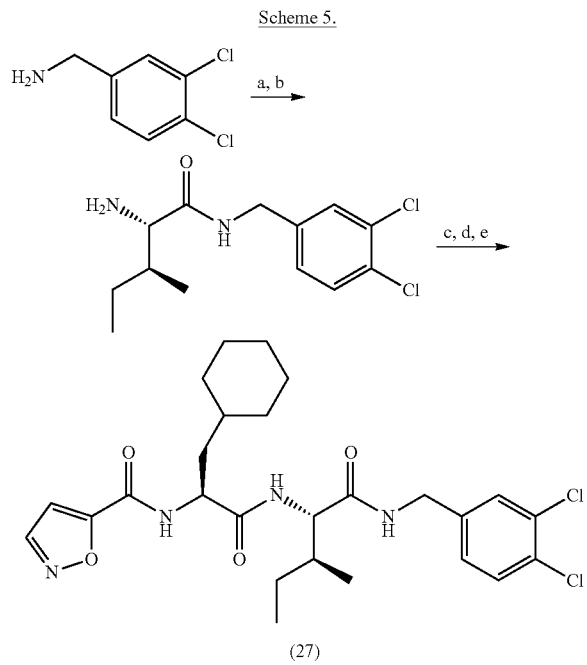

a Boc-Ile-OH, HBTU/DIPEA in DMF;
b 20% TFA in DCM;
c Boc-Cha-OH, HBTU/DIPEA in DMF;
d 20% TFA in DCM;
e Isoxazole 5-carboxylic acid, HBTU/DIPEA in DMF Compound 27 was synthesised by following the general amino acid coupling procedure A.

¹H NMR (600 MHz, DMSO-d₆): δ 0.79-0.82 (m, 6 H), 0.85-0.91 (m, 2 H), 1.03-1.16 (m, 4 H), 1.23-1.29 (m, 1 H), 1.40-1.47 (m, 1 H), 1.48-1.53 (m, 1 H), 1.56-1.76 (m, 7 H), 4.15-4.17 (t, 1 H, J=8.4 Hz), 4.22-4.30 (m, 2 H), 4.54-4.58 (m, 1 H), 7.15-7.16 (d, 1 H, J 1.8 Hz), 7.21-7.23 (dd, 1 H, J=1.8, 7.8 Hz), 7.47 (d, 1 H, J=1.8 Hz), 8.04-8.05 (d, 1 H, J 8.4 Hz), 8.58-8.60 (t, 1 H, J=6 Hz), 8.75-8.76 (d, 1 H, J=1.8 Hz), 8.93-8.94 (d, 1 H, J=8.4).

HRMS: [MH]⁺ 537.2030 (calc. for $C_{26}H_{35}Cl_2N_4O_{4+}$) 537.2028 (found).

Example 6

Preparation of 5-isoxazoyl-Cha-Ile-(4-phenyl)piperidine (30)

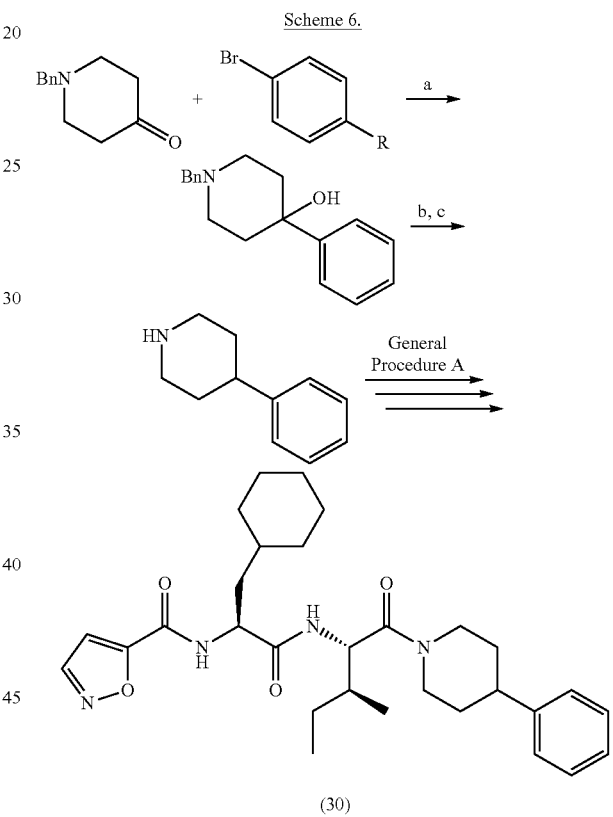

a Mg, THF, 65° C.;
b Pd/C, cat. HCl, 50 psi;
c 4M HCl in THF

Step a: Grignard Reaction: To a dry, nitrogen filled 2-necked round bottom flask was loaded magnesium turning (500 mg, 20 mmol), a small amount of iodine crystal and dry THF (3.8 mL). While stirring in a warm water bath (55-65° C.), a solution of bromobenzene (20.05 mmol) in anhydrous THf (5 mL) was loaded into a dry syringe and ⅓ of the solution was slowly transferred into the flask to initiate the reaction (Note: the colour slowly changed from dark brown to light brown). When the mixture began to boil, the water bath was removed and the mixture was diluted with dry THF (5 mL). The remaining bromobenzene solution was then slowly added to the flask. After refluxing the mixture for 20 min (65° C.), the mixture was cooled in an ice-water bath and a solution of 1-Boc-4-piperidone (2 g, 10 mmol) in dry THF (5 mL) was added drop wise (during which a white solid formed). Upon addition, the mixture was allowed to stir at room temperature for a further 30 minutes. A chilled solution of 10% citric acid was added and the mixture stirred for 1 minute (resulting in the formation of a gummy solid). Diethyl ether and water were added to dissolve the solid and the layers were separated. The aqueous layer was washed with ether (2×). The combined organic layer was washed with water (1×), dried over anhydrous MgSO$_4$, filtered and evaporated in vacuo. The crude product was purified by silica gel column chromatography, eluting with Petroleum Spirit/Ethyl Acetate (4:1) to give a white crystal product (0.96 g, 34.5% yield).

Step b: Hydrogenolysis: A mixture of the above crude product (200 mg), 10% Pd/C, and a catalytic amount of concentrated HO (1.2 mL) in EtOH (20 mL) were hydrogenated at 50 psi for an hour. The Pd/C was filtered through a pad of celite, and the solvent was evaporated in vacuo.

Step c: Boc deprotection: The above crude was treated with 4M HCl (4 mL) in THF (4 mL) for an hour. The THF solvent and HCl was evaporated and the residue was dissolved in DCM and washed with saturated NaHCO$_3$ (2×). Organic layers were dried over MgSO$_4$, filtered, and evaporated in vacuo. The residue amine (110.4 mg, 95% yield) was coupled to Boc-protected isoleucine as described in the general amino acid coupling procedure A to give 30.

$^1$H NMR (400 MHz, CDCl$_3$): δ 0.84-1.02 (m, 7 H), 1.08-1.26 (m, 4 H), 1.32-1.54 (m, 2 H), 1.57-1.83 (m, 10 H), 1.94-2.05 (m, 3 H), 2.68-2.83 (m, 2 H), 3.16-3.26 (m, 1 H), 4.11-4.20 (m, 1 H), 4.64-4.72 (m, 1 H), 4.73-4.80 (m, 1 H), 4.87-4.93 (q, 1 H, J=6.8 Hz), 6.76-6.84 (t, 1 H, J=9.2 Hz), 6.93-6.95 (br d, 1 H, J=2 Hz), 7.05-7.11 (t, 1 H J=8 Hz), 7.17-7.25 (m, 3 H), 7.29-7.34 (m, 2 H), 8.33-8.34 (d, 1 H, J=1.6 Hz).

HRMS: [MH]$^+$ 523.3279 (calc. for C$_{30}$H$_{43}$N$_4$O$_4^+$) 523.3280 (found).

Example 7

Preparation of 5-isoxazoyl-Cha-Ile-spiro[chroman-2, 4'-piperidine] (37)

Scheme 7.

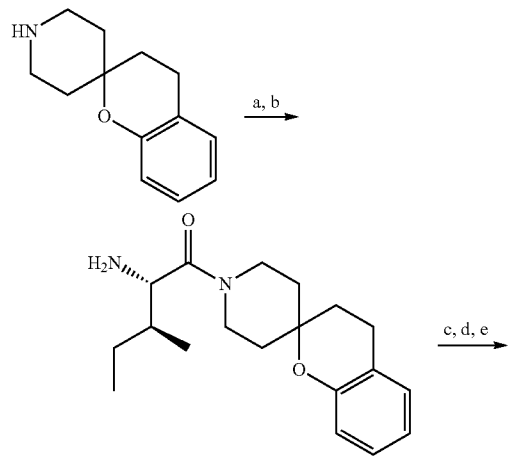

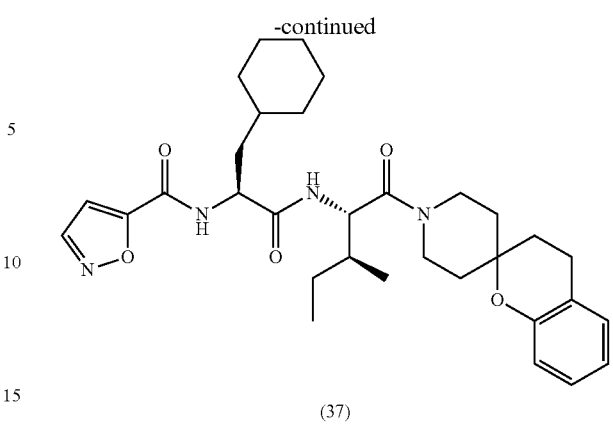

(37)

a Boc-Ile-OH, HBTU/DIPEA in DMF;
b 20% TFA in DCM;
c Boc-Cha-OH. HBTU/DIPEA in DMF;
d 20% TFA in DCM;
e Isoxazole 5-carboxylic acid, HBTU/DIPEA in DMF Compounds were synthesised by following general amino acid coupling procedure A.

$^1$H NMR (600 MHz, DMSO-d$_6$), δ 0.85-1.00 (m, 8H), 1.11-1.24 (m, 6H), 1.49-1.59 (m, 3H), 1.60-1.72 (m, 6H), 1.74-1.85 (m, 4H), 1.86-2.00 (m, 1H), 2.01-2.22 (m, 1H), 2.77-2.82 (m, 1H), 3.15-3.28 (m, 1H), 3.57-3.69 (m, 1H), 3.92-4.00 (m, 1H), 4.40-4.47 (m, 1H), 4.68-4.76 (m, 1H), 4.88-4.92 (t, 1H, J=8.4 Hz), 6.68 (br s, 2H), 6.82-7.14 (m, 4H), 7.31-7.57 (m, 1H), 8.34-8.35 (d, 1H, J=1.2 Hz).

HRMS: [MH]$^+$ 565.3384 (calc. for C$_{32}$H$_{45}$N$_4$O$_5^+$) 565.3385 (found).

Example 8

Preparation of 5-isoxazoyl-Cha-Ile-aminodimethyl-(2-methoxy)phenyl (39)

Scheme 8.

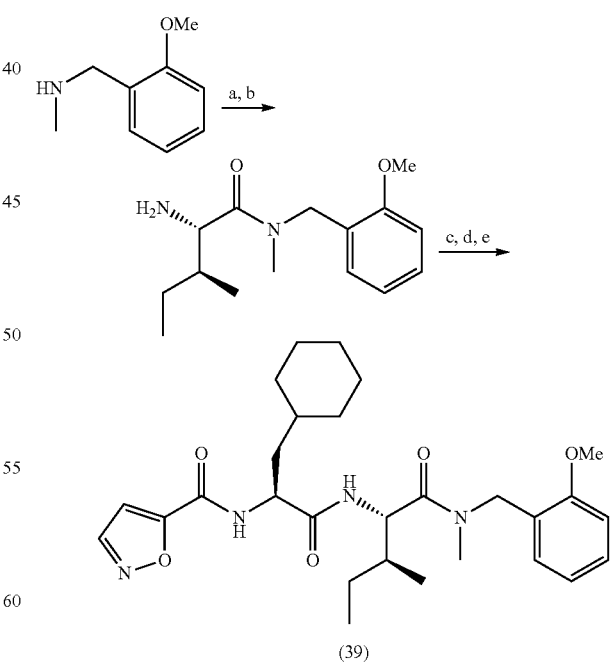

(39)

a Boc-Ile-OH, HBTU/DIPEA in DMF;
b 20% TFA in DCM;
c Boc-Cha-OH, HBTU/DIPEA in DMF;
d 20% TFA in DCM;
e Isoxazole 5-carboxylic acid, HBTU/DIPEA in DMF Compound 39 was synthesised by following the general amino acid coupling procedure A.

$^1$H NMR (600 MHz, DMSO-d$_6$): δ 0.75-0.76 (d, 1 H, J=6.6 Hz), 0.78-0.81 (t, 1 H, J 7.8 Hz), 0.86-0.88 (m, 4 H), 0.90-0.96 (m, 2 H), 1.00-1.15 (m, 3 H), 1.18-1.22 (m, 1 H), 1.32-1.38 (m, 1 H), 1.45-1.59 (m, 2 H), 1.60-1.78 (m, 6 H), 1.83-1.88 (m, 1 H), 2.80 (s, 1 H), 3.09 (s, 2 H), 3.82 (s, 3 H), 4.3-4.65 (m, 4 H), 6.86-6.88 (t, 1 H, J=7.2 Hz), 6.94-6.96 (m, 1 H), 7.01-7.11 (m, 1 H), 7.19-7.20 (m, 1 H), 7.26-7.33 (m, 1 H), 8.33-8.35 (d, 1 H, J=9 Hz), 8.78-8.79 (m, 1 H), 8.96-8.99 (m, 1 H).

HRMS: [MH]$^+$513.3071 (calc. for C$_{28}$H$_{41}$N$_4$O$_5{}^+$) 513.3071 (found).

Example 9

Preparation of 5-isoxazoyl-Cha-Thr(Me)-aminomethyl-(2-methoxy)phenyl (40)

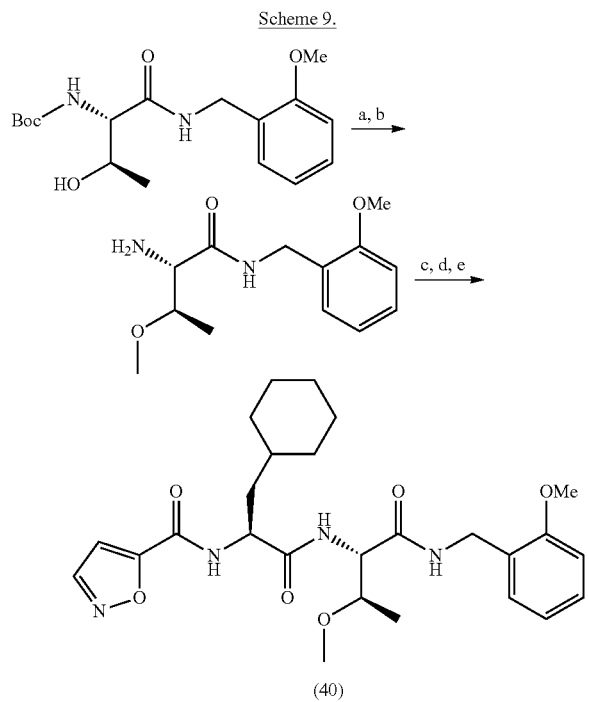

(40)

a MeI, LiO$^t$Bu, DMF;
b 20% TFA in DCM;
c Boc-Cha-OH, HBTU/DIPEA in DMF;
d 20% TFA in DCM;
e isoxazole-5-carboxylic acid, HBTU/DIPEA in DMF Step a: To a crude of Boc-Thr-aminomethyl-(2-methoxy) phenyl (0.541 mmol, prepared by following general amino acid coupling procedure A from 2-methoxybenzylamine and Boc-Thr-OH) was dissolved in DMF (3 mL). Lithium tert-butoxide (28.4 mg, 0.568 mmol, 1.05 eq) was added. The mixture was stirred at room temperature for 1 h. Methyl iodide (37 μL, 0.595 mmol, 1.1 eq) was added. The mixture was stirred at room temperature overnight, diluted with ethyl acetate (20 mL) and washed with brine (30 mL). The organic phase was dried (MgSO$_4$), filtered and evaporated on rotavapor to dryness.

Steps b-e: Following general amino acid coupling procedure A, the above crude was deprotected and coupled sequentially with Boc-Cha-OH and isoxazole-5-carboxylic acid to give compound 40.

$^1$H NMR (400 MHz, CDCl$_3$), δ 0.85-1.40 (m, 9H), 1.60-1.81 (m, 7H), 3.37 (s, 3H), 3.77-3.84 (m, 1H, β-CH of Thr), 3.84 (s, 3H), 4.38-4.46 (m, 2H, PhCH$_2$), 4.50 (dd, 1H, J=6.4, 3.2 Hz, α-CH of Thr), 4.63-4.69 (m, 1H, α-CH of Cha), 6.84-6.91 (m, 3H), 7.02-7.12 (m, 3H), 7.21-7.27 (m, 2H), 8.31 (d, 1H, J=2 Hz): $^{13}$C NMR (100 MHz, CDCl$_3$), δ 171.4, 168.7, 162.2, 157.4, 155.6, 151.0, 129.5, 129.0, 125.7, 120.6, 110.2, 106.9, 75.6, 56.9, 55.6, 55.2, 51.4, 40.2, 39.7, 34.1, 33.6, 32.5, 26.2, 26.0, 25.9, 14.0.

HRMS: [MH]$^+$501.2708 (calc. for C$_{26}$H$_{37}$N$_4$O$_6{}^+$) 501.2708 (found).

Example 10

Preparation of 5-(3-amino-isoxazoyl)-Cha-Ile-spiro[indene-1,4'-piperidine](42)

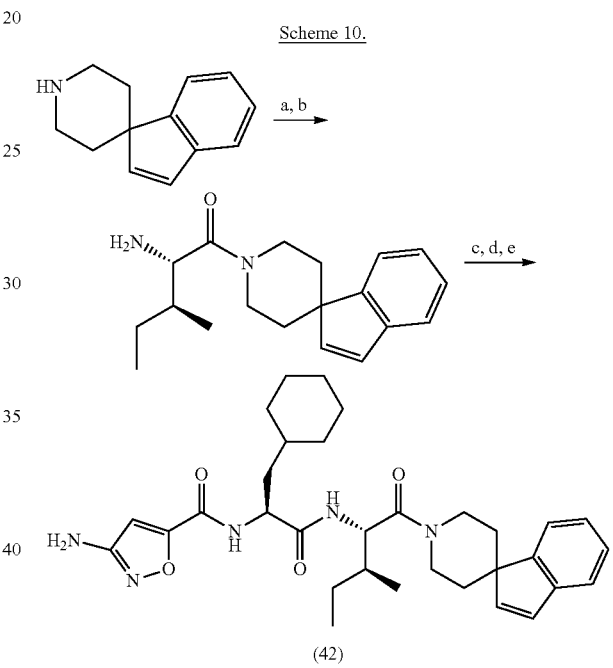

(42)

a Boc-Ile-OH, HBTU/DIPEA in DMF;
b 20% TFA in DCM;
c Boc-Cha-OH, HBTU/DIPEA in DMF;
d 20% TFA in DCM;
e 3-aminoisoxazole-5-carboxylic acid, BOP/DIPEA in DMF.

Compounds were synthesised by following general amino acid coupling procedure A.

$^1$H NMR (400 MHz, CDCl$_3$), δ 0.86-2.23 (m, 26H), 3.05-3.16 (m, 1H), 3.44-3.59 (m, 1H), 4.19-4.26 (m, 1H), 4.37 (lump, NH$_2$ overlapped with DOH, partially exchangeable with D$_2$O), 4.60-4.77 (m, 2H), 4.93-5.01 (m, 1H), 6.47 (s, 1H), 6.82-6.87 (m, 2H), 7.18-7.49 (m, 6H); $^{13}$C NMR (100 MHz, CDCl$_3$, two rotamers due to amide bond rotation). δ 171.9(0)/171.8(4), 170.6(8)/170.6(4), 163.6, 162.0, 155.8, 150.7(5)/150.7(0), 142.8/142.5. 139.7/139.3, 131.1/131.0, 127.4/127.3, 125.7, 125.5, 121.8, 121.6/121.4, 99.9, 53.1. 51.9/51.8, 51.5/51.4, 45.6/45.1, 41.5/41.4, 40.2/40.1, 37.9(4)/37.8(8), 34.1, 34.0. 33.6(2)/33.5(9), 33.4/33.2, 32.4(2)/32.4(0), 26.2, 26.1(3)/26.1(0), 26.0, 24.2, 16.0/15.6, 11.4/11.2.

HRMS: [MH]$^+$ 562.3388 (calc. for C$_{32}$H$_{44}$N$_5$O$_4$) 562.3388 (found);

Example 11

Preparation of 5-isoxazoyl-Cha-Thr(Me)-spiro[indene-1,4'-piperidine] (44)

Scheme 11.

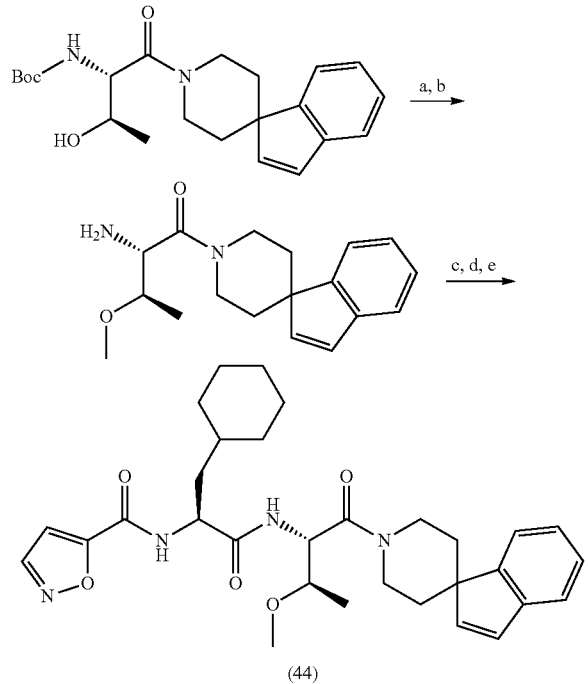

(44)

a MeI, LiO$^t$Bu, DMF;
b 20% TFA in DCM;
c Boc-Cha-OH. HBTU/DIPEA in DMF;
d 20% TFA in DCM;
e isoxazole 5-carboxylic acid, HBTU/DIPEA in DMF Step a: To a crude of Boc-Thr-spiro[indene-1,4'-piperidine](0.270 mmol, prepared by following general amino acid coupling procedure A from spiro[indene-1,4'-piperidine] and Boc-Thr-OH) was dissolved in DMF (3 mL). Lithium tert-butoxide (23 mg, 0.284 mmol, 1.05 eq) was added. The mixture was stirred at room temperature for 1 h. Methyl iodide (18.5 µL, 0.297 mmol, 1.1 eq) was added. The mixture was stirred at room temperature overnight, diluted with ethyl acetate (20 mL) and washed with brine (30 mL). The organic phase was dried (MgSO$_4$), filtered and evaporated on rotavapor to dryness.

Steps b-e: Following general amino acid coupling procedure A, the above crude was deprotected and coupled sequentially with Boc-Cha-OH and isoxazole-5-carboxylic acid to give compound 44.

$^1$H NMR (400 MHz, CDCl$_3$), δ 0.88-1.32 (M, 8H), 1.36-1.50 (m, 3H), 1.63-2.16 (m, 9H), 3.07-3.17 (m, 1H), 3.44-3.53 (m, 1H), 3.35 (s)/3.40(s, 3H, OMe of two rotamers), 3.66 (m, 1H, β-CH of Thr), 4.17 (br s, 1H), 4.65-4.72 (m, 1H), 4.72-4.79 (m, 1H, α-CH of Cha), 5.12 (1H, dd, J=8.0, 4.0 Hz, α-CH of Thr), 6.83 (d, 1H, J=6.0 Hz), 6.85 (d, 1H, J=6.0 Hz), 6.96 (d, 1H, J=1.6 Hz), 7.19-7.40 (m, 6H), 8.35 (d, 1H, J=2 Hz): $^{13}$C NMR (100 MHz, CDCl$_3$, two rotamers due to amide bond rotation), δ171.9(0)/171.8(4), 170.6(8)/170.6(5), 163.6, 162.1, 155.8, 150.8/150.7, 142.8/142.5, 139.7/139.3, 131.1/131.0, 127.4/127.3, 125.7/125.5, 121.8, 121.6/121.4, 99.9, 53.1, 51.9/51.8, 51.5/51.4, 45.6/45.1, 41.5/41.1, 40.2/40.1, 37.9(4)/37.8(8), 34.1, 34.0, 33.6(2)/33.5(9), 33.4/33.2, 32.4(2)/32.4(0), 26.2, 26.1(3)/26.1(0), 26.0, 24.2, 16.0/15.6, 11.4/11.2.

HRMS: [MH]$^+$ 549.3071 (calc. for C$_{31}$H$_{41}$N$_4$O$_5{}^+$) 549.3076 (found).

Further exemplary compounds of the formula (I) are provided below in Tables 1 to 4.

TABLE 1

HRMS data for representative compounds of formula (I)

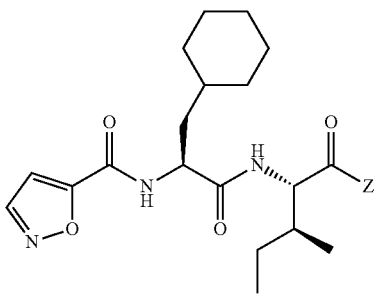

| Z | Formula for [M + H]$^+$ | HRMS* Calc. | Found |
|---|---|---|---|
| ![structure] | C$_{32}$H$_{48}$N$_7$O$_6{}^+$ | 626.3661 | 626.3667 |

TABLE 1-continued

HRMS data for representative compounds of formula (I)

| Z | Formula for [M + H]⁺ | HRMS* Calc. | Found |
|---|---|---|---|
| (3-(methylaminomethyl)-N-[(S)-1-carbamoyl-3-aminopropyl]benzamide) | $C_{31}H_{46}N_7O_6^+$ | 612.3504 | 612.3514 |
| N-methylbenzylamine | $C_{26}H_{37}N_4O_4^+$ | 469.2809 | 469.2818 |
| N,N-dimethylbenzylamine | $C_{27}H_{39}N_4O_4^+$ | 483.2966 | 483.2970 |
| 2-fluoro-N-methylbenzylamine | $C_{26}H_{36}FN_4O_4^+$ | 487.2715 | 487.2718 |
| 3-fluoro-N-methylbenzylamine | $C_{26}H_{36}FN_4O_4^+$ | 487.2715 | 487.2712 |
| 4-fluoro-N-methylbenzylamine | $C_{26}H_{36}FN_4O_4^+$ | 487.2715 | 487.2719 |
| 2-methoxy-N-methylbenzylamine | $C_{27}H_{39}N_4O_5^+$ | 499.2915 | 499.2915 |
| 3-methoxy-N-methylbenzylamine | $C_{27}H_{39}N_4O_5^+$ | 499.2915 | 499.2918 |
| 4-methoxy-N-methylbenzylamine | $C_{27}H_{39}N_4O_5^+$ | 499.2915 | 499.2918 |

TABLE 1-continued
HRMS data for representative compounds of formula (I)
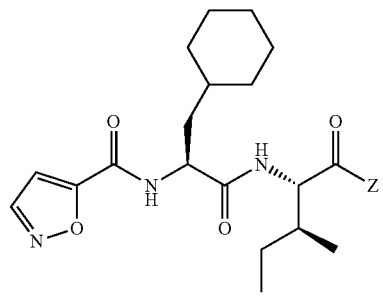
| Z | Formula for [M + H]$^+$ | Calc. | Found |
|---|---|---|---|
| (2-methylbenzyl)(methyl)amine | $C_{27}H_{39}N_4O_4^+$ | 483.2966 | 483.2965 |
| (2-methoxybenzyl)dimethylamine | $C_{28}H_{41}N_4O_5^+$ | 513.3071 | 513.3071 |
| (2-ethoxybenzyl)(methyl)amine | $C_{28}H_{41}N_4O_5^+$ | 513.3071 | 513.3071 |
| (2-sec-butoxybenzyl)(methyl)amine | $C_{30}H_{45}N_4O_5^+$ | 541.3384 | 541.3387 |
| (2-isopropoxybenzyl)(methyl)amine | $C_{29}H_{43}N_4O_5^+$ | 527.3228 | 527.3231 |
| (2-propoxybenzyl)(methyl)amine | $C_{29}H_{43}N_4O_5^+$ | 527.3228 | 527.3227 |

TABLE 1-continued
HRMS data for representative compounds of formula (I)
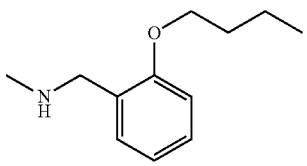
| Z | HRMS* Formula for [M + H]+ | Calc. | Found |
|---|---|---|---|
| 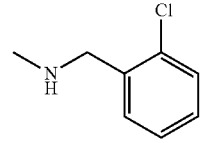 | $C_{30}H_{45}N_4O_5^+$ | 541.3384 | 541.3388 |
| 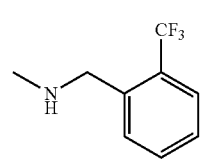 | $C_{26}H_{35}ClN_4Na_1O_4^+$ [M + Na]+ | 525.2239 | 525.2239 |
| 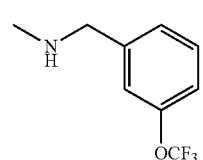 | $C_{27}H_{35}F_3N_4Na_1O_4^+$ [M + Na]+ | 559.2503 | 559.2502 |
| 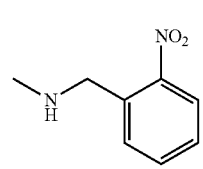 | $C_{27}H_{36}F_3N_4O_5^+$ | 553.2632 | 553.2632 |
| 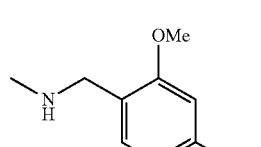 | $C_{26}H_{35}N_5Na_1O_6^+$ [M + Na]+ | 536.2480 | 536.2481 |
| 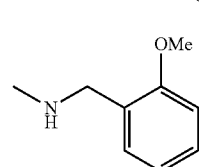 | $C_{28}H_{41}N_4O_6^+$ | 529.3021 | 529.3022 |
|  | $C_{28}H_{41}N_4O_6^+$ | 529.3021 | 529.3021 |

TABLE 1-continued
HRMS data for representative compounds of formula (I)
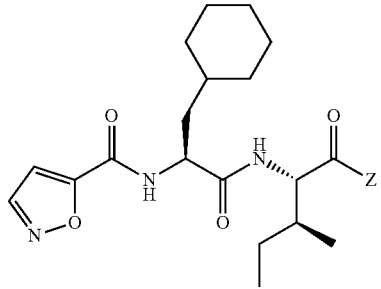
| Z | HRMS* Formula for [M + H]$^+$ | Calc. | Found |
|---|---|---|---|
| 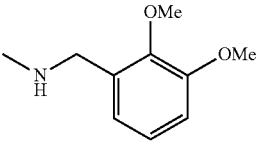 | $C_{28}H_{41}N_4O_6^+$ | 529.3021 | 529.3022 |
| 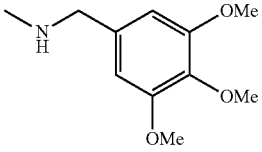 | $C_{28}H_{41}N_4O_6^+$ | 529.3021 | 529.3021 |
| 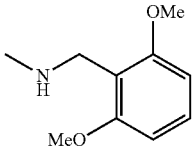 | $C_{29}H_{43}N_4O_7^+$ | 559.3126 | 559.3125 |
| 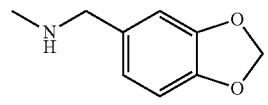 | $C_{28}H_{41}N_4O_6^+$ | 529.3021 | 529.3021 |
| 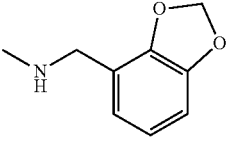 | $C_{27}H_{37}N_4O_6^+$ | 513.2708 | 513.2708 |
| 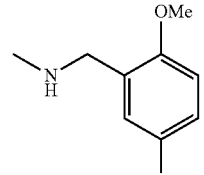 | $C_{27}H_{36}N_4Na_1O_6^+$ [M + Na]$^+$ | 535.2527 | 535.2528 |
| 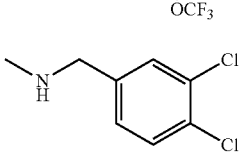 | $C_{28}H_{38}F_3N_4O_6^+$ | 583.2738 | 583.2739 |
|  | $C_{26}H_{35}Cl_2N_4O_4^+$ | 537.2030 | 537.2028 |

TABLE 1-continued

HRMS data for representative compounds of formula (I)

| Z | Formula for [M + H]⁺ | HRMS* Calc. | Found |
|---|---|---|---|
| 3,5-bis(trifluoromethyl)benzyl(methyl)amino | $C_{28}H_{35}F_6N_4O_4^+$ | 605.2557 | 605.2556 |
| (2-biphenylmethyl)(methyl)amino | $C_{32}H_{41}N_4O_4^+$ | 545.3122 | 545.3121 |
| (3-biphenylmethyl)(methyl)amino | $C_{32}H_{41}N_4O_4^+$ | 545.3122 | 545.3125 |
| (4-biphenylmethyl)(methyl)amino | $C_{32}H_{41}N_4O_4^+$ | 545.3122 | 545.3123 |
| (naphthalen-1-ylmethyl)(methyl)amino | $C_{30}H_{39}N_4O_4^+$ | 519.2966 | 519.2968 |
| 1-methyl-4-phenylpiperidin-4-yl | $C_{30}H_{43}N_4O_4^+$ | 523.3279 | 523.3280 |

TABLE 1-continued

HRMS data for representative compounds of formula (I)

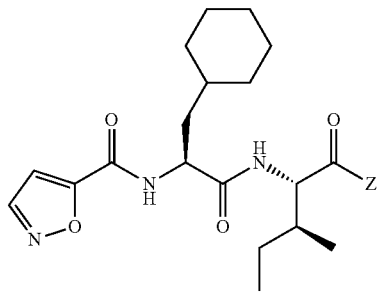

| Z | Formula for [M + H]⁺ | HRMS* Calc. | Found |
|---|---|---|---|
| N-methylpiperidine-4-(4-chlorophenyl) | $C_{30}H_{42}ClN_4O_4^+$ | 577.2889 | 577.2894 |
| N-methylpiperidine-4-(4-methoxyphenyl) | $C_{31}H_{45}N_4O_5^+$ | 553.3384 | 553.3384 |
| N-methylpiperidine-4-(2,5-dimethoxyphenyl) | $C_{32}H_{47}N_4O_6^+$ | 583.3490 | 583.3492 |
| N-methylpiperidine-4-benzyl | $C_{31}H_{45}N_4O_4^+$ | 537.3435 | 537.3449 |
| N-methylpiperidine-4-(2-trifluoromethylphenyl) | $C_{31}H_{42}F_3N_4O_4^+$ | 591.3153 | 591.3156 |
| N-methyl-4-hydroxy-4-(2,4-bis-trifluoromethylphenyl)piperidine | $C_{32}H_{41}F_6N_4O_5^+$ | 675.2976 | 675.2976 |

TABLE 1-continued

HRMS data for representative compounds of formula (I)

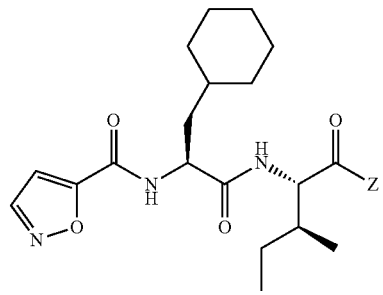

| Z | HRMS* Formula for [M + H]$^+$ | Calc. | Found |
|---|---|---|---|
| (1-methylpiperidin-4-yl attached to 2-biphenyl) | $C_{36}H_{47}N_4O_4^+$ | 599.3592 | 599.3597 |
| (1-methylpiperidin-4-yl attached to 3-biphenyl) | $C_{36}H_{47}N_4O_4^+$ | 599.3592 | 599.3590 |
| (1-methylpiperidin-4-yl attached to 4-biphenyl) | $C_{36}H_{47}N_4O_4^+$ | 599.3592 | 599.3594 |
| (N-tert-butyl 1-methylpiperidine-2-carboxamide) | $C_{29}H_{48}N_5O_5^+$ | 546.3650 | 546.3653 |
| (4-phenyl-1-methylpiperidin-4-yl acetamide) | $C_{32}H_{46}N_5O_5^+$ | 580.3493 | 580.3493 |

TABLE 1-continued

HRMS data for representative compounds of formula (I)

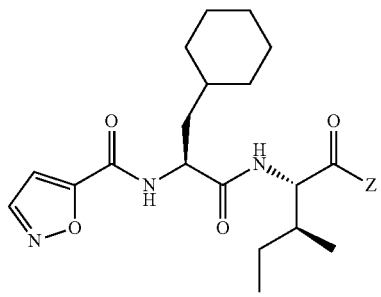

| Z | Formula for [M + H]⁺ | HRMS* Calc. | Found |
|---|---|---|---|
| (1-methyl-6,7-dimethoxy-tetrahydroisoquinoline) | $C_{30}H_{43}N_4O_6^+$ | 555.3177 | 555.3179 |
| (1-methylpiperidin-3-yl)-NH-(2-fluorophenyl) | $C_{30}H_{43}FN_5O_4^+$ | 556.3294 | 556.3296 |
| (1-methylpiperidin-3-yl)-NH-(3-fluorophenyl) | $C_{30}H_{43}FN_5O_4^+$ | 556.3294 | 556.3293 |
| (1-methylpiperidin-3-yl)-NH-(4-fluorophenyl) | $C_{30}H_{43}FN_5O_4^+$ | 556.3294 | 556.3298 |
| (1-methylpiperidin-3-yl)-NH-(2-CF₃-phenyl) | $C_{31}H_{43}F_3N_5O_4^+$ | 606.3262 | 606.3263 |
| (1-methylpiperidin-3-yl)-NH-(3-CF₃-phenyl) | $C_{31}H_{43}F_3N_5O_4^+$ | 606.3262 | 606.3265 |
| (1-methylpiperidin-3-yl)-NH-(4-CF₃-phenyl) | $C_{31}H_{43}F_3N_5O_4^+$ | 606.3262 | 606.3269 |

TABLE 2
| HRMS data for representative compounds of formula (I) | | | |
|---|---|---|---|
| 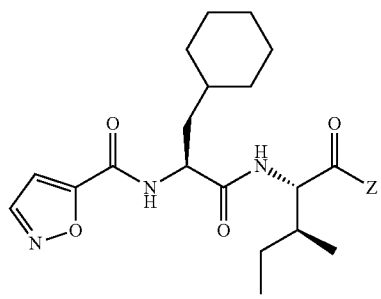 | | | |
| 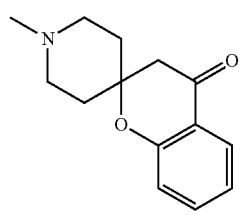 | $C_{32}H_{43}N_4O_6^+$ | 579.3177 | 579.3178 |
| 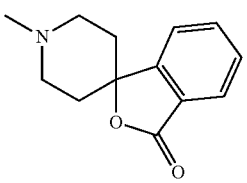 | $C_{31}H_{40}N_4NaO_6^+$ [M + Na]$^+$ | 587.2840 | 587.2843 |
| 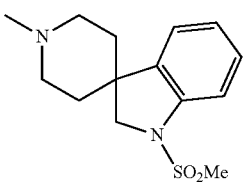 | $C_{32}H_{45}N_5NaO_6S^+$ [M + Na]$^+$ | 650.2983 | 650.2985 |
| 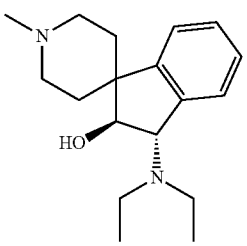 | $C_{36}H_{54}N_5O_5^+$ | 636.4119 | 636.4135 |
| 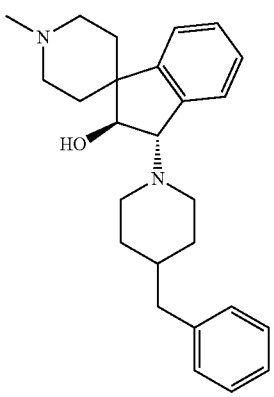 | $C_{44}H_{60}N_5O_5^+$ | 738.4589 | 738.4590 |

TABLE 2-continued
HRMS data for representative compounds of formula (I)
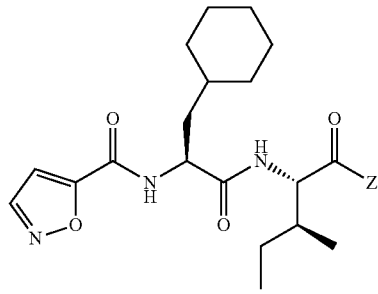
| | | | |
|---|---|---|---|
| 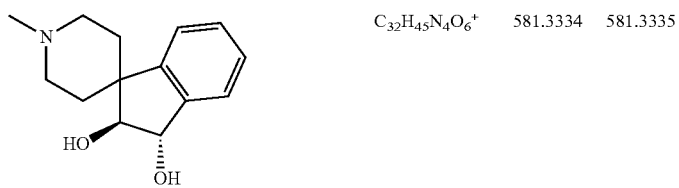 | $C_{32}H_{45}N_4O_6^+$ | 581.3334 | 581.3335 |
| 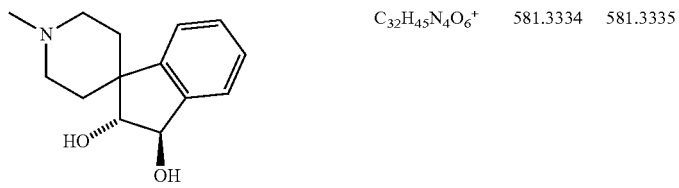 | $C_{32}H_{45}N_4O_6^+$ | 581.3334 | 581.3335 |
| 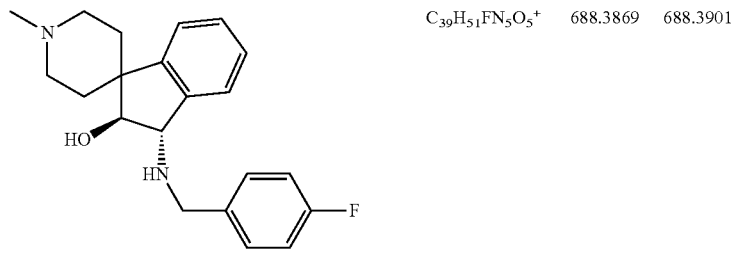 | $C_{39}H_{51}FN_5O_5^+$ | 688.3869 | 688.3901 |
| 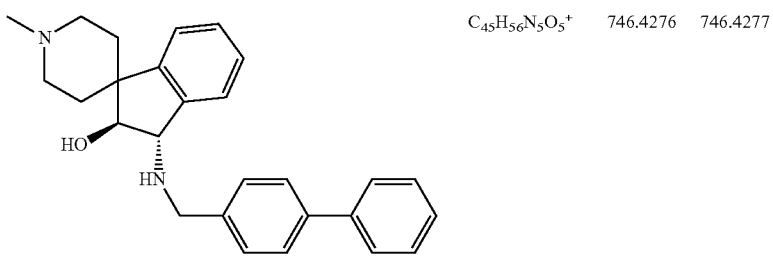 | $C_{45}H_{56}N_5O_5^+$ | 746.4276 | 746.4277 |
| 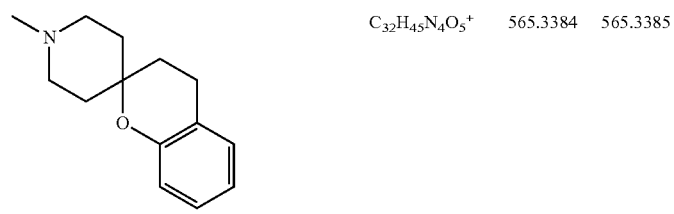 | $C_{32}H_{45}N_4O_5^+$ | 565.3384 | 565.3385 |

TABLE 3
HRMS data for representative compounds of formula (I)
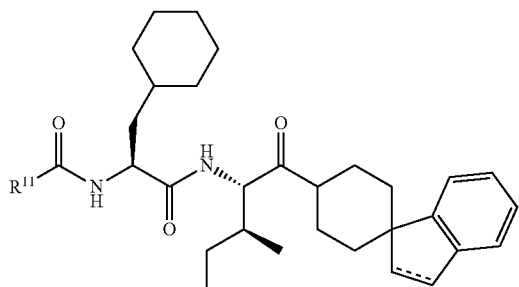
n = 1, single bond
n = 2, double bond
| n | R[11] | Formula for [M + H]+ | HRMS* Calc. | Found |
|---|---|---|---|---|
| 2 | 2-furyl | $C_{33}H_{44}N_3O_4^+$ | 546.3326 | 546.3330 |
| 2 | 3-pyridyl | $C_{34}H_{45}N_4O_3^+$ | 557.3486 | 557.3494 |
| 2 | 2-pyrazinyl | $C_{33}H_{44}N_5O_3^+$ | 558.3439 | 558.3443 |
| 2 | 1H-1,2,4-triazol-3-yl | $C_{31}H_{43}N_6O_3^+$ | 547.3391 | 547.3395 |
| 2 | 5-methylisoxazol-3-yl | $C_{33}H_{45}N_4O_4^+$ | 561.3435 | 561.3428 |
| 2 | 1H-imidazol-4-yl | $C_{32}H_{44}N_5O_3^+$ | 546.3439 | 546.3437 |
| 2 | 1-methyl-1H-pyrazol-4-yl | $C_{33}H_{46}N_5O_3^+$ | 560.3601 | 560.3595 |
| 2 | 3,5-dimethoxyphenyl | $C_{37}H_{49}N_3Na_1O_5^+$ [M + Na]+ | 638.3564 | 638.3573 |

TABLE 3-continued
HRMS data for representative compounds of formula (I)
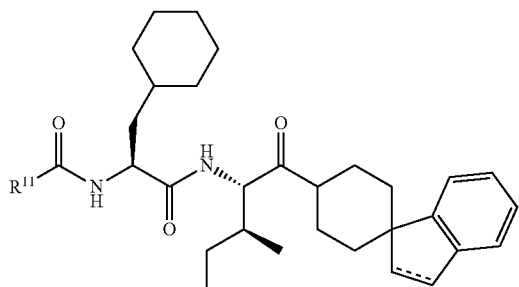
n = 1, single bond
n = 2, double bond
| n | R¹¹ | Formula for [M + H]⁺ | HRMS* Calc. | Found |
|---|---|---|---|---|
| 2 | diphenylmethyl | $C_{42}H_{51}N_3Na_1O_3^+$ [M + Na]⁺ | 668.3823 | 668.3819 |
| 2 | indol-3-ylmethyl | $C_{37}H_{47}N_4O_3^+$ | 595.3643 | 595.3644 |
| 2 | 5-(4-methylphenyl)isoxazol-3-yl | $C_{39}H_{49}N_4O_4^+$ | 637.3748 | 637.3752 |
| 2 | (E)-2-(pyridin-3-yl)vinyl | $C_{36}H_{47}N_4O_3^+$ | 583.3643 | 583.3645 |
| 2 | (E)-2-(3-chlorophenyl)vinyl | $C_{37}H_{47}ClN_3O_3^+$ | 616.3300 | 616.3296 |
| 2 | propyl | $C_{32}H_{48}N_3O_3^+$ | 522.3696 | 522.3698 |
| 2 | 5-oxopyrrolidin-2-yl | $C_{33}H_{47}N_4O_4^+$ | 563.3592 | 563.3593 |

TABLE 3-continued
HRMS data for representative compounds of formula (I)
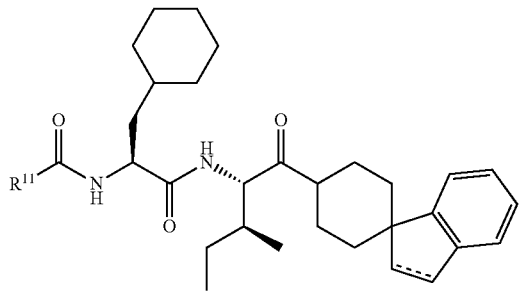
n = 1, single bond
n = 2, double bond
| n | R¹¹ | Formula for [M + H]⁺ | HRMS* Calc. | Found |
|---|-----|----------------------|-------------|-------|
| 2 | pyrrolidin-2-yl | $C_{33}H_{49}N_4O_3^+$ | 549.3799 | 549.3792 |
| 2 | H₂N–CH₂– | $C_{30}H_{45}N_4O_3^+$ | 509.3486 | 509.3492 |
| 2 | H₂N–(CH₂)₃– | $C_{32}H_{49}N_4O_3^+$ | 537.3799 | 537.3790 |
| 2 | H₂N–(CH₂)₃– | $C_{32}H_{51}N_4O_3^+$ | 539.3956 | 539.3956 |
| 2 | H₂N–CH₂–CH(OH)–CH₂– | $C_{32}H_{49}N_4O_4^+$ | 553.3748 | 553.3748 |
| 2 | H₂N–CH(CH₂OH)– | $C_{31}H_{47}N_4O_4^+$ | 539.3592 | 539.3589 |
| 2 | piperidin-4-yl | $C_{31}H_{51}N_4O_3^+$ | 563.3956 | 563.3956 |
| 2 | trihydroxy-hydroxymethyl-cyclohexyl | $C_{35}H_{52}N_3O_7^+$ | 626.3800 | 626.3806 |

TABLE 3-continued

HRMS data for representative compounds of formula (I)

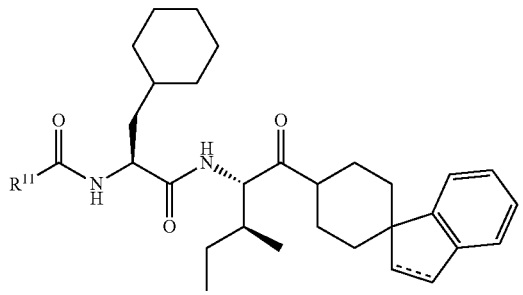

n = 1, single bond
n = 2, double bond

| n | R¹¹ | Formula for [M + H]⁺ | HRMS* Calc. | Found |
|---|---|---|---|---|
| 2 | H₂N–CH₂CH₂–CH(OH)– (with stereochem) | $C_{32}H_{49}N_4O_4^+$ | 553.3748 | 553.3750 |
| 1 | H₂N–CH₂CH₂–CH(OH)– | $C_{32}H_{51}N_4O_4^+$ | 555.3905 | 555.3900 |
| 1 | H₂N–CH₂–C(=O)–CH₂– | $C_{32}H_{49}N_4O_4^+$ | 553.3748 | 553.3750 |
| 1 | CH₃CH₂–C(=O)–CH₂– | $C_{32}H_{48}N_3O_4^+$ | 538.3639 | 538.3640 |
| 1 | H₂N–CH=CH–C(=O)–CH₂– | $C_{32}H_{47}N_4O_4^+$ | 551.3592 | 551.3591 |
| 2 | HO–CH₂CH₂–C(=O)–CH₂– | $C_{32}H_{46}N_3O_5^+$ | 552.3432 | 552.3433 |
| 1 | HO–CH₂CH₂–C(=O)–CH₂– | $C_{32}H_{48}N_3O_5^+$ | 554.3588 | 554.3903 |
| 2 | H₂N– | $C_{29}H_{43}N_4O_3^+$ | 495.3330 | 495.3334 |
| 2 | HO–CH₂CH₂–NH– | $C_{31}H_{47}N_4O_4^+$ | 539.3592 | 539.3592 |

TABLE 3-continued
HRMS data for representative compounds of formula (I)
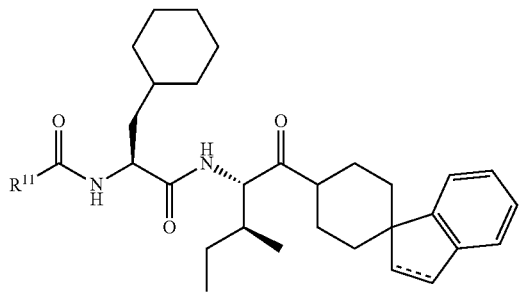
n = 1, single bond
n = 2, double bond
| n | R[11] | Formula for [M + H]$^+$ | HRMS* Calc. | Found |
|---|---|---|---|---|
| 2 | benzylamino | $C_{36}H_{49}N_4O_3^+$ | 585.3799 | 585.3799 |
| 2 | 2,3-diaminopropyl | $C_{31}H_{48}N_5O_3^+$ | 538.3752 | 538.3752 |
| 2 | 2-iminoimidazolidinyl | $C_{32}H_{47}N_6O_3^+$ | 563.3704 | 563.3704 |
| 2 | 3-amino-carbamoyl | $C_{32}H_{48}N_5O_4^+$ | 566.3701 | 566.3701 |
| 2 | 3-amino-isoxazol-5-yl | $C_{32}H_{44}N_5O_4^+$ | 562.3388 | 562.3388 |
| 2 | tert-butoxy | $C_{33}H_{50}N_3O_4^+$ | 552.3796 | 552.3796 |
*Note:
molecular ion for [M + H]$^+$ unless indicated otherwise TABLE 4
HRMS data for representative compounds of formula (I)
| Structure | HRMS* Formula for [M + H]+ | Calc. | Found |
|---|---|---|---|
| 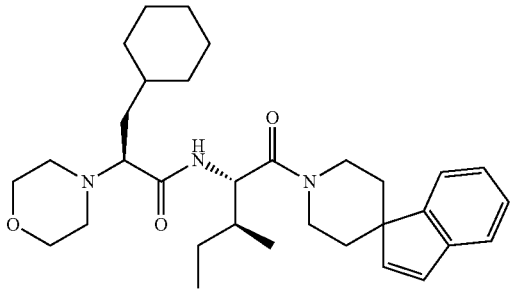 [SMILES: CC[C@H](C)[C@H](NC(=O)[C@H](CC1CCCCC1)N1CCOCC1)C(=O)N1CCC2(C=Cc3ccccc32)CC1] | $C_{32}H_{48}N_3O_3^+$ | 522.3690 | 522.3693 |
| 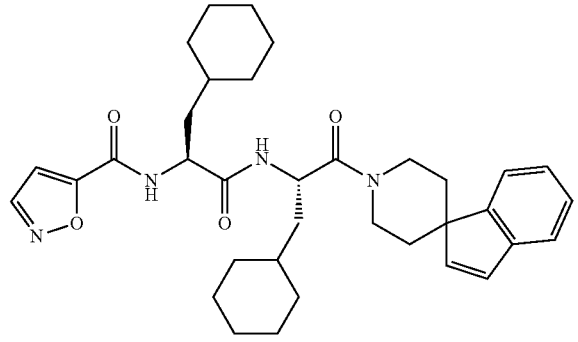 [SMILES: O=C(N[C@@H](CC1CCCCC1)C(=O)N[C@@H](CC1CCCCC1)C(=O)N1CCC2(C=Cc3ccccc32)CC1)c1ccno1] | $C_{35}H_{47}N_4O_4^+$ | 587.3592 | 587.3588 |
| 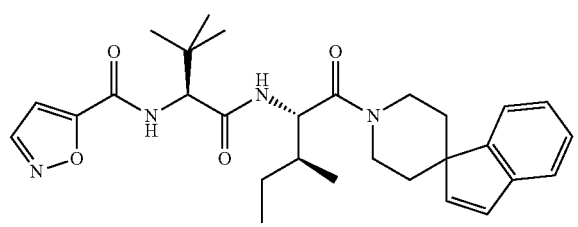 [SMILES: CC[C@H](C)[C@H](NC(=O)[C@@H](NC(=O)c1ccno1)C(C)(C)C)C(=O)N1CCC2(C=Cc3ccccc32)CC1] | $C_{29}H_{39}N_4O_4^+$ | 507.2966 | 507.2965 |
| 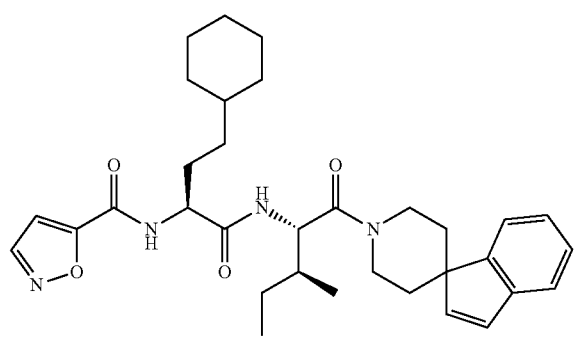 [SMILES: CC[C@H](C)[C@H](NC(=O)[C@H](CCC1CCCCC1)NC(=O)c1ccno1)C(=O)N1CCC2(C=Cc3ccccc32)CC1] | $C_{33}H_{45}N_4O_4^+$ | 561.3435 | 561.3438 |

TABLE 4-continued

HRMS data for representative compounds of formula (I)

| Structure | Formula for [M + H]+ | HRMS* Calc. | Found |
|---|---|---|---|
| (structure) | C₃₁H₄₆N₃O₂⁺ | 492.3585 | 492.3590 |
| (structure) | C₂₅H₃₈N₃O₂⁺ | 412.2959 | 412.2958 |
| (structure) | C₂₉H₄₄N₃O₂⁺ | 466.3428 | 466.3432 |
| (structure) | C₂₇H₃₉N₃Na₁O₃⁺ [M + Na]⁺ | 476.2884 | 476.2879 |
| (structure) | C₃₀H₄₀N₃O₄⁺ | 506.3013 | 506.3014 |

TABLE 4-continued

HRMS data for representative compounds of formula (I)

| Structure | Formula for [M + H]⁺ | Calc. | Found |
|---|---|---|---|
| | $C_{28}H_{43}N_4O_4^+$ | 499.3279 | 499.3281 |
| | $C_{25}H_{38}N_3O_2^+$ | 412.2964 | 412.2961 |
| | $C_{30}H_{40}N_5O_5^+$ | 550.3024 | 550.3019 |
| | $C_{26}H_{37}N_4O_6^+$ | 501.2708 | 501.2708 |
| | $C_{31}H_{41}N_4O_5^+$ | 549.3071 | 549.3076 |

TABLE 4-continued
HRMS data for representative compounds of formula (I)
| Structure | Formula for [M + H]⁺ | Calc. | Found |
|---|---|---|---|
| 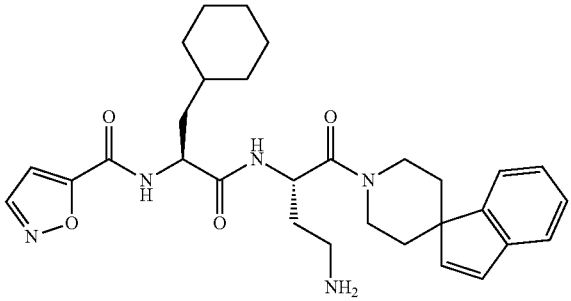 [SMILES: NCC[C@H](NC(=O)[C@H](CC1CCCCC1)NC(=O)c1ccno1)C(=O)N1CCC2(C=Cc3ccccc32)CC1] | $C_{30}H_{40}N_5O_4^+$ | 534.3075 | 534.3070 |
| 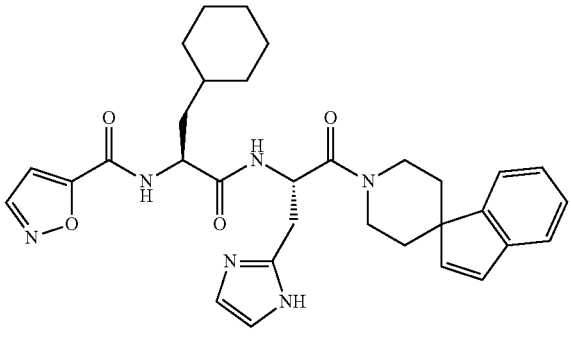 [SMILES: O=C(N[C@@H](CC1CCCCC1)C(=O)N[C@@H](Cc1ncc[nH]1)C(=O)N1CCC2(C=Cc3ccccc32)CC1)c1ccno1] | $C_{32}H_{39}N_6O_4^+$ | 571.3027 | 571.3026 |
| 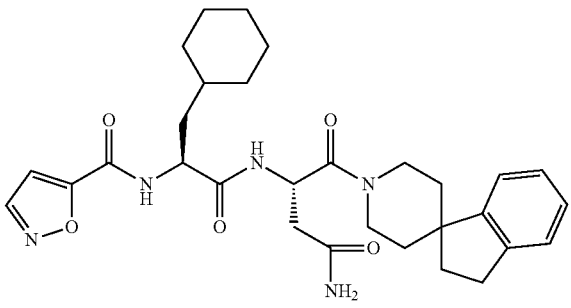 [SMILES: NC(=O)C[C@H](NC(=O)[C@H](CC1CCCCC1)NC(=O)c1ccno1)C(=O)N1CCC2(CCc3ccccc32)CC1] | $C_{30}H_{40}N_5O_5^+$ | 550.3024 | 550.3007 |
| 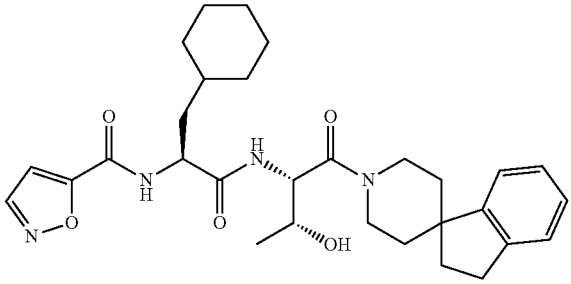 [SMILES: C[C@@H](O)[C@H](NC(=O)[C@H](CC1CCCCC1)NC(=O)c1ccno1)C(=O)N1CCC2(CCc3ccccc32)CC1] | $C_{30}H_{39}N_4O_5^+$ | 535.2915 | 535.2915 |

TABLE 4-continued

HRMS data for representative compounds of formula (I)

| Structure | Formula for [M + H]+ | Calc. | Found |
|---|---|---|---|
| 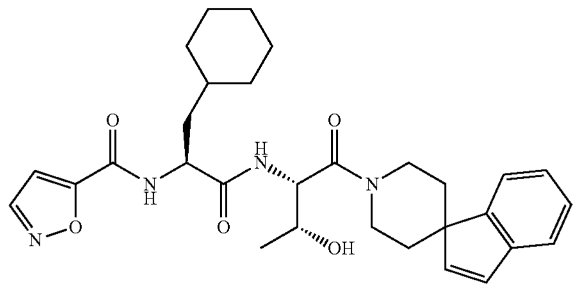 [SMILES: C[C@@H](O)[C@H](NC(=O)[C@H](CC1CCCCC1)NC(=O)c1ccno1)C(=O)N1CCC2(C=Cc3ccccc32)CC1] | $C_{30}H_{41}N_4O_5^+$ | 537.3071 | 537.3071 |
| | $C_{33}H_{45}N_4O_4^+$ | 561.3435 | 561.3435 |
| 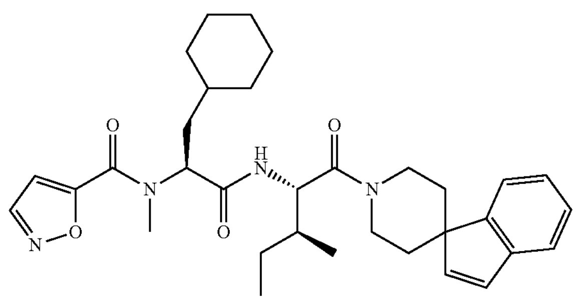 [SMILES: CC[C@H](C)[C@H](NC(=O)[C@H](CC1CCCCC1)N(C)C(=O)c1ccno1)C(=O)N1CCC2(C=Cc3ccccc32)CC1] | $C_{33}H_{44}N_4NaO_4^+$ [M + Na]+ | 583.3255 | 583.3250 |
| | $C_{33}H_{45}N_4O_4^+$ | 561.3435 | 561.3435 |
| 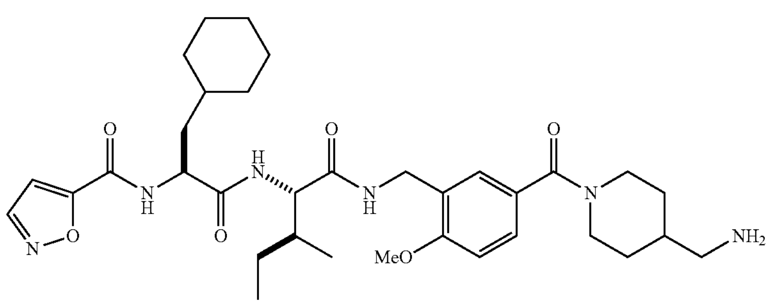 | $C_{34}H_{49}N_5Na_1O_5^+$ [M + Na]+ | 630.3631 | 630.3809 |

TABLE 4-continued
HRMS data for representative compounds of formula (I)
| Structure | Formula for [M + H]$^+$ | Calc. | Found |
|---|---|---|---|
| 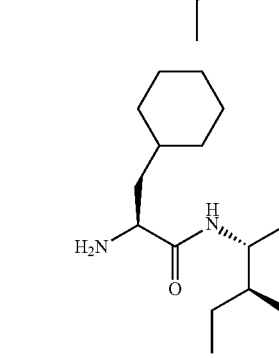 | $C_{33}H_{51}N_6O_6^+$ | 627.3865 | 627.3863 |
| 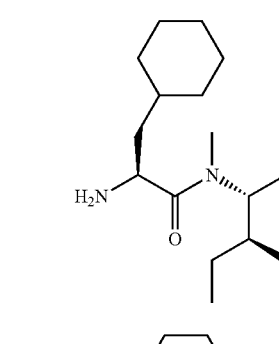 | $C_{28}H_{42}N_3O_2^+$ | 452.3272 | 452.3274 |
| | $C_{29}H_{44}N_3O_2^+$ | 466.3428 | 466.3424 |
| 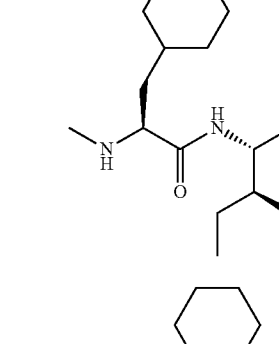 | $C_{29}H_{44}N_3O_2^+$ | 466.3428 | 466.3428 |
| 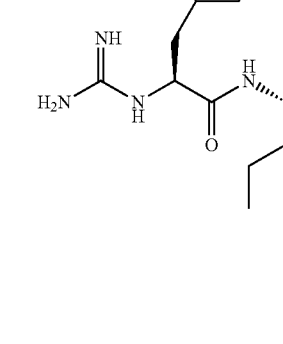 | $C_{29}H_{44}N_5O_2^+$ | 494.3490 | 494.3489 |

TABLE 4-continued

HRMS data for representative compounds of formula (I)

| Structure | Formula for [M + H]⁺ | HRMS* Calc. | Found |
|---|---|---|---|
| 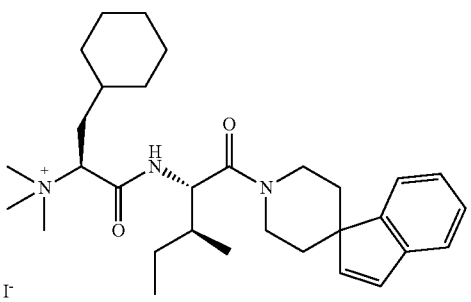 | $C_{31}H_{48}N_3O_2^+$ (cation alone) | 494.3741 | 494.3741 |

*Note:
molecular ion for [M + H]⁺ unless indicated otherwise

Example 12

Determination of PAR2 Activation

The ability of the compounds of the present invention to activate PAR2 may be assessed via calcium mobilisation assays. It is appreciated that compounds that activate the release of intracellular calcium from one type of cell are agonists or partial agonists, while those that inhibit such release may be antagonists. However these "agonist" and "antagonist" effects may be reversed for a given compound or PAR2 ligand in a different cell, or opposite responses may be observed using a different reported assay (e.g. ERK phosphorylation or cAMP stimulation. All cell culture reagents used for these assays are purchased from Invitrogen (Carlsbad, Calif.) and Sigma Aldrich (St. Louis. MO). Cell lines are cultured in medium at 37° C. and 5% $CO_2$ based on information provided by ATCC (Manassas, Va.). Cell lines that may be used for these experiments include but are not limited to the human cell lines HT29, HEK293, MM96L. Saos-2. MG-63, HeLa, JAM, A549 and HOP62. The general assay protocols may vary slightly depending on the chosen cell line. In general, during cell culture passage, cell dissociation solution (CDS, Sigma Aldrich) is used to replace trypsin to dissociate cells from surface. Lipopolysaccharide (LPS) and trypsin are purchased from Sigma Aldrich. Trichostatin (TSA) and PAR2 activating peptide, 2f-LIGRLO-$NH_2$, are synthesized in-house. ELISA sets are purchased from BD Pharmingen (San Jose, Calif.) and cytokine array kits are purchased from RayBiotecho (Norcross, Ga.). Anti-PAR antibody is purchased from Santa Cruz Biotechnology (Santa Cruz, Calif.) and anti-goat antibody conjugated with Alexa-Fluor 488 is purchased from Invitrogen.

Cells are seeded overnight in 96-well black walled, clear bottomed, plate at approximately $2\times10^4$ to $4\times10^5$ cells per well. On the day of the experiment, the supernatant is removed and the cells are incubated in dye loading buffer (Hank's Balanced Salt Solution (HBSS) with 4 μM to 2 mM Fluo-3 AM, 25 μL pluronic acid, 1% fetal bovine serum (FBS), 2.5 mM probenecid and 20 mM HEPES) for one hour at 37° C. The cells are then washed twice with HBSS and transferred to a Polarstar spectrofluorimeter (BMG, Durham N.C.).

To determine agonist activity, the compounds of the present invention are added to the individual wells 10 s after reading commences at various concentrations and fluorescence is measured in real time from the bottom of the plate at an excitation wavelength of 480 nm or 495 nm and emission wavelength of 520 nm. HBSS is prepared in-house and all other reagents are purchased from Invitrogen, Carlsbad. Plates are supplied by DKSH. Zurich. Calcimycin (A23187, Invitrogen) is used to measure maximum fluorescence, with individual results normalized accordingly. Results of exemplified compounds of the general formula (I) are shown below in Tables 5 and 6. Additionally, a graphical representation of the above mentioned agonist assays for the PAR2 agonist 6 is shown in FIG. 1 and described below.

Three different concentrations of 6 added to HT29 cells at room temperature. Duplicate measurements were made for each data point, accordingly, each data point represents mean±SEM. Net changes in fluorescence were calculated as a percentage relative to the maximum response given by 100 μM of the PAR2 agonist 2f-LIGRLO-$NH_2$. At 30 μM. 6 was giving up to 50% response, indicating that the $EC_{50}$ of 6 is approximately 30 μM.

TABLE 5

Biological Activity for representative PAR2 Ligands as Agonists or Partial Agonists of $Ca^{2+}$ release in HT29 cells.

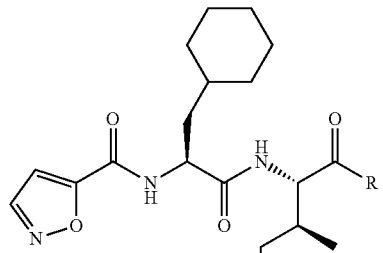

| Compound No. | R | $EC_{50}$ (μM) |
|---|---|---|
| 1 | ![R group structure with NH-CH2-phenyl-C(O)-NH-CH(CONH2)-(CH2)4-NH2] | 0.2 |

TABLE 5-continued

Biological Activity for representative PAR2 Ligands as Agonists or Partial Agonists of Ca²⁺ release in HT29 cells.

| Compound No. | R | EC$_{50}$ (μM) |
|---|---|---|
| 2 | 3-(NHCH2-C6H4)-C(O)NH-CH(CH2CH2NH2)-CONH2 | 0.2 |
| 3 | NHCH2-phenyl | 30 |
| 4 | NHCH2-(4-OMe-C6H4) | 10 |
| 5 | NHCH2-(2-Cl-C6H4) | 10 |
| 6 | NHCH2-(2-F-C6H4) | 30 |
| 7 | NHCH2-(3-F-C6H4) | 40 |
| 8 | NHCH2-(4-F-C6H4) | 40 |
| 9 | NHCH2-(2-NO2-C6H4) | 10 |
| 10 | 4-(4-F-C6H4)-piperazin-1-yl | 10 |
| 11 | 6,7-dimethoxy-1,2,3,4-tetrahydroisoquinolin-2-yl | 5-10 |
| 12 | 4-phenyl-4-acetamido-piperidin-1-yl | 1-6 |

TABLE 6

Biological Activity for representative PAR2 Ligands as Agonists or Partial Agonists of Ca²⁺ release in HT29 cells.

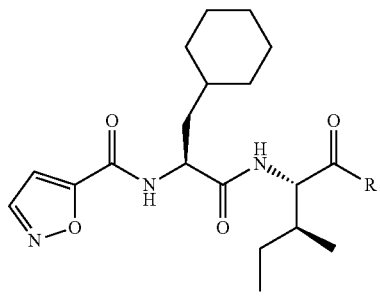

| | | |
|---|---|---|
| 13 | 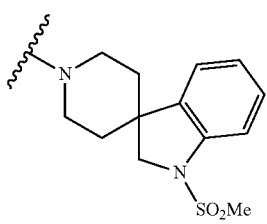 [SMILES: *N1CCC2(CC1)CN(S(C)(=O)=O)c1ccccc12] | 1.8 |
| 14 | 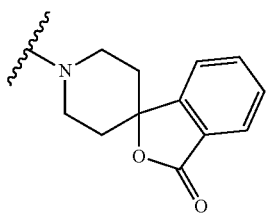 [SMILES: *N1CCC2(CC1)OC(=O)c1ccccc12] | 1.3 |
| 15 | 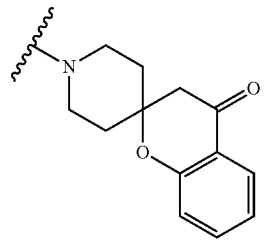 [SMILES: *N1CCC2(CC1)CC(=O)c1ccccc1O2] | 0.76 |
| 16 | 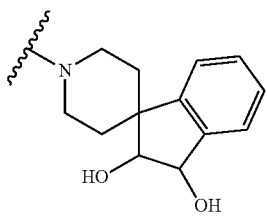 [SMILES: *N1CCC2(CC1)c1ccccc1C(O)C2O] | 5-7 |
| 17 | 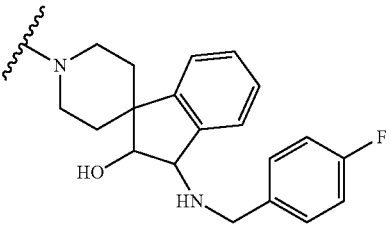 [SMILES: *N1CCC2(CC1)c1ccccc1C(NCc1ccc(F)cc1)C2O] | 20 |

Example 13

Determination of PAR2 Agonist Inhibition (Antagonism)

The ability of compounds of the present invention to inhibit the activation of PAR2 by trypsin or a synthetic PAR2 agonist is determined by intracellular calcium release assays as described above for Example 12.

The cells are prepared as outlined above then treated with the 'putative' antagonist 30 min prior to the addition of either trypsin or a synthetic agonist at a concentration equal to the agonists $EC_{80}$. The ability of compounds of the present invention to inhibit the activation of PAR2 is exemplified below in Tables 7, 8 and 9. Additionally, graphical representations of the above mentioned antagonist assays for the PAR2 antagonists represented by the synthetic examples (18, 24, 26, 27, 30, 39 and 42) are shown in FIGS. 2 to 8 and explained in detail below.

Figure 2:
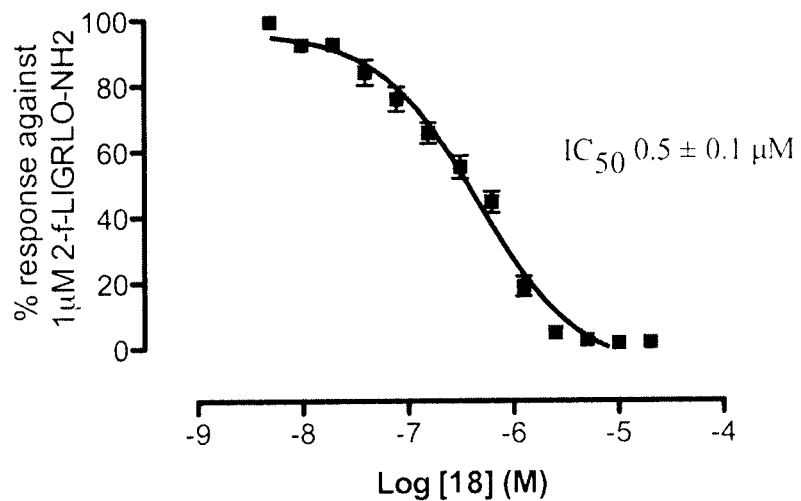
FIG. 2: Graphical representation of the concentration dependent inhibition of intracellular $Ca^{2+}$ release in HT29 cells by the PAR2 antagonist 18.
Figure 2:
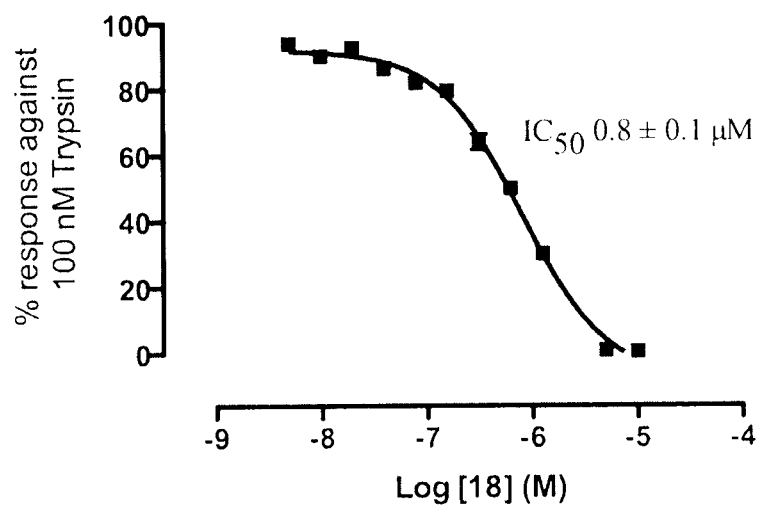

PAR2 ligand 18. A graphical representation of the inhibition of intracellular $Ca^{2+}$ release in HT29 cells by PAR2 antagonist 18 is shown in FIG. 2. Compound 18 was pre-incubated with HT29 cells for 30 min at room temperature prior to the experiment. The cells were then treated with 1 µM of the PAR2 agonist 2f-LIGRLO-NH₂ (FIG. 2A, n=5) or 100 nM Trypsin (FIG. 2B, n=1). Each data point represents mean±SEM. Net changes in fluorescence were calculated as a percentage relative to the maximum response given 1 µM 2f-LIGRLO-NH₂ or 100 nM Trypsin. Changes in fluorescence (% response) were plotted against logarithmic compound concentrations. The half maximal inhibitory concentration ($IC_{50}$) values were derived from the dose response curve using a nonlinear regression curve in Graphpad Prism v5.

Figure 3:
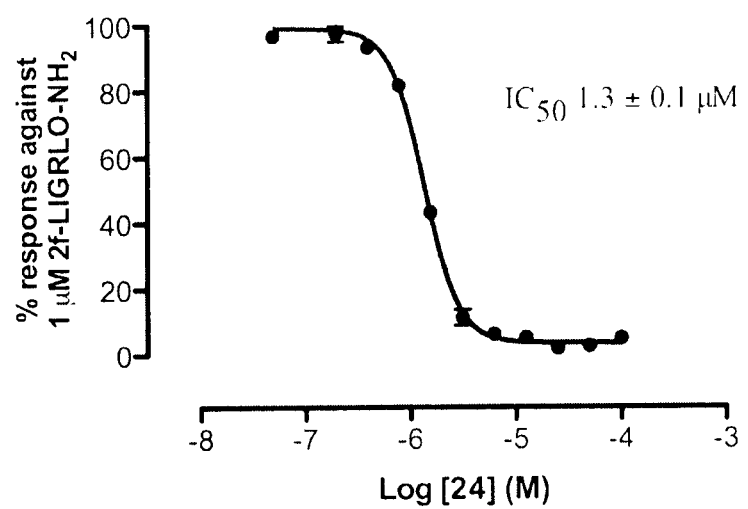
FIG. 3: Graphical representation of the concentration dependent inhibition of intracellular $Ca^{2+}$ release in HT29 cells by the PAR2 antagonist 24.

PAR2 ligand 24. A graphical representation of the inhibition of intracellular $Ca^{2+}$ release in HT29 cells by PAR2 antagonist 24 is shown in FIG. 3 (n=1). Compound 24 was pre-incubated with HT29 cells 30 min at room temperature prior to the experiment. The cells were then treated with 1 µM of the PAR2 agonist 2f-LIGRLO-NH₂. Each data point represents mean±SEM. Net changes in fluorescence were calculated as a percentage relative to the maximum response given 1 µM 2f-LIGRLO-NH₂. Changes in fluorescence (% response) were plotted against logarithmic compound concentrations. The half maximal inhibitory concentration ($IC_{50}$) values were derived from the dose response curve using a nonlinear regression curve in Graphpad Prism v5.

Figure 4:
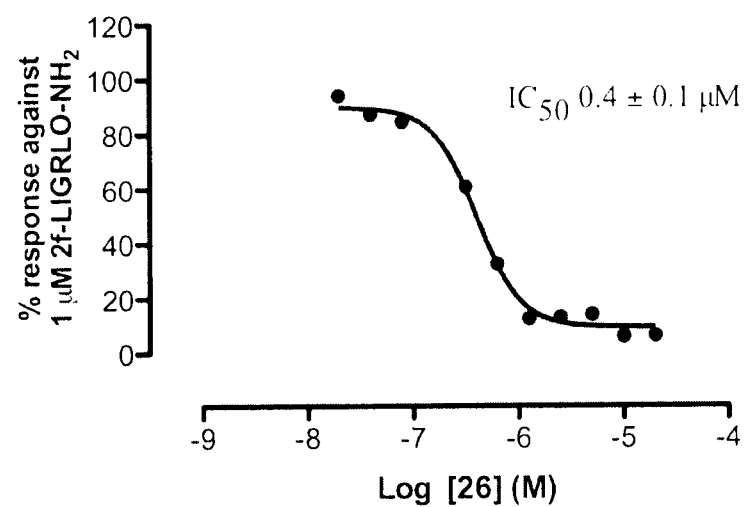
FIG. 4: Graphical representation of the concentration dependent inhibition of intracellular $Ca^{2+}$ release in HT29 cells by the PAR2 antagonist 26.

PAR2 ligand 26. A graphical representation of the inhibition of intracellular $Ca^{2+}$ release in HT29 cells by PAR2 antagonist 26 is shown in FIG. 4 (n=1). Compound 26 was pre-incubated with HT29 cells 30 min at room temperature prior to the experiment. The cells were then treated with 1 µM of the PAR2 agonist 2f-LIGRLO-NH₂. Each data point represents mean±SEM. Net changes in fluorescence were calculated as a percentage relative to the maximum response given 1 µM 2f-LIGRLO-NH₂. Changes in fluorescence (% response) were plotted against logarithmic compound concentrations. The half maximal inhibitory concentration ($IC_{50}$) values were derived from the dose response curve using a nonlinear regression curve in Graphpad Prism v5.

Figure 5:
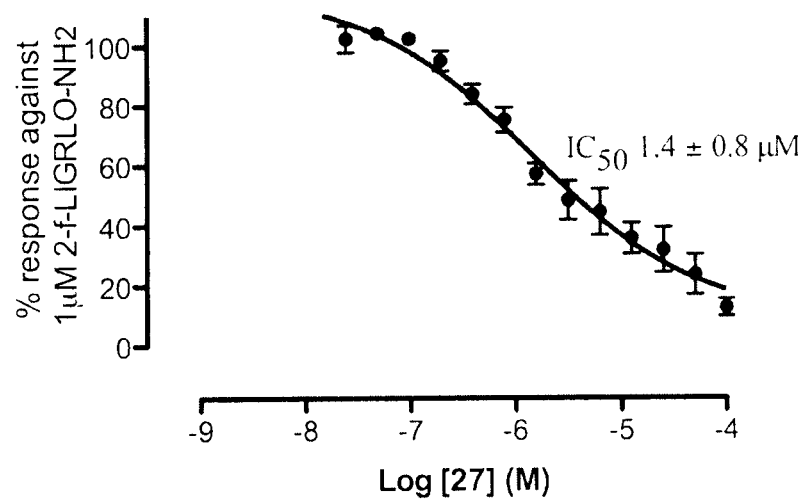
FIG. 5: Graphical representation of the concentration dependent inhibition of intracellular $Ca^{2+}$ release in HT29 cells by the PAR2 antagonist 27.

PAR2 ligand 27. A graphical representation of the inhibition of intracellular $Ca^{2+}$ release in HT29 cells by PAR2 antagonist 27 is shown in FIG. 5 (n=2). Compound 27 was pre-incubated with HT29 cells 30 min at room temperature prior to the experiment. The cells were then treated with 1 µM of the PAR2 agonist 2f-LIGRLO-NH₂. Each data point represents mean±SEM. Net changes in fluorescence were calculated as a percentage relative to the maximum response given 1 µM 2f-LIGRLO-NH₂. Changes in fluorescence (% response) were plotted against logarithmic compound concentrations. The half maximal inhibitory concentration (IC$_{50}$) values were derived from the dose response curve using a nonlinear regression curve in Graphpad Prism v5.

Figure 6:
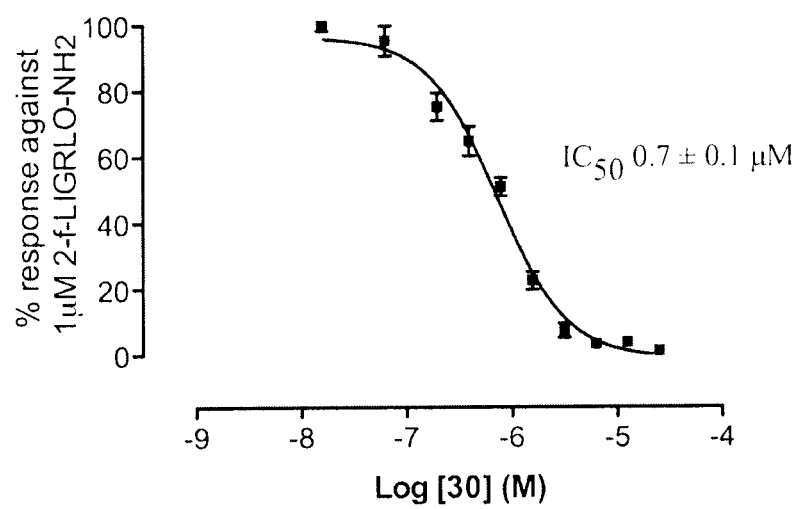
FIG. 6: Graphical representation of the concentration dependent inhibition of intracellular $Ca^{2+}$ release in HT29 cells by the PAR2 antagonist 30.

PAR2 Ligand 30. A graphical representation of the inhibition of intracellular Ca$^{2+}$ release in HT29 cells by PAR2 antagonist 30 is shown in FIG. 6 (n=8). Compound 30 was pre-incubated with HT29 cells 30 min at room temperature prior to the experiment. The cells were then treated with 1 μM of the PAR2 agonist 2f-LIGRLO-NH$_2$. Each data point represents mean±SEM. Net changes in fluorescence were calculated as a percentage relative to the maximum response given 1 μM 2f-LIGRLO-NH$_2$. Changes in fluorescence (% response) were plotted against logarithmic compound concentrations. The half maximal inhibitory concentration (IC$_{50}$) values were derived from the dose response curve using a nonlinear regression curve in Graphpad Prism v5.

Figure 7:
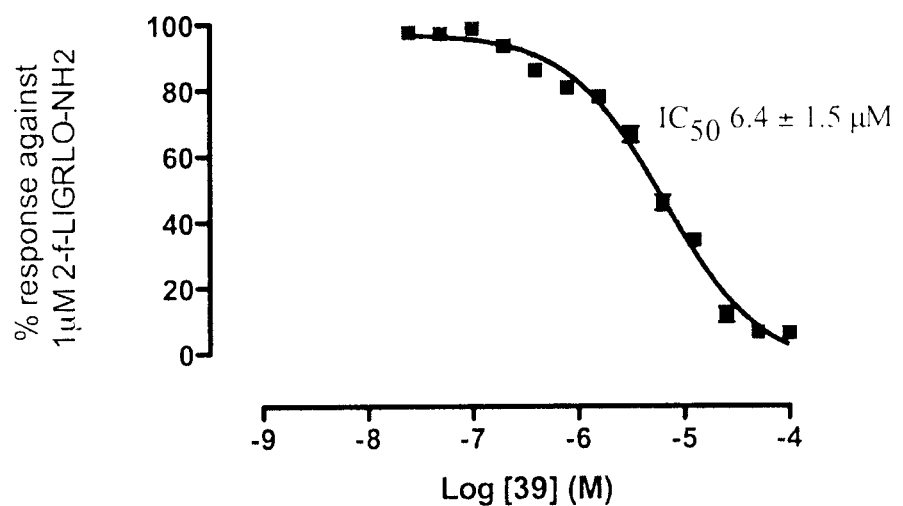
FIG. 7: Graphical representation of the concentration dependent inhibition of intracellular $Ca^{2+}$ release in HT29 cells by the PAR2 antagonist 39.

PAR2 Ligand 39. A graphical representation of the inhibition of intracellular Ca$^{2+}$ release in HT29 cells by PAR2 antagonist 39 is shown in FIG. 7 (n=1). Compound 39 was pre-incubated with HT29 cells 30 min at room temperature prior to the experiment. The cells were then treated with 1 μM of the PAR2 agonist 2f-LIGRLO-NH$_2$. Each data point represents mean±SEM. Net changes in fluorescence were calculated as a percentage relative to the maximum response given 1 μM 2f-LIGRLO-NH$_2$. Changes in fluorescence (% response) were plotted against logarithmic compound concentrations. The half maximal inhibitory concentration (IC$_{50}$) values were derived from the dose response curve using a nonlinear regression curve in Graphpad Prism v5.

Figure 8:
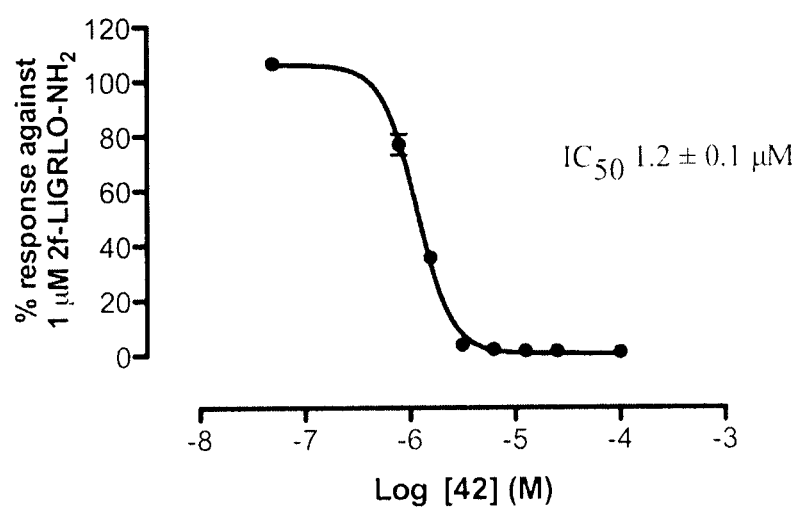
FIG. 8: Graphical representation of the concentration dependent inhibition of intracellular $Ca^{2+}$ release in HT29 cells by the PAR2 antagonist 42.

PAR2 Antagonist 42. A graphical representation of the inhibition of intracellular Ca$^{2+}$ release in HT29 cells by PAR2 antagonist 42 is shown in FIG. 8 (n=1). Compound 42 was pre-incubated with HT29 cells 30 min at room temperature prior to the experiment. The cells were then treated with 1 μM of the PAR2 agonist 2f-LIGRLO-NH$_2$. Each data point represents mean±SEM. Net changes in fluorescence were calculated as a percentage relative to the maximum response given 1 μM 2f-LIGRLO-NH$_2$. Changes in fluorescence (% response) were plotted against logarithmic compound concentrations. The half maximal inhibitory concentration (IC$_{50}$) values were derived from the dose response curve using a nonlinear regression curve in Graphpad Prism v5.

TABLE 7

Benzylamine ligands that can Antagonise PAR2 Activation as Measured by Inhibiting Ca$^{2+}$ Release in HT29 cells.

| Compound No. | R | IC$_{50}$ (μM) |
|---|---|---|
| 18 | 2-OMe-benzyl | 0.5 ± 0.1 |
| 19 | 3-OMe-benzyl | 0.5 ± 0.1 |
| 20 | 2-Me-benzyl | 0.5 ± 0.1 |
| 21 | 2-OEt-benzyl | 0.7 ± 0.1 |
| 22 | 2-OPr-benzyl | 2.0 |
| 23 | 2-OBu-benzyl | 40 |
| 24 | 2-OiPr-benzyl | 1.3 ± 0.1 |
| 25 | 2-OsBu-benzyl | 1.6 ± 0.4 |

TABLE 7-continued
Benzylamine ligands that can Antagonise PAR2 Activation as Measured by Inhibiting Ca²⁺ Release in HT29 cells.
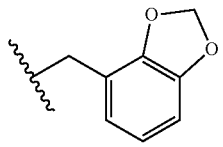 [SMILES: *Cc1cccc2c1OCO2]
| Compound No. | R | IC$_{50}$ (µM) |
|---|---|---|
| 26 | 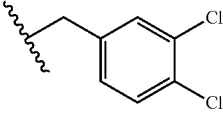 [SMILES: *Cc1ccc(Cl)c(Cl)c1] | 0.4 ± 0.1 |
| 27 | 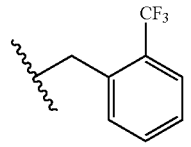 [SMILES: *Cc1ccccc1C(F)(F)F] | 1.4 ± 0.8 |
| 28 | 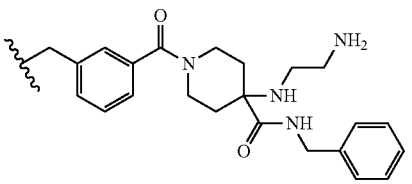 [SMILES: *Cc1cccc(C(=O)N2CCC(NCCN)(C(=O)NCc3ccccc3)CC2)c1] | 1-2 |
| 29 | 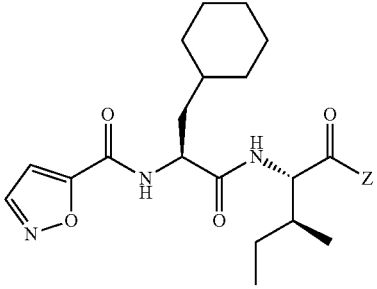 | 0.7 |
TABLE 8
Representative Piperidine Ligands that can Antagonise of PAR2 Activation as Measured by Inhibiting Ca²⁺ Release in HT29 Cells.
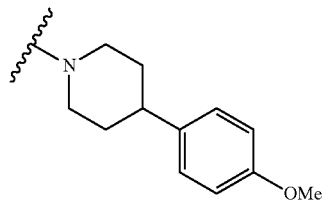 [SMILES: *N1CCC(c2ccc(OC)cc2)CC1]
| Compound No. | Z | IC$_{50}$ (µM) |
|---|---|---|
| 30 | 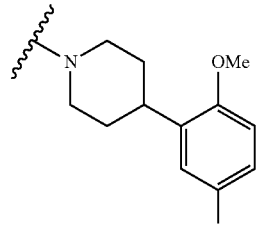 | 0.7 ± 0.1 |
| 31 | 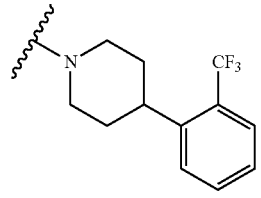 [SMILES: *N1CCC(c2ccccc2C(F)(F)F)CC1] | 10 |
| 32 | 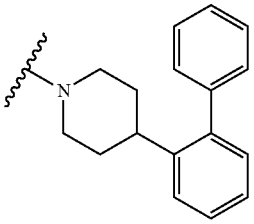 [SMILES: *N1CCC(c2ccccc2-c2ccccc2)CC1] | 5-10 |
| 33 | | 10 |
| 34 | | 25 |

TABLE 8-continued

Representative Piperidine Ligands that can Antagonise of PAR2 Activation as Measured by Inhibiting Ca$^{2+}$ Release in HT29 Cells.

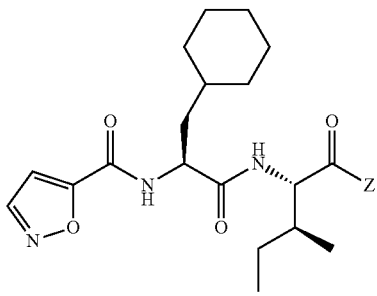

| Compound No. | Z | IC$_{50}$ (μM) |
|---|---|---|
| 35 | <br>(N-piperidine-4-CH$_2$-phenyl) | 8 |
| 36 | <br>(piperidine-2-C(O)NH-tBu) | 8.6 ± 2.6 |

TABLE 8-continued

Representative Piperidine Ligands that can Antagonise of PAR2 Activation as Measured by Inhibiting Ca$^{2+}$ Release in HT29 Cells.

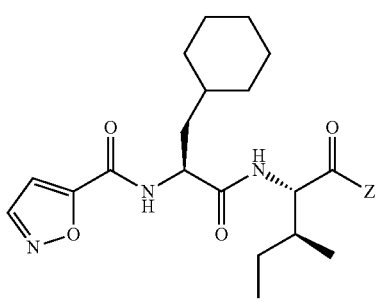

| Compound No. | Z | IC$_{50}$ (μM) |
|---|---|---|
| 37 | <br>(N-methylpiperidine-spiro-chroman) | 5-10 |
| 38 | <br>(N-piperidine-3-NH-(3-CF$_3$-phenyl)) | 6 |

TABLE 9

Other Representative PAR2 Ligands that can Antagonise PAR2 Activation as Measured by Inhibiting Ca$^{2+}$ Release in HT29 Cells.

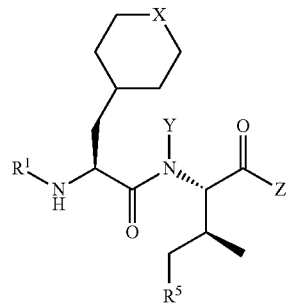

| Compound No. | R$^1$ | X | Y | R$^5$ | Z | IC$_{50}$ (μM) |
|---|---|---|---|---|---|---|
| 39 | isoxazole-5-C(O)- | CH$_2$ | H | Me | N(Me)-CH$_2$-(2-OMe-phenyl) | 6.4 |
| 40 | isoxazole-5-C(O)- | CH | H | OMe | NH-CH$_2$-(2-OMe-phenyl) | 1.3 |

TABLE 9-continued
Other Representative PAR2 Ligands that can Antagonise PAR2 Activation as Measured by Inhibiting $Ca^{2+}$ Release in HT29 Cells.
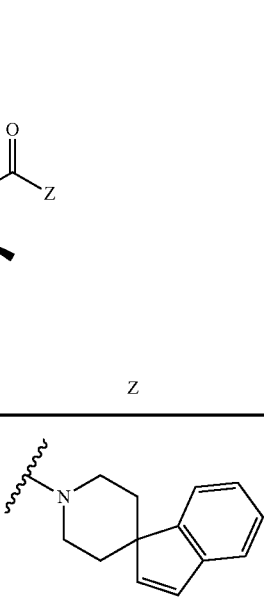
| Compound No. | $R^1$ | X | Y | $R^5$ | Z | $IC_{50}$ (μM) |
|---|---|---|---|---|---|---|
| 41 | H | CH$_2$ | H | Me | 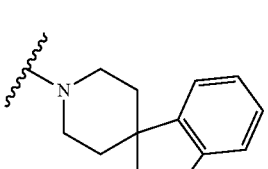 | 17 |
| 42 | 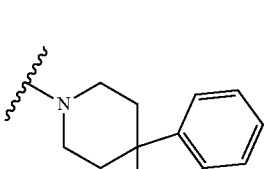 | CH$_2$ | H | Me | 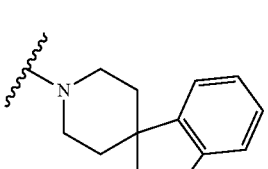 | 1.2 |
| 43 | 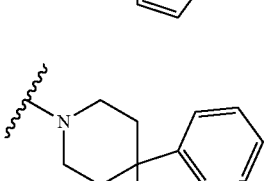 | O | H | Me | 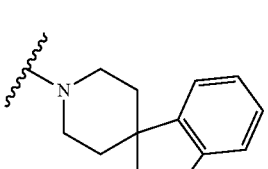 | 60 |
| 44 | 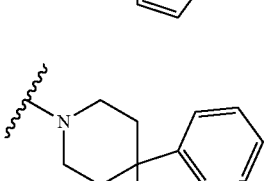 | CH$_2$ | H | OMe | 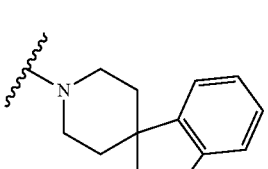 | 1 |
| 45 | 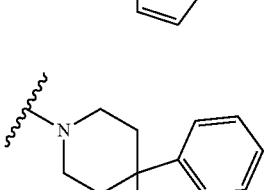 | CH$_2$ | H | Me | 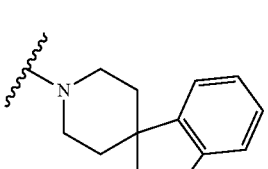 | 15 |
| 46 | 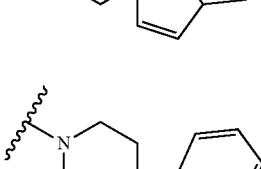 | CH$_2$ | H | Me | 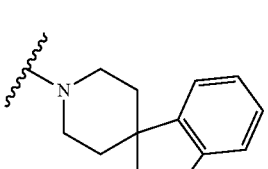 | 25 |

TABLE 9-continued

Other Representative PAR2 Ligands that can Antagonise PAR2 Activation
as Measured by Inhibiting $Ca^{2+}$ Release in HT29 Cells.

| Compound No. | $R^1$ | X | Y | $R^5$ | Z | $IC_{50}$ (μM) |
|---|---|---|---|---|---|---|
| 47 | (imidazolyl-C(O)-) | $CH_2$ | H | Me | (spiro-indene-piperidinyl) | 10 |
| 48 | (piperidin-4-yl-C(O)-) | $CH_2$ | H | Me | (spiro-indene-piperidinyl) | 50 |
| 49 | (5-oxopyrrolidin-2-yl-C(O)-) | $CH_2$ | H | Me | (spiro-indene-piperidinyl) | 25 |
| 50 | (pyrrolidin-2-yl-C(O)-) | $CH_2$ | H | Me | (spiro-indene-piperidinyl) | 50 |
| 51 | H | $CH_2$ | Me | Me | (spiro-indene-piperidinyl) | 5-10 |

Example 14

Assessment of the Anti-Inflammatory Activity of the Compounds of the Present Invention The ability of compounds of the present invention to ameliorate the symptoms associated with both acute and chronic inflammatory disorders may be determined via a number of animal models well known to those skilled in the art, general examples of which are provided below.

Pharmacokinetics

Animals

Male and female Wistar rats (aged 8-9 weeks, 200-250 g and 250-300 g respectively) are generally maintained in a 12 h light/dark cycle according to the standard of holding facility with food and water provided.

Short Term Pharmacokinetics

Male Wistar rats are surgically implanted with a jugular vein catheter. Volumes of blood are collected from the indwelling catheter in freely moving animals. Blood samples (heparinised) are collected 5 minutes prior to the administration of a compound of the present invention (10 mg/kg p.o.) and 30 min, 1-6, 8 and 24 h post-administration. Bloods are centrifuged at 8 K rpm for 5 min, and plasma diluted 3 times (v/v) with acetonitrile and stored at −80° C. for later use.

Long-Term Pharmacokinetics

A subset of animals not implanted with a catheter are given an oral dose of a compound of the present invention four days consecutively (n=6). On the fifth day, rats are euthanised ($CO_2$ inhalation) and plasma is collected via cardiac puncture. Cerebrospinal fluid (CSF) is collected from the cisterna magna and intraperitoneal adipose is collected. Clean and blood free CSF samples are diluted twice in acetonitrile, vortexed and centrifuged at 8 K rpm for min. Adipose is homogenised in equal volume (ml/g) Millipore water. A portion of the sample is diluted in acetonitrile (3×w/v) and stored at −80° C. for later use.

Preparation of Fluid Samples

Standard curve: each stock solution comprising a compound of the present invention is prepared in acetonitrile at 9.15, 4.57, 0.92, 0.46, 0.09, 0.046, 0.009 and 0.005 μM. A 200 μL sample of fresh plasma from non-drug treated rat is transferred into 200 μL of stock solution, followed by addition of 400 μL of acetonitrile. The mixture is vortexed for 1 min. sonicated for 10 min centrifuged at 13 K rpm for 5 min and stored at −80° C. for later use.

Supernatants are diluted in Millipore water (3× volume) and terl-butyl methyl ether (TBME, CHIROMASOLV® Plus, for HPLC, 99.9%, from Sigma Aldrich, 3× volume). Samples are vortexed and left on dry ice until the water/acetonitrile phase is frozen. The organic phase is decanted into a microfuge tube and concentrated using a rotational vacuum concentrator (Christ Beta-RVC, supplied by Quantum Scientific). 100 μL of acetonitrile is added to the residue, vortexed and immediately analysed by LCMS/MS.

Acute Inflammatory Model: PAR2-induced Paw Oedenma

Figure 9:
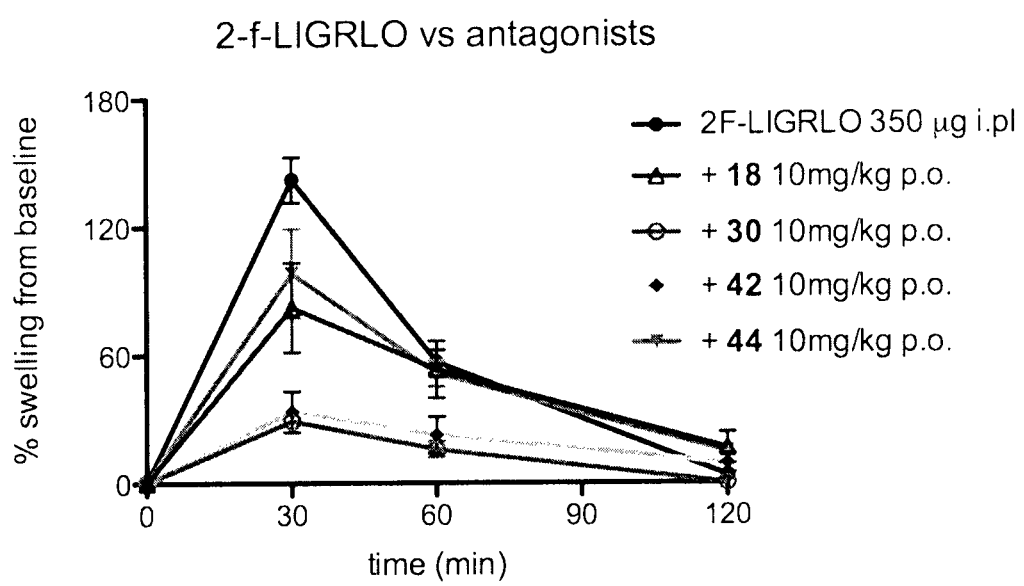
FIG. 9. Graphical representation of the ability of PAR2 antagonists 18, 30, 42, 44 to attenuate experimental paw oedema. Antagonist 18, 30, 42 or 44 (10 mg/kg p.o, in olive oil, n=3) reduced the paw swelling induced by 2-f-LIGRLO-NH$_2$ (350 µg/paw, 2 h after oral dose of the antagonist).

The methods used are based on those previously described (Kelso, E. B., et al. *Arthritis Rheum* 2007, 56, 765-71; Kelso, E. B., et al *Pharmacol Exp Ther* 2006, 316, 1017-24: and Vergnolle. N. *J Immunol* 1999, 163, 5064-9). Male Wistar rats (n=3 per group) are used. Briefly, rats are given either 5 or 10 mg/kg of a compound of the present invention (p.o. via gavage in olive oil, approx. 500 μL, weight adjusted). Control animals receive only olive oil (500 μL p.o.). Two hours later, the PAR2 agonist 2-furoyl-LIGRLO (350 μg/paw in saline, 100 μL) is injected into the plantar surface (i.pl.) of the right paw pad using a 30 G needle. The left paw acts as a control, receiving saline only. Paw thickness and width are measured after 30 minutes and hourly using digital calipers (World Precision Instruments, USA) and swelling is calculated in area ($mm^2$; thickness multiplied by width) and expressed as a percentage change from baseline of each individual paw. Results for exemplary PAR2 ligands 18, 30, 42 and 44 are illustrated in FIG. 9.

Acute Inflammatory Model: λ-carrageenan-induced Paw Oedema

Methods used are based on that previously described (Kelso, E. B., et al., *J Pharmacol Exp Ther* 316:1017-1024: and Flick, M. J., et al *J Clin Invest* 117:3224-3235). Male Wistar rats (n=4 per group) are used. Briefly, rats are given 10 mg/kg of a compound of the present invention (p.o. via gavage in olive oil, 500 μL). Control animals receive only olive oil (500 μL p.o.). Thirty minutes later, λ-carrageenan (1% w/v in saline, 100 μL) is injected into the plantar surface (i.pl.) of the right paw pad using a 30 G needle. The left paw acts as a control, receiving saline only, similar to that previously described. Paw width and thickness are measured at 1-6, 8 and 24 h. Data is expressed as a normalised change in area ($mm^2$) from baseline.

Chronic Inflammatory Model: Collagen-Induced Arthritis

Protocols are based on those previously described (Earp. J. C. et al. *Biopharm Drug Dispos* 2008; Lin, H. S., et al., *Br J Pharmacol* 2007, 150, 862-72: Nishikawa, M., et al. *Arthritis Rheum* 2003, 48, 2670-81; and Olofsson, P., et al. *Arthritis Rheumn* 2003, 48. 2332-42). Female Wistar rats are used (200-250 g, n=14 total). Immunisation of collagen begins on Day 0, where 200 μg of collagen is administered in 200 μL (50:50 0.05M acetic acid and Freund's incomplete adjuvant) subcutaneously into the base of the tail using a 30 G needle. Sham animals receive the vehicle (50:50 0.05M acetic acid and Freund's incomplete adjuvant) with collagen omitted. Seven days later (day 7), the same treatment is given as a booster. A compound of the present invention (10 mg/kg in olive oil, 500 μl, p.o. weight adjusted) is given daily to test subjects from day 7 onwards, arthritic control and sham animals receive olive oil vehicle by gavage only. Paw measurements (as described above), body weight, clinical score and mechanical nociceptive thresholds are measured every second day from Day 10 through Day 28. Only hind paws are measured. Swelling is calculated in area ($mm^2$) and expressed as a percentage change from the baseline. A paw is considered arthritically effected when the swelling of an individual paw becomes greater than 20%, which is the maximal paw area change observed in the sham group (i.e. the growth that is expected due to the experimental time course alone).

Clinical Measurements.

Clinical score is measured observationally by an expert researcher, incorporating the following constraints: Mobility: 0: No limp, full hind limb weight bearing. 1: Mild limp, reduced mobility. 2: Reduced/no weight bearing on one hind limb, reduced mobility. 3: No weight bearing on either (two) hind limb, little mobility. Inflammation: 0: No redness, no swelling, and no arthritic symptoms. 1: Mild redness and swelling. 2: Arthritic symptoms appearing (clutching of toes) moderate swelling and redness. 3: Severe swelling and redness, severe arthritic symptoms (loss of plantar reflex, clutching of toes, supination and adduction of rear paws during handling). Discomfort/pain; 0: No vocalisation, normal behaviour. 1: Mild vocalisation only. 2: Increased vocalisations and mild flinching during handling. 3: Spontaneous vocalisation during movement (no handling required for instigation). Clinical scores are expressed as a sum of the three scores multiplied by the number of paws involved (maximum total score of 18, see above).

Histopalhology and Joint Health Assessment.

At an end point (day 28), rats are euthanized with $CO_2$. Hind paws are skinned, amputated and placed in 4% paraformaldehyde (pH 7.4) for seven days at 4° C. Paws are decalcified for 72 h (10% HCl; 0.18% (w/v) EDTA: 0.09% (w/v) tartrate in $H_2O$) and embedded in paraffin wax for histological analysis. Sections are cut at 10 μm and stained with haematoxylin and eosin (H&E), Masson's Trichrome stain (MTC) or Alcian blue/Safrannin-O using standard protocols. The tibial/talus/calcaneal joints of at least 6 sections are imaged per animal are assessed/stain technique and scored by an expert blinded to the treatment.

H&E sections are scored using the following modified guide (Woodruff. T. M. et al. *Arthritis Rheum* 2002, 46, 2476-

85) as follows. Oedema; 0: healthy tissue, no plasma cell invasion. 1: Mild plasma cell invasion into the extra-synovial space. 2: Moderate plasma cell invasion into the extra-synovial space, beginning to invade synovium. 3: Severe plasma cell invasion, appearance of rice bodies and inflammatory cells in the synovium. Synovial hyperplasia; 0: Normal tissue. 1: Mild synovial swelling. 2: Moderate synovial swelling. 3: Severe swelling and growth of synovial space. Cartilage/bone erosion: 0: Normal cartilage. 1: Mild adhesion of inflammatory cells to the articular cartilage. 2: Moderate adhesion of inflammatory cells beginning to erode the first layer of articular cartilage. 3: Severe inflammatory cell adhesion and erosion of cartilage layers, perichondrum and underlying bone. Pannus formation; 0: No pannus. 1: Pannus beginning to form. 2: Pannus entering the synovium. 3: Pannus beginning to erode cartilage/bone. Total histopathological scores are expressed as a sum of all scores (total score of 12). Collagen loss is scored qualitatively in Mason's Trichrome stained sections and according to the relative proportion of red stain (loss of Aniline blue) of the articular surface of the tibia similar to previously described. 0: no red stain on articular surface. 1: 0-25%, of surface appearing red, 2: 25-50% surface appearing red, 3: >50% of articular surface stained red (maximal score of 3). Differential Alcian blue/Safrannin-O staining determined mast cell activation state, similar to that previously described. Each section is imaged at 100× in regions both superior and inferior to the tibial/talus joint. At least 6 sections are imaged per animal (>12 sections analysed/rat). Cells are counted from the images with the aid of ImageJ 1.42q software. Red cells without the presence of blue are considered inactive. Cells with the appearance of blue stain, but still with some degree of red staining, are considered active. Cells with no visible red staining (only blue) are considered degranulated.

Example 15

Assessment of the Anti-Proliferative Activity of the Compounds of the Present Invention The ability of compounds of the present invention to attenuate aberrant cellular proliferation may be determined via a number of assays well known to those skilled in the art, including, but not limited to the general example provided below.
Tritiated Thymidine Incorporation Into Cellular DNA.

Primary human kidney tubule cells are grown in 48 well plates in hormonally defined serum free DMEM/F12 until 90% confluent. They are then washed twice with DMEM without added growth factors and cultured for a further for 24 h in this basic media. At this time a compound of the present invention in serum free DMEM is added to the cells, then they are cultured for a further 24 hours. [methyl-$^3$H]-thymidine (TRA120, GE Healthcare), 4 µCi. (0.15 MBq) per mL of media, is added for the last six hours of culture. At the end of the test period, the media is removed. (and stored at −80° C. for measurement of cytokine release), the cells are washed twice with ice cold PBS and then three times with ice cold 10% trichloroacetic acid for 10 minutes. The cells are washed one more time with methanol. Cell layers are then air dried and solubilised by the addition of 200 µL of 0.3M NaOH containing 1% sodium dodecylsulphate for 1 hour at 37° C. After mixing 50 µL is removed and placed in 1 mL of scintillation fluid for counting in a beta-counter. Raw dpms are multiplied by 4 and divided by 1000 to give plotted values of cellular proliferation.

Example 16

Stability of the Compounds of the Present Invention in Rat Plasma and Liver Homogenate Tissue Fluids Blood and liver is collected form non-drug dosed male and female Wistar rats (aged 8-9 weeks, 200-250 g and 250-300 g respectively). Bloods are centrifuged at 8 K rpm for 5 min. Plasma are pooled and stored at −80° C. for later use. The rat livers are homogenized, diluted with three volumes of PBS, cloth filtered. The filtrate is used directly for stability studies.
Preparation of Fluid Samples Each compound is dissolved in DMSO to make 5 mM stock solution. 10 µL of the stock is diluted with either rat plasma or liver homogenate (490 µL) to make up a starting concentration of 10 µM (triplicates). The mixtures are vortexed and incubated at 37° C. At each time point of 0, 30, 60 and 180 minutes, 100 µL of the mixture is taken and diluted with 300 µL of acetonitrile. The mixture is vortexed and centrifuged. 350 µL of the liquid is transferred into a microfuge tube and concentrated using a rotational vacuum concentrator (Christ Beta-RVC, supplied by Quantum Scientific). 100 µL of acetonitrile water (9:1, v/v) is added to the residue, vortexed and immediately analysed by LCMS/MS. Data from these experiments are expressed as percent of peak area recorded from the LCMS/MS trace at time zero ($t_0$).

Figure 10:
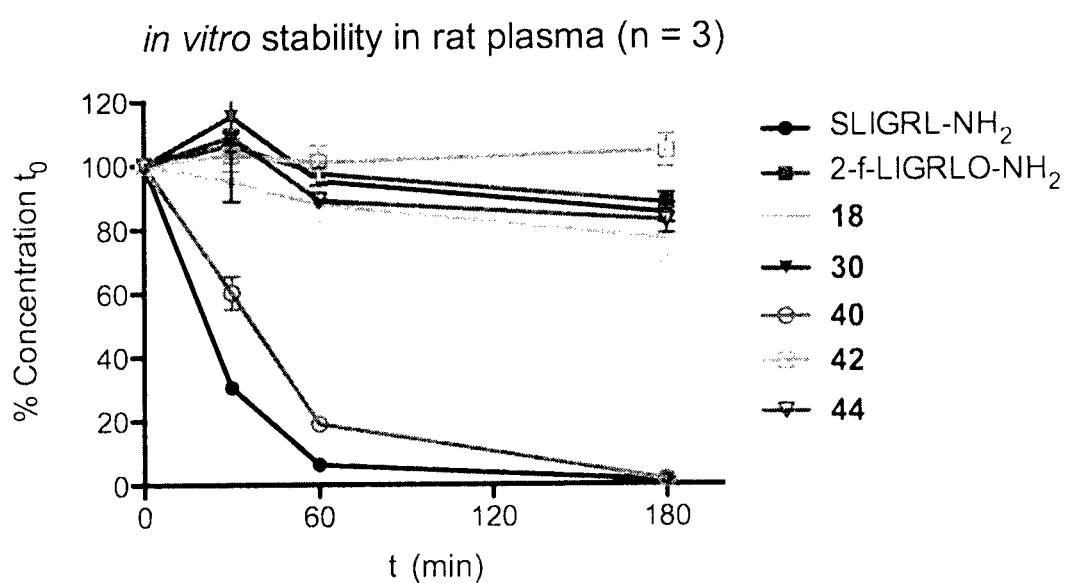
FIG. 10. Graphical representation of the stability of PAR2 antagonists (18, 30, 40, 42 and 44) compared to the known peptide agonists SLIGRL-NH$_2$ and 2-f-LIGRLO-NH$_2$ in rat plasma (derived from non-drug dosed Wistar rats).
Figure 11:
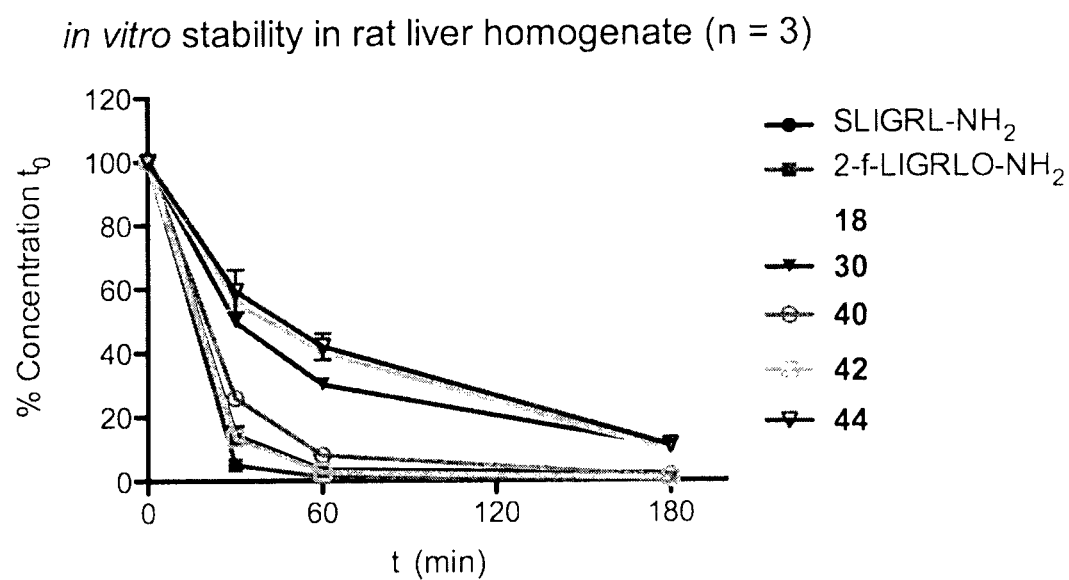
FIG. 11. Graphical representation of the stability of PAR2 antagonists (18, 30, 40, 42 and 44) compared to the known peptide agonists SLIGRL-NH$_2$ and 2-f-LIGRLO-NH$_2$ in rat liver homogenate (derived from non-drug dosed Wistar rats).

In general, the compounds (18, 30, 42 and 44) are stable in rat plasma (over 80% present after 3 h) and decomposed to varied degree in rat liver homogenate (FIGS. 10 and 11).

The results support the hypothesis that the compounds are mainly metabolized in liver.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The claims defining the invention are as follows:
1. A compound of the formula (I):

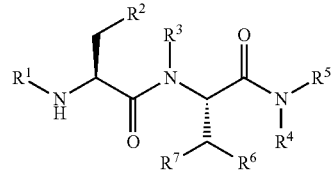

wherein
$R^1$ is —C(O)$R^8$;
$R^8$ is a 5- or 6-membered unsaturated heterocyclic ring comprising 1 to 3 heteroatoms selected from N and O, optionally substituted with one or more substituents selected from alkyl, alkoxy, amine, aminoalkyl, amidoalkyl, halo, hydroxy, trihaloalkyl, trihaloalkoxy, and phenyl, wherein the phenyl group is optionally substituted with 1 to 3 substituents selected from alkyl, alkoxy, hydroxy, halo, nitro, trihaloalkyl, and trihaloalkoxy;

$R^2$ is an aromatic or aliphatic $C_3$-$C_8$cyclic group or $C_3$-$C_8$heterocyclic group comprising 1 to 3 heteroatoms selected from N and O, wherein the $C_3$-$C_8$cyclic group or $C_3$-$C_8$heterocyclic group is optionally substituted with one or more substituents selected from alkyl, amine, and hydroxy, or the cyclic group or heterocyclic group is fused with an optionally substituted aromatic or aliphatic $C_3$-$C_8$cyclic group or $C_3$-$C_8$heterocyclic group;

$R^3$ is hydrogen or $C_1$-$C_6$alkyl;

$R^4$ is hydrogen, $C_1$-$C_6$alkyl, aminoalkyl, or amidoalkyl;

$R^5$ is a benzyl group optionally substituted with alkyl, aminoalkyl, alkoxy, $C_4$-$C_7$heterocycle, hydroxy, halo, nitro, dioxalane, trihaloalkyl, trihaloalkoxy or —C(O)NHCHR$^9$R$^{10}$;

$R^9$ is —C(O)NH$_2$; and $R^{10}$ is a $C_2$-$C_5$aminoalkyl;

or $R^4$ and $R^5$ combined, together with the nitrogen to which they are attached, form piperidine, optionally substituted but not fused with a group selected from phenyl, benzyl, aminoaryl, amidoalkyl or a heterocycle, or piperidine is fused with an aromatic or aliphatic $C_3$-$C_8$heterocyclic group; wherein the phenyl, benzyl, aminoaryl, heterocycle or fused aromatic or aliphatic $C_3$-$C_8$heterocyclic group may be further substituted with 1 to 3 substituents selected from alkyl, alkylsulfonyl, alkoxy, aminoalkyl, aminoaryl, amidoalkyl, arylamine, hydroxy, halo, nitro, oxo, optionally substituted phenyl, optionally substituted piperidine, dioxalane, trihaloalkyl, and trihaloalkoxy; or the fused aromatic or aliphatic $C_3$-$C_8$heterocyclic group is fused with an additional $C_6$-$C_{10}$cyclic or $C_6$-$C_{10}$heterocyclic group;

$R^6$ is hydrogen or $C_1$-$C_6$alkyl;

$R^7$ is $C_1$-$C_6$alkyl, amino, hydroxy, alkoxy, aminoalkyl, amidoalkyl, saturated or unsaturated cycloalkyl, or heterocycle; or a salt thereof.

2. The compound according to claim 1, represented by the formula (Ia):

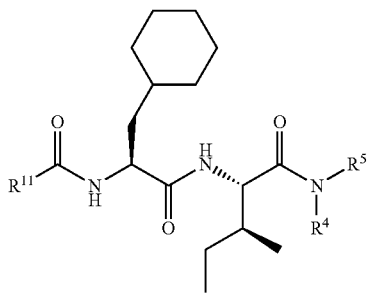

(Ia)

wherein $R^{11}$ is a 5- or 6-membered unsaturated heterocyclic ring comprising 1 to 3 heteroatoms selected from N and O, optionally substituted with one or more groups selected from alkyl and phenyl, wherein the phenyl group is optionally substituted with 1 to 3 substituents selected from alkyl, alkoxy, hydroxy, halo, nitro, trihaloalkyl and trihaloalkoxy;

$R^4$ is hydrogen, $C_1$-$C_6$alkyl, aminoalkyl or amidoalkyl;

$R^5$ is a benzyl group, optionally substituted with alkyl, aminoalkyl, alkoxy, $C_4$-$C_7$heterocycle, hydroxy, halo, nitro, dioxalane, trihaloalkyl, trihaloalkoxy or —C(O)NHCHR$^9$R$^{10}$;

$R^9$ is —C(O)NH$_2$; and $R^{10}$ is a $C_2$-$C_5$aminoalkyl;

or $R^4$ and $R^5$ combined, together with the nitrogen to which they are attached, form piperidine, optionally substituted but not fused with phenyl, benzyl, amidoalkyl or a heterocycle; wherein the phenyl, benzyl or heterocycle is optionally substituted with 1 to 3 substituents selected from alkyl, alkyloxy, aminoalkyl, amidoalkyl, hydroxy, halo, nitro, dioxalane, trihaloalkyl, and trihaloalkoxy; or a salt thereof.

3. The compound according to claim 1, represented by the formula (Ib):

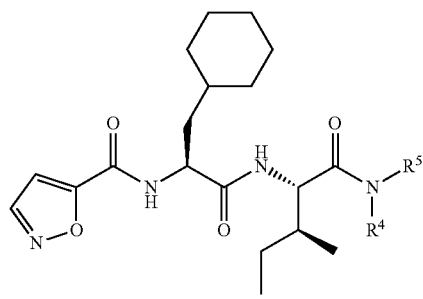

(Ib)

wherein $R^4$ is hydrogen, $C_1$-$C_6$alkyl, aminoalkyl or amidoalkyl;

$R^5$ is a benzyl group, optionally substituted with a group selected from alkyl, aminoalkyl, alkoxy, $C_4$-$C_7$heterocycle, hydroxy, halo, nitro, dioxalane, trihaloalkyl, trihaloalkoxy and —C(O)NHCHR$^9$R$^{10}$;

$R^9$ is —C(O)NH$_2$; and $R^{10}$ is a $C_2$-$C_5$aminoalkyl;

or $R^4$ and $R^5$ combined, together with the nitrogen to which they are attached, form piperidine, optionally substituted but not fused with a group selected from phenyl, benzyl, aminoaryl, amidoalkyl and a heterocycle, or piperidine is fused with an aromatic or aliphatic $C_3$-$C_8$heterocyclic group; wherein the phenyl, benzyl, heterocycle or fused aromatic or aliphatic $C_3$-$C_8$heterocyclic group is optionally substituted with 1 to 3 substituents selected from alkyl, alkylamide, alkyloxy, aminoalkyl, amidoalkyl, hydroxy, halo, nitro, dioxalane, trihaloalkyl, and trihaloalkyloxy; or a salt thereof.

4. The compound according to claim 1 represented by the formula (Ic):

(Ic)

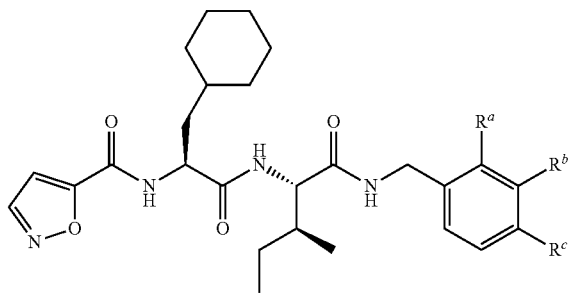

wherein
  $R^a$, $R^b$ and $R^c$ are each independently hydrogen, alkyl, aminoalkyl, alkoxy, $C_4$-$C_7$heterocycle, hydroxy, halo, nitro, trihaloalkyl, trihaloalkoxy or —C(O)NHCHR$^9$R$^{10}$;
  $R^9$ is —C(O)NH$_2$; and
  $R^{10}$ is a $C_2$-$C_5$aminoalkyl;
  or $R^a$ and $R^b$ or $R^b$ and $R^c$ combined form dioxalane;
or
  a salt thereof.

5. The compound according to claim 1, represented by the formula (Id):

(Id)

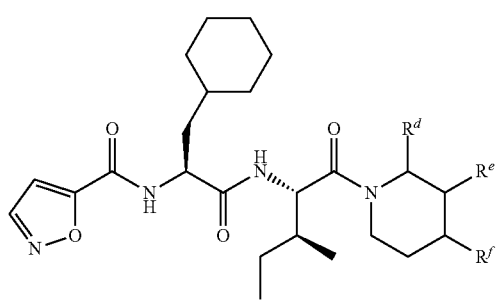

wherein
  $R^d$, $R^e$ and $R^f$ are each independently hydrogen, phenyl, benzyl, amidoalkyl, aminoaryl or a heterocycle,
  or $R^d$ and $R^e$ or $R^e$ and $R^f$ combined, form a fused aromatic or aliphatic $C_3$-$C_8$heterocyclic group; wherein the phenyl, benzyl, heterocycle or fused aromatic or aliphatic $C_3$-$C_8$heterocyclic group is optionally substituted with 1 to 3 substituents selected from alkyl, alkoxy, aminoalkyl, amidoalkyl, hydroxy, halo, nitro, dioxalane, trihaloalkyl, and trihaloalkoxy; or
a salt thereof.

6. The compound according to claim 1 wherein said compound is:
  5-isoxazoyl-Cha-Ile-aminomethylphenyl;
  5-isoxazoyl-Cha-Ile-aminomethyl-(2-methoxy)phenyl;
  5-isoxazoyl-Cha-Ile-aminomethyl-(3-methoxy)phenyl;
  5-isoxazoyl-Cha-Ile-aminomethyl-(4-methoxy)phenyl;
  5-isoxazoyl-Cha-Ile-aminomethyl-(2-methyl)phenyl;
  5-isoxazoyl-Cha-Ile-aminomethyl-(2-ethoxy)phenyl;
  5-isoxazoyl-Cha-Ile-aminomethyl-(2-propoxy)phenyl;
  5-isoxazoyl-Cha-Ile-aminomethyl-(2-isopropoxy)phenyl;
  5-isoxazoyl-Cha-Ile-aminomethyl-(2-butoxy)phenyl;
  5-isoxazoyl-Cha-Ile-aminomethyl-(2-isobutoxy)phenyl;
  5-isoxazoyl-Cha-Ile-aminomethyl-(2-chloro)phenyl;
  5-isoxazoyl-Cha-Ile-aminomethyl-(2-nitro)phenyl;
  5-isoxazoyl-Cha-Ile-aminomethyl-(2-trifluoromethyl)phenyl;
  5-isoxazoyl-Cha-Ile-aminomethyl-(3-trifluoromethoxy)phenyl;
  5-isoxazoyl-Cha-Ile-aminomethyl-(2-trifluoromethyl)phenyl;
  5-isoxazoyl-Cha-Ile-aminomethyl-(2-fluoro)phenyl;
  5-isoxazoyl-Cha-Ile-aminomethyl-(3-fluoro)phenyl;
  5-isoxazoyl-Cha-Ile-aminomethyl-(4-fluoro)phenyl;
  5-isoxazoyl-Cha-Ile-aminomethyl-(1,3-dioxalane)phenyl;
  5-isoxazoyl-Cha-Ile-aminomethyl-(3,4-dichloro)phenyl;
  5-isoxazoyl-Cha-Ile-aminomethyl-(2,4-dimethoxy)phenyl;
  5-isoxazoyl-Cha-Ile-aminomethyl-(2,5-dimethoxy)phenyl;
  5-isoxazoyl-Cha-Ile-aminomethyl-(3,4-dimethoxy)phenyl;
  5-isoxazoyl-Cha-Ile-aminomethyl-(2,3-dimethoxy)phenyl;
  5-isoxazoyl-Cha-Ile-aminomethyl-(2,3,4-dimethoxy)phenyl;
  5-isoxazoyl-Cha-Ile-aminomethyl-(2,6-dimethoxy)phenyl;
  5-isoxazoyl-Cha-Ile-aminomethyl-(2-methoxy-5-trifluoromethoxy)phenyl;
  5-isoxazoyl-Cha-Ile-aminomethyl-(2,4-dimethoxy)phenyl;
  5-isoxazoyl-Cha-Ile-aminomethyl-(3,5-bis(trifluoromethyl))phenyl;
  5-isoxazoyl-Cha-Ile-aminomethyl-(2-fluoro)phenyl;
  5-isoxazoyl-Cha-Ile-aminomethyl-(3-fluoro)phenyl;
  5-isoxazoyl-Cha-Ile-aminomethyl-(4-fluoro)phenyl;
  5-isoxazoyl-Cha-Ile-aminomethyl-(1,3-dioxalane)phenyl;
  5-isoxazoyl-Cha-Ile-aminomethyl-(3,4-dichloro)phenyl;
  5-isoxazoyl-Cha-Ile-(4-phenyl) piperidine;
  5-isoxazoyl-Cha-Ile-4-(p-methoxy)phenyl piperidine;
  5-isoxazoyl-Cha-Ile-4-(p-chloro)phenyl piperidine;
  5-isoxazoyl-Cha-Ile-4-(o-trifluoromethyl)phenyl piperidine;
  5-isoxazoyl-Cha-Ile-4-(o-phenyl)phenyl piperidine;
  5-isoxazoyl-Cha-Ile-4-(m-phenyl)phenyl piperidine;
  5-isoxazoyl-Cha-Ile-4-(p-phenyl)phenyl piperidine;
  5-isoxazoyl-Cha-Ile-4-(p-phenoxy)phenyl piperidine;
  5-isoxazoyl-Cha-Ile-4-(2,5-dimethoxy)phenyl piperidine;
  5-isoxazoyl-Cha-Ile-(4-benzyl)piperidine;
  5-isoxazoyl-Cha-Ile-2S-(tert-butylamide)piperidine;
  5-isoxazoyl-Cha-Ile-4-(4-acetamide)phenyl piperidine;
  5-isoxazoyl-Cha-Ile-3-(o-fluoro)aminophenylpiperidine;
  5-isoxazoyl-Cha-Ile-3-(m-fluoro)aminophenylpiperidine;
  5-isoxazoyl-Cha-Ile-3-(p-fluoro)aminophenylpiperidine;
  5-isoxazoyl-Cha-Ile-3-(o-trifluoromethyl)aminophenylpiperidine;
  5-isoxazoyl-Cha-Ile-3-(m-trifluoromethyl)aminophenylpiperidine;
  5-isoxazoyl-Cha-Ile-3-(p-trifluoromethyl)aminophenylpiperidine;
  5-isoxazoyl-Cha-Ile-spirochroman-2,4'-piperidine;
  5-isoxazoyl-Cha-Ile-[(S)-N-(tert-butyl)]piperidine;
  5-isoxazoyl-Cha-Ile-aminodimethyl-(2-methoxy)phenyl;
  5-isoxazoyl-Cha-Ile-(3-[aminomethyl]phenyl)-amino-4-aminobutane-1-carboxamide;
  5-isoxazoyl-Cha-Ile-(3-[aminomethyl]phenyl)-amino-3-aminopropane-1-carboxamide; or 5-isoxazoyl-Cha-Ile-4-(p-fluorophenyl)piperazine.

7. The compound according to claim 1 wherein said compound is:
  5-isoxazoyl-Cha-Ile-aminomethyl-benzimidazole;
  5-isoxazoyl-Cha-Ile-aminomethyl-2-biphenyl;
  5-isoxazoyl-Cha-Ile-aminomethyl-3-biphenyl;
  5-isoxazoyl-Cha-Ile-aminomethyl-4-biphenyl;
  5-isoxazoyl-Cha-Ile-aminomethyl-2-napthalene;

5-isoxazoyl-Cha-Thr(Me)-aminomethyl-(2-methoxy)phenyl;

5-isoxazoyl-Cha-Ile-{1-(methylsulfonyl)spiro[indoline-3,4'-piperidine]};

5-isoxazoyl-Cha-Ile-{3H-3-oxo-spiro[isobenzofuran-1,4'-piperidine]};

5-isoxazoyl-Cha-Ile-(4-oxo-spiro[chroman-2,4'-piperidine]); or 5-isoxazoyl-Cha-Ile-spiro[chroman-2,4'-piperidine].

8. A method of modulating the activity of PAR2 comprising exposing the receptor to a compound according claim 1.

9. A pharmaceutical composition comprising a compound according to claim 1 and a pharmaceutically acceptable carrier, excipient, diluent and/or adjuvant.

10. The compound according to claim 1, represented by the formula (Ia):

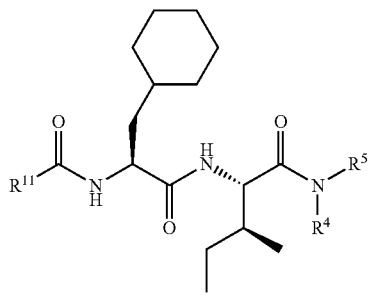

(Ia)

wherein $R^{11}$ is a 5- or 6-membered unsaturated heterocyclic ring comprising 1 to 3 heteroatoms selected from N and O, optionally substituted with one or more substituents selected from alkyl, alkoxy, amine, aminoalkyl, amidoalkyl, halo, hydroxy, trihaloalkyl, trihaloalkoxy and phenyl, wherein the phenyl group is optionally substituted with 1 to 3 substituents selected from alkyl, alkoxy, hydroxy, halo, nitro, trihaloalkyl or trihaloalkoxy;

$R^4$ is hydrogen, $C_1$-$C_6$alkyl, aminoalkyl or amidoalkyl;

$R^5$ is a benzyl group, optionally substituted with a group selected from alkyl, aminoalkyl, alkoxy, $C_4$-$C_7$heterocycle, hydroxy, halo, nitro, dioxalane, trihaloalkyl, trihaloalkoxy and —C(O)NHCHR$^9$R$^{10}$;

$R^9$ is —C(O)NH$_2$ and $R^{10}$ is a $C_2$-$C_5$aminoalkyl; or $R^4$ and $R^5$ combined, together with the nitrogen to which they are attached, form piperidine, optionally substituted but not fused with a group selected from phenyl, benzyl, amidoalkyl or a heterocycle; wherein the phenyl, benzyl or heterocycle may be further substituted with 1 to 3 substituents selected from alkyl, alkyloxy, aminoalkyl, amidoalkyl, hydroxy, halo, nitro, dioxalane, trihaloalkyl, or trihaloalkoxy; or a salt thereof.

* * * * *